United States Patent
Abramson et al.

(10) Patent No.: US 12,336,902 B2
(45) Date of Patent: *Jun. 24, 2025

(54) OCULAR PROSTHESIS WITH DISPLAY DEVICE

(71) Applicant: Sloan Kettering Institute for Cancer Research, New York, NY (US)

(72) Inventors: David Abramson, New York, NY (US); George C. Bohle, III, Bloomingdale, NJ (US); Paul Frisch, Nanuet, NY (US); Brian P. Marr, New York, NY (US); Paul Booth, New York, NY (US); Philip C. Black, Woodbridge, CT (US); Alan B. Katze, Oxford, CT (US); James G. Moore, Guilford, CT (US)

(73) Assignee: Sloan Kettering Institute for Cancer Research, New York, NY (US)

( * ) Notice: Subject to any disclaimer, the term of this patent is extended or adjusted under 35 U.S.C. 154(b) by 1158 days.

This patent is subject to a terminal disclaimer.

(21) Appl. No.: 16/949,528

(22) Filed: Nov. 2, 2020

(65) Prior Publication Data

US 2021/0045865 A1 Feb. 18, 2021

Related U.S. Application Data

(62) Division of application No. 14/760,198, filed as application No. PCT/US2014/010761 on Jan. 8, 2014, now Pat. No. 10,820,986.

(Continued)

(51) Int. Cl.
*A61F 2/14* (2006.01)
*A61B 5/00* (2006.01)
(Continued)

(52) U.S. Cl.
CPC ............... *A61F 2/141* (2013.01); *A61B 5/11* (2013.01); *A61B 5/6821* (2013.01);
(Continued)

(58) Field of Classification Search
None
See application file for complete search history.

(56) References Cited

U.S. PATENT DOCUMENTS

| 3,905,130 | A | 9/1975 | Gordon et al. |
| 4,272,910 | A | 6/1981 | Danz |

(Continued)

FOREIGN PATENT DOCUMENTS

| DE | 102010050843 A1 | 5/2012 |
| WO | 198601996 A1 | 4/1986 |

(Continued)

OTHER PUBLICATIONS

Myradale, Discussion of hemispherical LED or LCD or OLED panel, Halfbakery (website), May 13, 2005, Published in: http://www.halfbakery com/idea/hemispherical_20LCD_20panel (Year: 2005).*

(Continued)

*Primary Examiner* — Leslie A Lopez
(74) *Attorney, Agent, or Firm* — Wolter Van Dyke, PLLC; Eugene J. Molinelli

(57) ABSTRACT

An ocular prosthesis includes a display device visible at an anterior portion of the ocular prosthesis. The display device is configured to present a changeable image that represents a natural appearance and movement for a visible portion of an eyeball of a subject. A system includes, besides the ocular prosthesis, an implant marker configured to move with an orbital implant disposed in an eye socket of a subject. A method includes determining a change in orientation of an orbital implant in a subject and determining an update to a (Continued)

natural appearance for a visible portion of an eyeball for the subject based on the change in orientation of the orbital implant. The method also includes rendering an update to an image of the natural appearance for a display device disposed in an ocular prosthesis configured to be inserted in the subject anterior to the orbital implant.

3 Claims, 33 Drawing Sheets

Related U.S. Application Data

(60) Provisional application No. 61/750,421, filed on Jan. 9, 2013.

(51) Int. Cl.
*A61B 5/11* (2006.01)
*A61F 2/48* (2006.01)

(52) U.S. Cl.
CPC ............ *A61B 2560/0223* (2013.01); *A61B 2562/0219* (2013.01); *A61B 2562/0223* (2013.01); *A61B 2562/046* (2013.01); *A61F 2/482* (2021.08); *A61F 2230/0004* (2013.01); *A61F 2230/0019* (2013.01); *A61F 2250/0096* (2013.01); *A61F 2250/0097* (2013.01)

(56) References Cited

U.S. PATENT DOCUMENTS

| | | |
|---|---|---|
| 5,004,443 A | 4/1991 | Su |
| 6,391,057 B1 | 5/2002 | Schleipman et al. |
| 6,576,013 B1 | 6/2003 | Budman et al. |
| 8,960,898 B1 | 2/2015 | Etzkorn et al. |
| 2006/0095128 A1 | 5/2006 | Blum et al. |
| 2006/0183986 A1 | 8/2006 | Rice et al. |
| 2009/0189974 A1 | 7/2009 | Deering |
| 2009/0292614 A1 | 11/2009 | Reichow et al. |
| 2010/0001926 A1 | 1/2010 | Amirparviz et al. |
| 2011/0177753 A1 | 7/2011 | Irmler et al. |

FOREIGN PATENT DOCUMENTS

| | | | | |
|---|---|---|---|---|
| WO | WO 86/01996 | * | 4/1986 | ............ A61F 2/14 |
| WO | 2000038592 A1 | | 7/2000 | |
| WO | 2006034336 A1 | | 3/2006 | |
| WO | 2011134081 A1 | | 11/2011 | |

OTHER PUBLICATIONS

ISA/US, "International Search Report and Written Opinion for the corresponding PCT application PCT/US14/10761", Apr. 12, 2014, p. 9.
EPO, Third party observation concerning P3015PC00, Aug. 4, 2015, p. 2, Publisher: PCT.
Myradale, Discussion of hemispherical LED or LCD or OLED panel, Halfbakery (website), May 13, 2005, Published in: http://www.halfbakery.com/idea/hemispherical_20LCD_20panel.
Extended EP Search Report, EP Application No. 14738194.1, Dated Jul. 6, 2016, pp. 1-6.

* cited by examiner

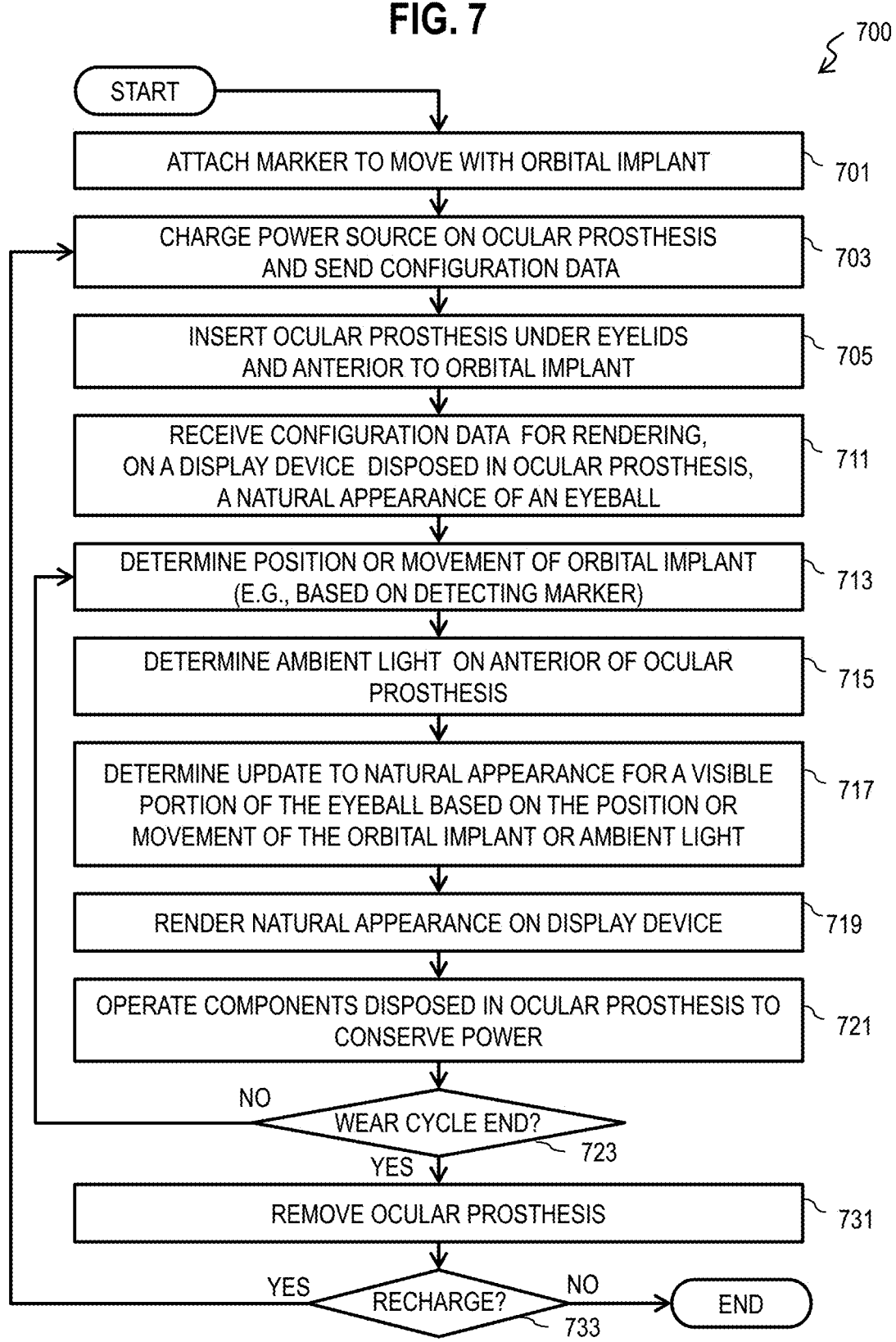

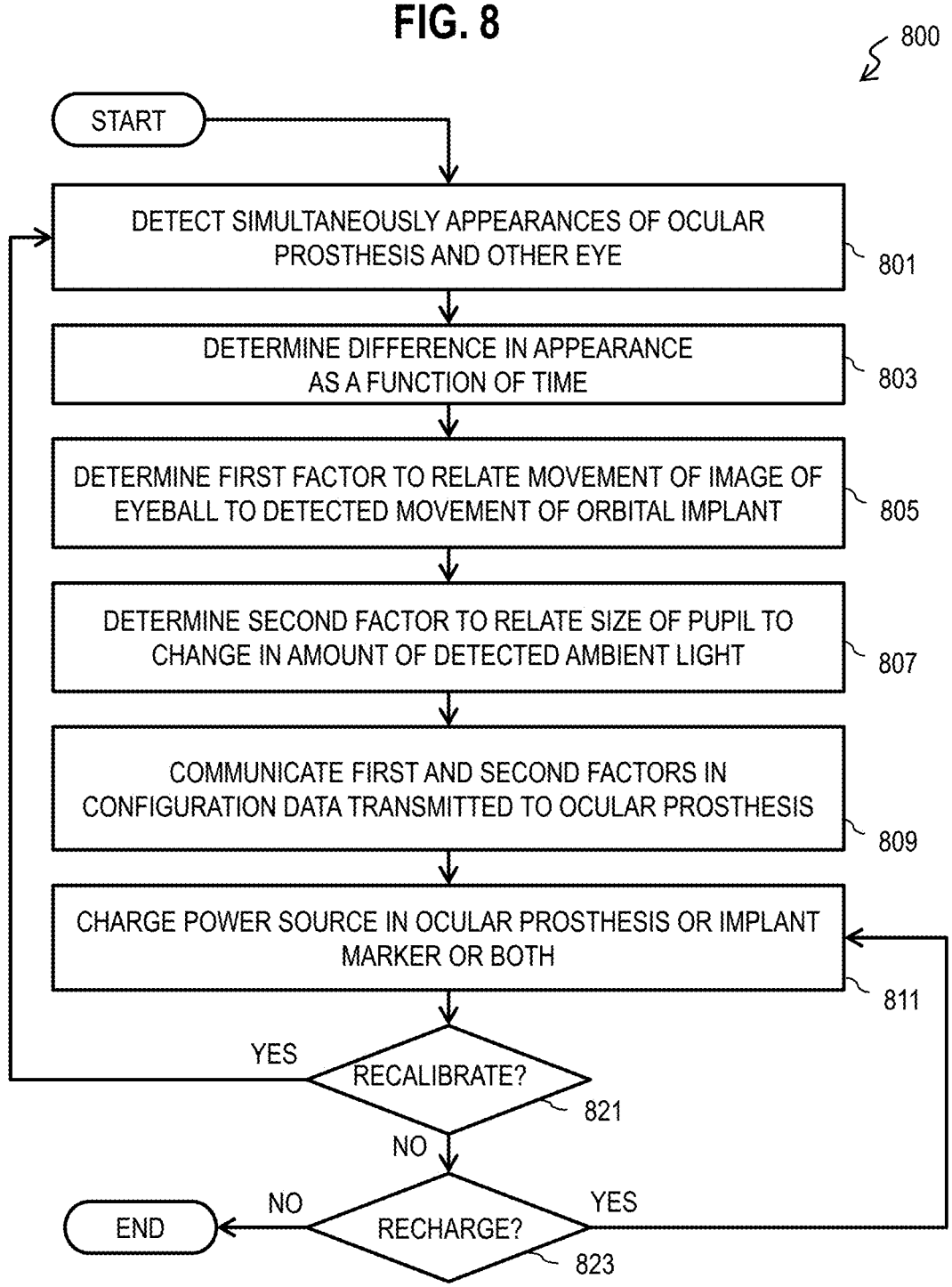

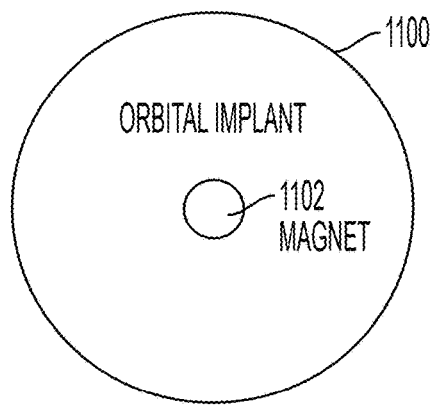
FIG. 11A
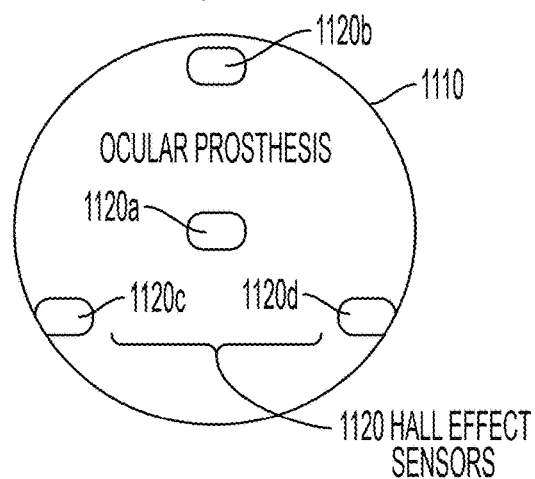
FIG. 11B
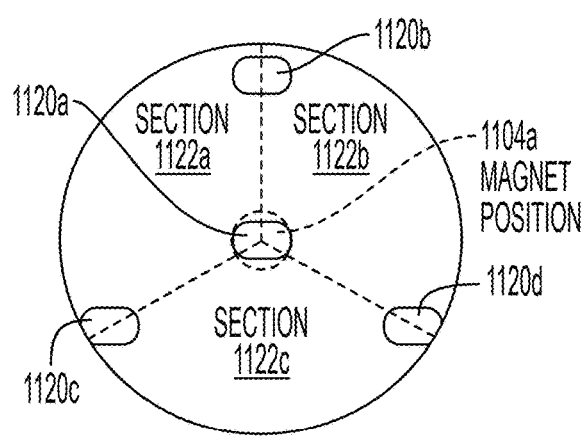
FIG. 11C
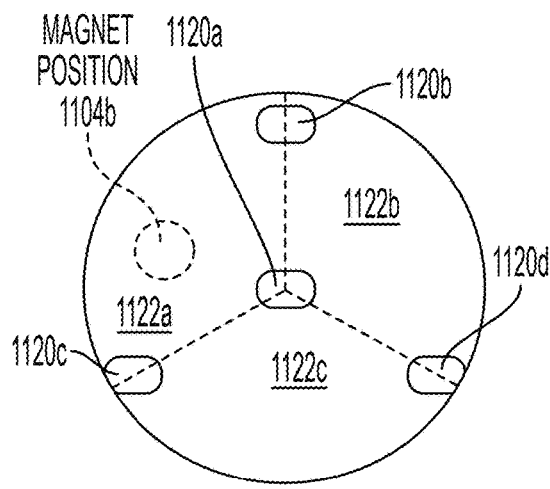
FIG. 11D
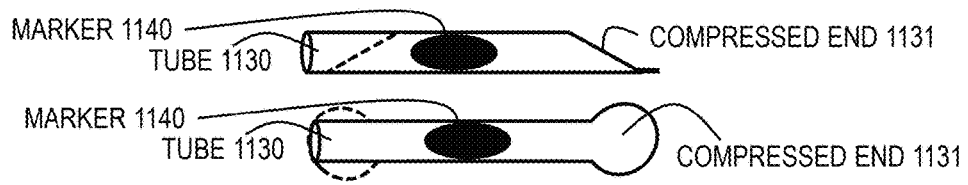
FIG. 11E
FIG. 11F

FIG. 12A
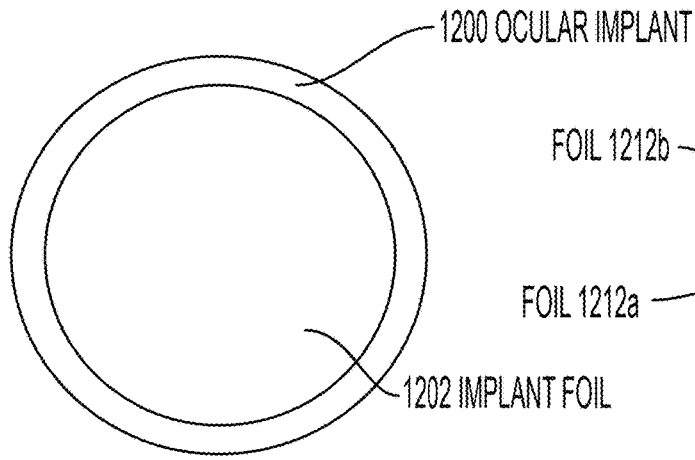
FIG. 12B
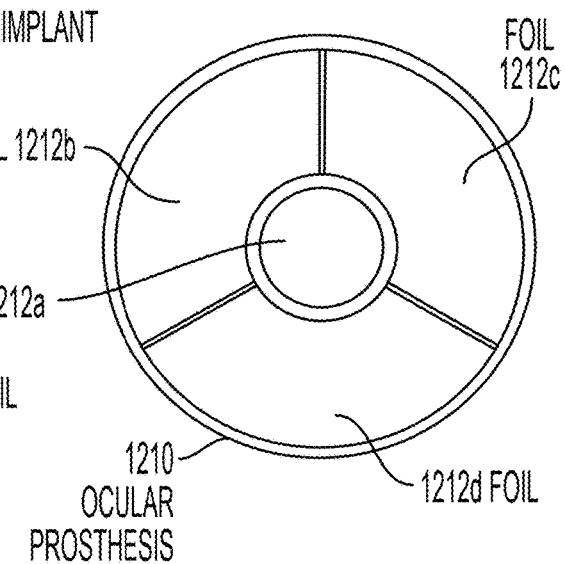
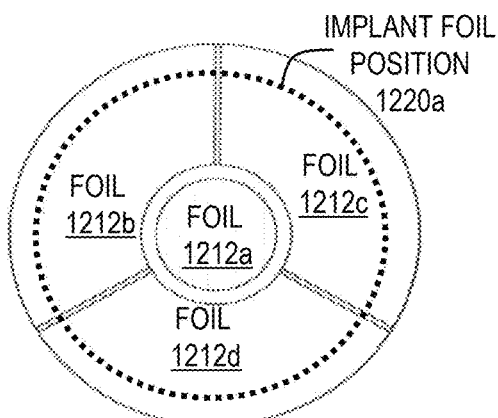
FIG. 12C
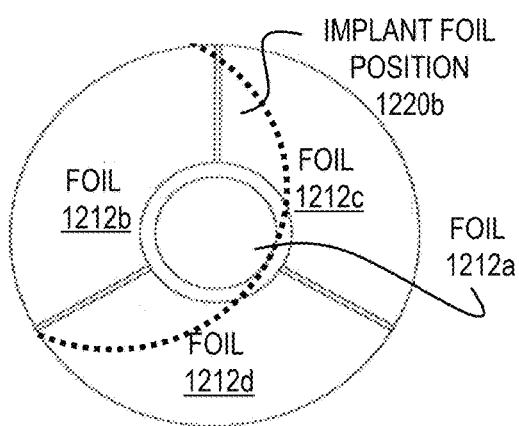
FIG. 12D
FIG. 12E
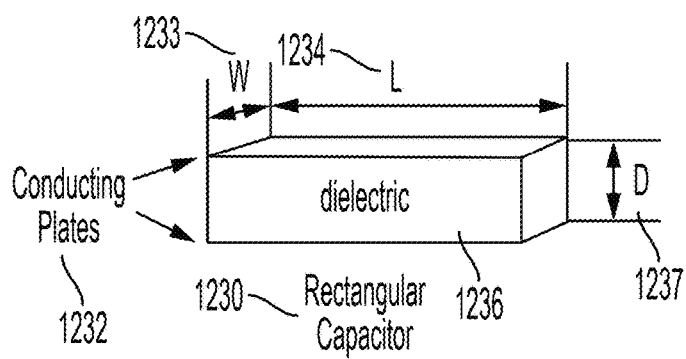
FIG. 12F
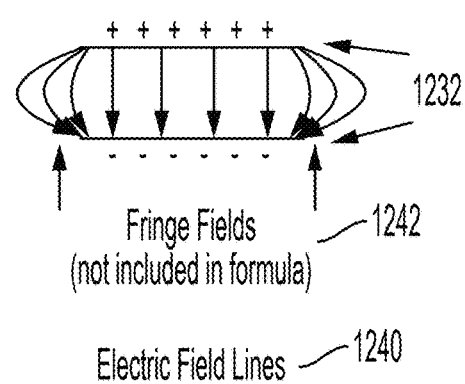

FIG. 15A

Hamamatsu, 3 mm height, w/mux

| 1512a | 1512b | 1512c | 1512d |
|---|---|---|---|
| | | DVM at 6000 | DVM at point |
| 6000 | 6050 | 720 | 714 |
| 6000 | 6100 | 695 | 683 |
| 6000 | 6150 | 678 | 660 |
| 6000 | 6200 | 659 | 621 |
| 6000 | 6250 | 654 | 591 |
| 6000 | 6300 | 637 | 552 |
| 6000 | 6350 | 634 | 512 |
| 6000 | 6400 | 611 | 473 |
| 6000 | 6450 | 604 | 439 |
| 6000 | 6500 | 588 | 406 |
| 6000 | 6550 | 578 | 379 |
| 6000 | 6600 | 567 | 346 |
| 6000 | 6650 | 558 | 334 |
| 6000 | 6700 | 557 | 314 |
| 6000 | 6750 | 543 | 296 |
| 6000 | 6800 | 539 | 299 |
| 6000 | 6850 | 529 | 279 |
| 6000 | 6900 | 525 | 270 |
| 6000 | 6950 | 515 | 272 |
| 6000 | 7000 | 510 | 263 |
| 6000 | 7050 | 503 | 263 |
| 6000 | | 502 | |

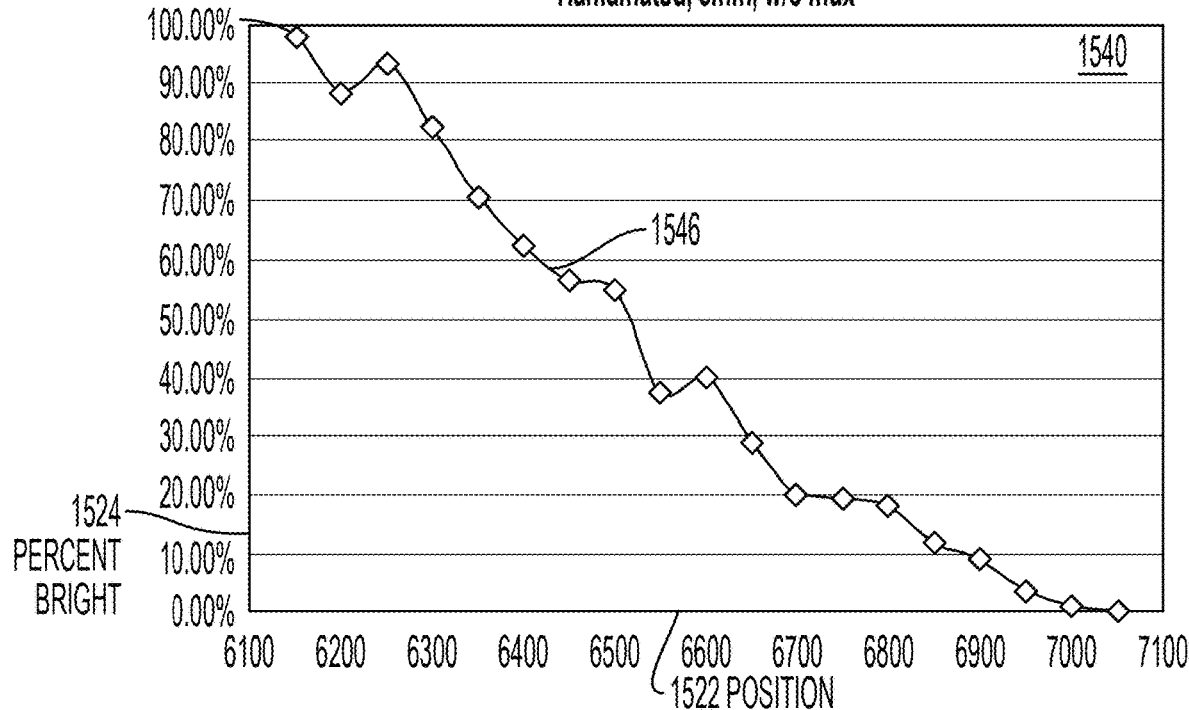
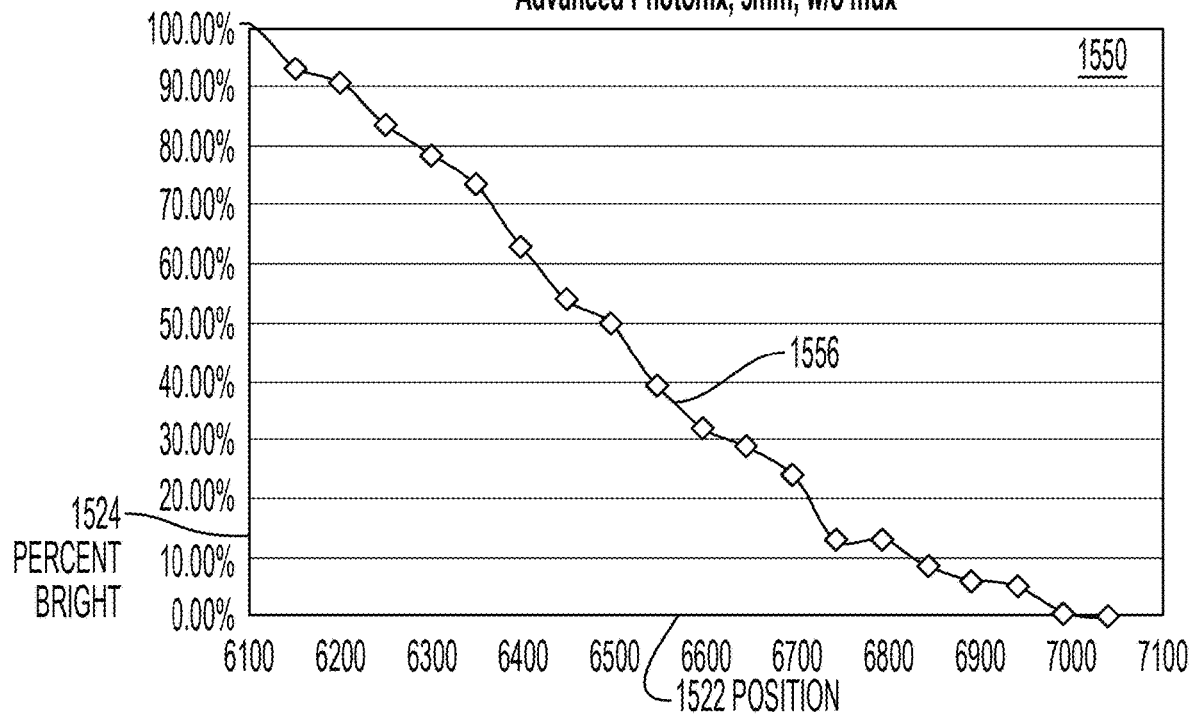

Photodiode Layout

OCULAR PROSTHESIS WITH DISPLAY DEVICE

BACKGROUND OF THE INVENTION

Twelve thousand patients a year lose an eye in the U.S. from accidents, infections, cancer, congenital anomalies and advanced ocular conditions such as diabetes and glaucoma. It is estimated that a quarter of a million Americans already have prostheses, and millions are estimated to have such prostheses or are in need of such prostheses worldwide. An ocular prosthesis is generally a molded, painted methylmethacrylate device placed between the lids for people who have lost eyes. This plastic needs polishing and ultimately replacement about every five years. Conventional prostheses may have a colored outer surface that resembles the natural eye of the patient. Current prosthetic eyes can have a good appearance in photographs, but have limited or no movement and therefore do not appear realistic when the patient attempts to move his or her eyes. Also, conventional prostheses do not have pupils that respond to light. Therefore, such prostheses are a daily reminder of an obvious deformity and lead to insecurity of the patient, a reluctance to be seen in public, a feeling of inferiority, and unhappiness.

Over the years ophthalmic surgeons have tried many ways to create a prosthesis that moves, but such attempts have failed. When the eye is removed, a sphere (also referred to as an orbital implant) the size of the normal eye is placed in the socket and the conjunctiva (transparent mucous membrane that normally covers the sclera that is often referred to as the white portion of the eye) is surgically closed over the sphere. With modern surgical techniques, movement of the sphere is good as the normal muscles around the eye (six of them) are often attached to the sphere, either directly or indirectly by way of the conjunctiva. The conjunctiva that is placed over the sphere, however, continues as the bulbar conjunctiva into the fornices above and below an anterior portion of the sphere, and continues as the palpebral conjunctiva that lines the undersurface of the upper and lower eyelids. The modern-day plastic prosthesis then sits within this closed loop of tissue (called the prosthesis space, hereinafter) formed by the palpebral conjunctiva, the bulbar conjunctiva and the conjunctiva. Many attempts to couple the ball and the prosthesis have been tried since the first ocular prosthesis was created just over 100 years ago; however, it is believed that all such attempts have failed to produce natural movement of the prosthesis.

SUMMARY OF THE INVENTION

The inventors have determined that one reason that such prostheses have failed to achieve natural looking movement is for a simple anatomic reason—despite occasionally complete movement of the orbital implant, there is no space in the closed loop of tissue formed by the conjunctiva (called the prosthesis space, herein) for the prosthesis to move sufficiently to demonstrate normal motility. Techniques are provided for providing realistic-looking movement in this confined prosthesis space using a display device, such as an electronic or mechanical display device. Thus, the inventors have developed a prosthetic eye that fits an unmet need for patients who have lost an eye to disease or trauma or congenital malformations or cancer or severe infection, by providing a prosthetic eye that appears to have lifelike movements and, in some embodiments, a pupil that responds to light.

In a first set of embodiments, an ocular prosthesis includes a display device visible at an anterior portion of the ocular prosthesis, wherein the display device is configured to present a changeable image that represents a natural appearance and movement for a visible portion of an eyeball of a subject.

In a second set of embodiments, an ocular prosthesis includes a housing having a form factor shaped to fit under an eyelid of a subject and in front of an orbital implant disposed in an eye socket of the subject, wherein an anterior portion of the form factor is curved similar to an anterior portion of a natural eyeball for the subject. The prosthesis also includes a display device disposed within the housing and visible at an anterior portion of the housing, and an implant detector disposed within the housing and configured to detect angular orientation of the orbital implant relative to the subject when the housing is disposed under the eyelid of the subject and anterior to the orbital implant. The prosthesis further includes a processor disposed within the housing and configured to determine, at least in part, a natural appearance for a visible portion of the eyeball of the subject based, at least in part, on the angular orientation of the orbital implant, and render, at least in part, an image for presentation on the display based on the natural appearance for the visible portion of the eyeball of the subject. The ocular prosthesis still further includes a power source disposed within the housing and configured to provide power for the display device, the implant detector and the processor.

In a third set of embodiments, an ocular prosthetic system includes an implant marker configured to move with an orbital implant disposed in an eye socket of a subject, and an electronic ocular prosthesis. The electronic ocular prosthesis includes a housing having a form factor shaped to fit under an eyelid of the subject and in front of the orbital implant, wherein an anterior portion of the form factor is curved similar to an anterior portion of a natural eyeball for the subject. The electronic ocular prosthesis also includes a display device disposed within the housing and visible at an anterior portion of the housing, and an implant detector disposed within the housing and configured to detect a position of the implant marker when the housing is disposed under the eyelid of the subject and anterior to the orbital implant. The electronic ocular prosthesis further includes a processor disposed within the housing and configured to determine, at least in part, a natural appearance for a visible portion of the eyeball of the subject based, at least in part, on the position of the implant marker, and render, at least in part, an image for presentation on the display device based on the natural appearance for the visible portion of the eyeball of the subject.

In a fourth set of embodiments, a method includes determining a change in orientation of an orbital implant in a subject, and determining an update to a natural appearance for a visible portion of an eyeball for the subject based on the change in orientation of the orbital implant. The method further includes rendering an update to an image of the natural appearance for a display device disposed in an ocular prosthesis configured to be inserted in the subject anterior to the orbital implant.

In a fifth set of embodiments, an apparatus includes a housing and a detectable device. The housing includes a broad portion configured to be attached to an orbital implant or conjunctiva adjacent to the orbital implant. The detectable device is disposed in the housing adjacent to the broad portion, and is configured to be detected remotely.

In other embodiments, an apparatus or computer-readable medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 7 is a flow diagram that illustrates an example method for operating an ocular prosthesis with a display device, according to an embodiment;

FIG. 8 is a flow diagram that illustrates an example method for externally calibrating and charging an ocular prosthesis with a display device, according to an embodiment;

FIG. 9C is a block diagram that illustrates an example image for rendering on a display device, according to an embodiment;

FIG. 9D is a block diagram that illustrates an example screen for controlling properties of the image and image changes over time to determine acceptable display properties, according to an embodiment;

FIG. 11A through FIG. 11D are block diagrams that illustrate example detection of a magnet on the orbital implant with Hall Effect sensors on the ocular prosthesis, according to an embodiment;

FIG. 11E through FIG. 11J are block diagrams that illustrate an example marker configured to be attached to the conjunctiva that moves with the orbital implant, according to various embodiments;

FIG. 12A through FIG. 12D are block diagrams that illustrate example detection of the orientation the orbital implant with sensors on the ocular prosthesis that measure variable capacitance, according to an embodiment;

FIG. 12E and FIG. 12F are block diagrams that illustrate example factors that affect the measured variable capacitance, according to an embodiment;

FIG. 12G through FIG. 12L are block diagrams that illustrate example detection of a conductor moving with the orbital implant using inductance sensors on the ocular prosthesis, according to an embodiment.

FIG. 15A is a table that illustrates example variation of detected light intensity with angular separation between photodiode and light emitting implant marker, according to an embodiment;

FIG. 15B through FIG. 15E are graphs that illustrate example variations of detected light intensity with angular separation between photodiode and light emitting marker on a experimental orbital implant, according to various embodiments;

FIG. 16C is a table that illustrates example power consumption of various components of the optical sensor circuitry, according to some embodiments;

DETAILED DESCRIPTION

A method and apparatus are described for an ocular prosthesis with a display device. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of a self-contained ocular prosthesis with an electronic display working in concert with a marker configured to move with an orbital implant. However, the invention is not limited to this context. In other embodiments some of the functions of the ocular prosthesis (such as power storage or data processing or ambient light detection or implant orientation detection or natural eye orientation detection) are performed in a wearable device external to the ocular prosthesis or external to both the orbital implant and the ocular prosthesis, or the marker is omitted, or the orbital implant is omitted, or motion of the remaining natural eye is tracked, or a mechanical display or chemical display is used instead of, or in addition to, an electronic display or the system is changed in some combination of ways.

1. Overview

Various embodiments of the ocular prosthetic system described herein can be provided to patients as a new prosthesis, or a patient's existing implant or prosthesis can be retrofitted to incorporate features of the invention. Certain groups of patients may require variations on the orbital implant and the associated procedures. For example, one group includes those who are newly fitted with an orbital implant (which is preferentially anchored to the muscles), and another group includes those who already have an orbital implant and, in lieu of replacing the existing implant with a new orbital implant, patients in this group can be retrofitted. As used herein, the term subject is used to refer to a machine an organism that hosts the ocular prosthesis system, whether a human patient or an animal patient or a test animal or a volunteer of some sort or a robot.

Figure 1:
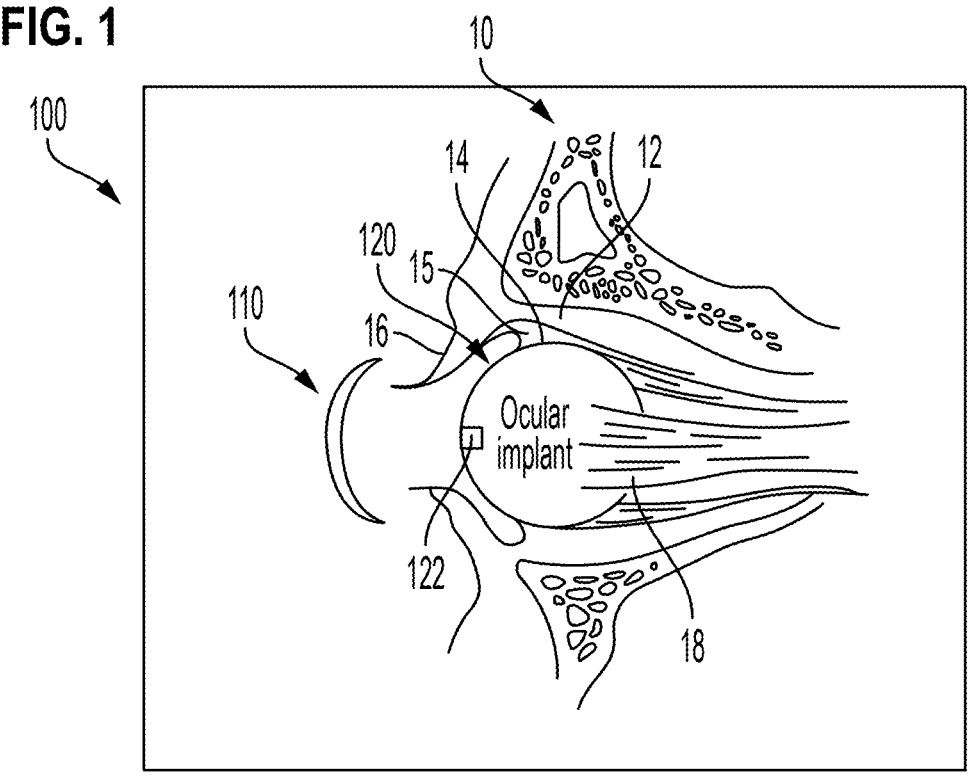
FIG. 1 is a block diagram that illustrates a side view of an example ocular prosthetic system including an orbital implant inserted within a patient eye socket and an ocular prosthesis in a non-inserted state, according to an embodiment of the present invention.
Figure 2:
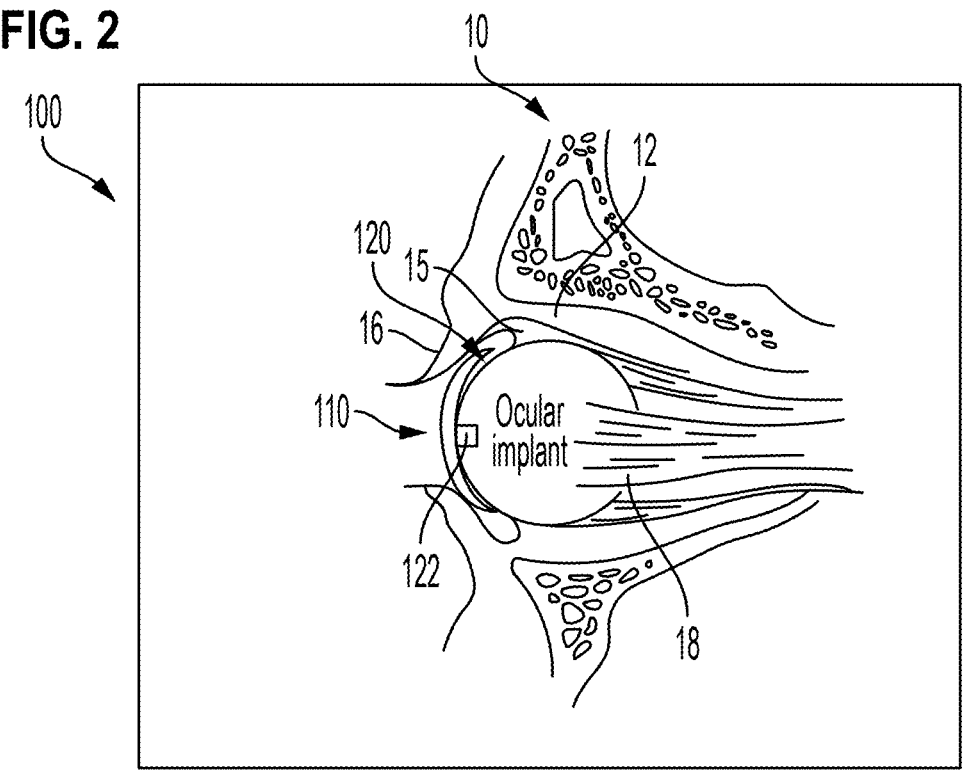
FIG. 2 is a block diagram that illustrates a side view of an example ocular prosthetic system including an orbital implant inserted within a patient eye socket and an ocular prosthesis provided in an inserted state adjacent and anterior to the orbital implant, according to an embodiment.

FIG. 1 is a block diagram that illustrates a side view of an example ocular prosthetic system including an orbital implant 120 inserted within a subject eye socket 12 and an ocular prosthesis 110 in a non-inserted state, according to an embodiment of the present invention. The orbital implant 120 is surgically inserted within a subject eye socket 12 within the subject skull 10. FIG. 2 is a block diagram that illustrates a side view of an example ocular prosthetic system including an orbital implant 120 inserted within a subject eye socket 12 and an ocular prosthesis 110 provided in an inserted state adjacent and anterior to the orbital implant 120, according to an embodiment.

Generally, the orbital implant 120 is capable of movement, albeit not always full movement; the movement can vary from subject to subject. Degree of movement (called motility herein) depends on whether or not the orbital implant 120 is attached to the muscles 18, and also on the differences in movement capability of the muscles which are attached. In some subjects, a firm capsule forms around the implant 120 and the muscles 18 naturally attach to the capsule allowing the orbital implant to move. The movement of the implant is rarely comparable to the movement in the unaffected eye. In some subjects, the conjunctiva 14 surrounds the implant 120 and moves with the implant 120.

A closed loop of tissue (the prosthesis space) is formed by the conjunctiva 14 covering the implant and the fornices 15 above and below, and the undersurfaces of the eyelids 16. A fornix is generally the pouch like space between the undersurface of the eye lid and eyeball into which a prosthesis sits. Even with complete movement of the orbital implant 120 in response to muscles 18, an inserted ocular prosthesis 110 is constrained by this closed loop of tissue that prevents realistic motility. Thus, in various embodiments, the ocular prosthesis includes an electronic display device or mechanical facsimile that mimics natural movement of an iris and or pupil and or blood vessels normally visible to an observer—even though movement of the ocular prosthesis 110 itself is limited or absent.

The embodiment depicted in FIG. 1 and FIG. 2 includes an implant marker 122 (such as a tattoo, or a magnet, or non-magnetic foil or light emitter, as described in some detail below, or some combination, in various embodiments) provided within or retrofitted to be included on or within the orbital implant 120 or the conjunctiva 14 that cover the implant 120. In this embodiment, a sensor (such as a Hall Effect sensor for the inserted magnet or a second foil or a photodiode, or some other sensor, alone or in combination) provided within the ocular prosthesis 110 senses the relative motion between the implant marker 122 on the orbital implant 120 and the ocular prosthesis 110, which allows a processor within the ocular prosthesis to determine the intended, lifelike motion of the eye using predetermined calibration measurements, as will be described in greater detail below. The Hall Effect was discovered by Edwin Hall in 1879, and it generally refers to the production of a voltage difference (the Hall voltage) across an electrical conductor, transverse to an electric current in the conductor and a magnetic field perpendicular to the current. The ocular prosthesis 110 then utilizes this data to render on a display device (e.g., electronically or mechanically or chemically, or some combination) lifelike motion of an eye. Additionally, a light sensor provided on the ocular prosthesis is used in some embodiments to sense an ambient light level, and the ocular prosthesis 110 can then utilize this data to render on the display device (e.g., electronically or mechanically or chemically) lifelike size/adjustment of the pupil of the eye.

Thus, in the embodiment depicted in FIG. 1 and FIG. 2, the orbital implant 120 for a newly fitted subject contains a marker 122 which can be coated in biocompatible material, such as an epoxy, among others. For retrofit subjects, a "retrofit kit" is provided to a doctor performing the retrofitting. In such a kit, the marker is injected by needle or placed in a hole cut with a drill to insert the marker into an orbital implant already in place, or the marker is placed in a bio-compatible tube that is then closed at each end and sutured or otherwise allowed to become embedded in the conjunctiva 14 or scar-conjunctival complex overlying the orbital implant 120.

Figure 3A:
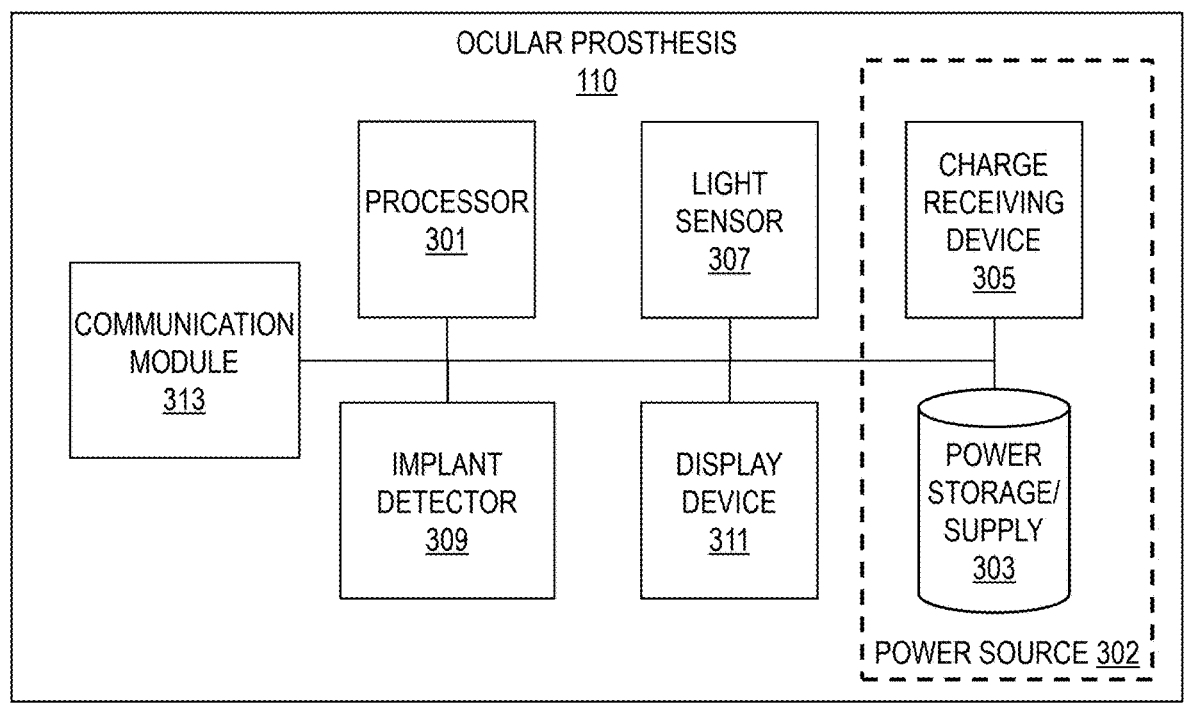
FIG. 3A is a block diagram that illustrates example components of an ocular prosthesis, according to an embodiment.
Figure 3B:
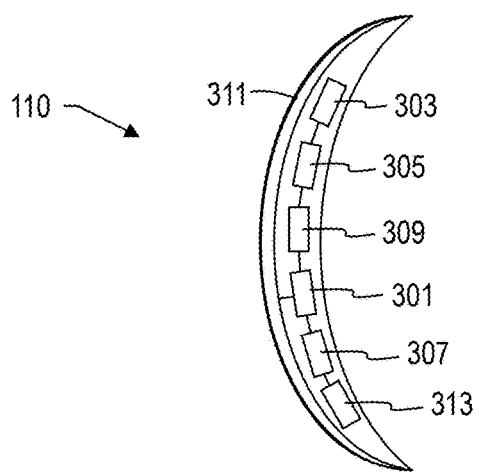
FIG. 3B is a block diagram that illustrates example components of an ocular prosthesis in a form factor suitable for insertion, according to an embodiment.
Figure 3C:
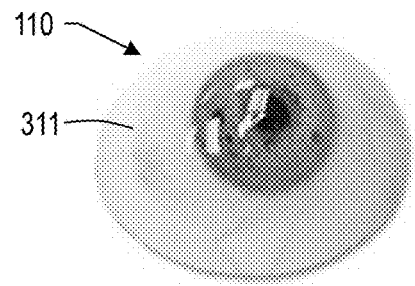
FIG. 3C is a perspective view that illustrates the example ocular prosthesis of FIG. 3A, according to an embodiment.

FIG. 3A is a block diagram that illustrates example components of an ocular prosthesis 110, according to an embodiment. FIG. 3B is a block diagram that illustrates example components of an ocular prosthesis 110 in a housing having a form factor suitable for insertion into the prosthesis space, according to an embodiment; and FIG. 3C is a perspective view that illustrates the example ocular prosthesis 110 of FIG. 3A, according to an embodiment. Note that while the depiction in FIG. 3C is in grayscale, the ocular prosthesis 110 can be provided with natural eye coloring in order to appear lifelike (also called natural herein).

In the embodiment depicted in FIG. 3A and FIG. 3B, In various embodiments, the ocular prosthesis includes a display device 311. The display device is arranged in the ocular prosthesis to be visible at an anterior portion of the housing. In some embodiments, the display is a flat display with lenses arranged to simulate curvature of the anterior portion of a natural eyeball. In some embodiments, the display is a flat display that uses software instructions to transform the image to simulate the appearance of movement of an iris along a curved surface. In some embodiments, the display is a flexible display that is bent into a horizontally curved and vertically curved surface. In some embodiments, the display is a flexible display that is bent into a horizontally curved surface. In some embodiments the display is an emissive display that emits light. In some embodiments, an emissive display is configured to emit different amounts of light under different lighting conditions to reduce glow in low light conditions. In some embodiments, the display is a reflective display that merely absorbs some colors and reflects other colors of ambient light that impinges on the display. Such displays have the advantage that they do not appear to glow in low light conditions, and thus appear more natural. In some embodiments, the prosthesis contains a mechanical facsimile of the iris that uses mechanical means to simulate movement of a facsimile of the subject's healthy eye. A mechanical pupil is also envisioned with this possibility. In some embodiments, the mechanical means include small motors that physically move the iris throughout its intended range of motion within the prosthesis. Pupil response is initiated with motors moving a mechanical iris similar to the aperture mechanism in a camera lens with "leaves," or alternatively with some electrically responsive material that expands and contracts based on an electrical input.

In the illustrated embodiment, the ocular prosthesis also includes an implant detector 309 and a processor 301. The illustrated embodiment also includes a power source 302 that includes a power storage/supply unit 303 (e.g., a battery) and a charge receiving device 305 (e.g., a inductive charge receiving device that can be wirelessly charged using a separate inductive charging station, or a charge receiving device having electrical contact for wired connection to a charging station, among others). For example, in some embodiments the charge receiving device 305 includes an induction coil. The illustrated embodiment of the ocular prosthesis 110 also includes a light sensor 307 (e.g., a photovoltaic cell, a photoresistor, an optical detector, or a photodiode, among others, or some combination). The illustrated embodiment of the ocular prosthesis 110 also includes a communication module 313 (e.g., contacts for a wired transceiver or an antenna with or without a tuning circuit for a wireless receiver or transceiver).

In various embodiments, the communication module 313 is a communication component that can communicate with a programming unit in order to receive calibration information, software, or other data that can be utilized by the other components such as the processor 301, among others. For example, in some embodiments, the communication module 313 includes an antenna for picking up signal sent as an electromagnetic wave. In some embodiments, the antenna of communication module 313 doubles as an induction coil for the charge receiving device 305.

In various embodiments, the processor 301 is configured as a chip set with a micro-processor and a memory, as described in more detail below with reference to FIG. 22. In some embodiments, the processor 301 is configured to receive various data from the communication module 313, the light sensor 307, and the implant detector 309, and then send control signals to the display device 311 in order to have the display device 311 provide a lifelike display (e.g., color, motion of the iris/pupil, size of the iris/pupil, or presence/prevalence of blood vessels, among others, alone or in some combination).

In some embodiments, there is a coating on the ocular prosthesis. In some embodiments, the ocular prosthesis is made of methylmethacrylate, with the various components, such as the electronic parts and light sensor, embedded within this plastic. In various embodiments, the ocular prosthesis is waterproof.

In various embodiments, the implant detector 309 includes one or more sensors to provide an accurate detection of the relative movement between the implant marker 122 and the ocular prosthesis 110. In various embodiments, the display device 311 is configured to present a computer-generated image of a visible portion of an eye of the subject, which is visible over at least a portion of the anterior surface of the ocular prosthesis 110 as shown in FIG. 3B and FIG. 3C. In various embodiments, one or more features of the image representing the natural appearance of an eye of the subject are controlled in order to provide a natural appearance with lifelike eye features and motions. In some embodiments, a charging station is provided to the subject by which the subject can charge the power source 302 of the ocular prosthetic system 110 via the charge receiving device 305. For example, in some embodiments, the power source is recharged by removing the ocular prosthesis 110 from the subject's body and connecting (either wirelessly or via wired connection) the ocular prosthesis 110 to the charger of a charging station for a period of time (e.g., overnight) sufficient to provide operation for all or most of the remaining day.

In various embodiments, the power storage/supply unit 303 is any type of battery. In some embodiments, the ocular prosthesis 110 is powered by some external source of energy, e.g., in a wearable device, thus removing the need for one or both of an internal power storage/supply unit 303 and charge receiving device 305. For example, in some embodiments, the ocular prosthesis is powered using microwaves (e.g., making use of radiation from cell-phones or other external device); while, in some embodiments, the ocular prosthesis is powered by converting the subject's body's own heat into electricity.

Figure 4:
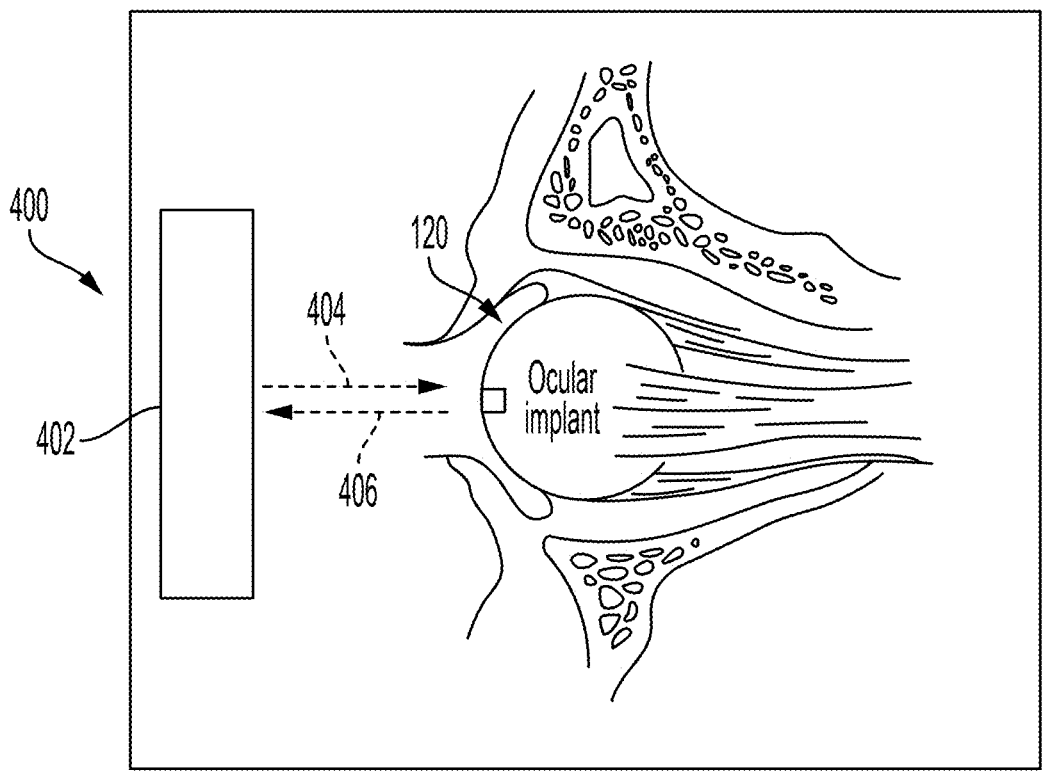
FIG. 4 is a block diagram that illustrates an example calibration device in use for calibrating an ocular prosthesis, according to an embodiment.
Figure 5:
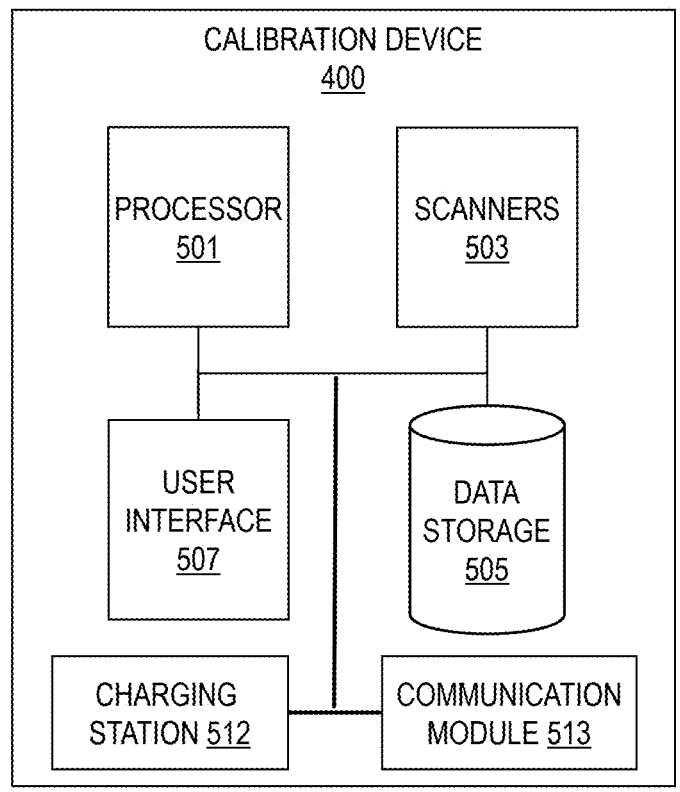
FIG. 5 is a block diagram that illustrates an example calibration device for use in calibrating an ocular prosthesis, according to an embodiment.

FIG. 4 is a block diagram that illustrates an example calibration device in use for calibrating an ocular prosthesis, according to an embodiment, and FIG. 5 is a block diagram that illustrates an example calibration device for use in calibrating an ocular prosthesis, according to an embodiment.

In the illustrated embodiment, the calibration device 400 is a supporting external auxiliary device for the ocular prosthetic system 100. As seen in FIG. 4, the calibration device 400 includes a housing 402, which can be in the form of a pair of glasses or table-mounted, adjustable eye examination unit, among others. While the calibration device 400 shown in FIG. 4 only depicts a sensing of the orbital implant, it should be noted that the calibration device 400 can serially or simultaneously also sense the movement of the other eye of the subject (e.g., in order to help calibrate the display of the ocular prosthesis by determining the motility of the subject's other eye) in order to match the motion of the display of the ocular prosthesis 110 to the motion of the subject's other eye, whether it is also a prosthesis or not. As shown in FIG. 4, the calibration device 400 sends light 404 and receives light 406 (or simply receives ambient light reflecting off) from the orbital implant 120 in order to sense the motion of the orbital implant 120 for calibration purposes. This procedure may also be performed with the ocular prosthesis 110 in the inserted state for calibration, in some embodiments. Such a measurement with the ocular prosthesis 110 in the inserted state can also be used in conjunction with the measurements in the non-inserted state, in order to account for any motion of the ocular prosthesis 110 within the closed loop of the prosthesis space in front of the orbital implant when determining the proper calibration of the display.

The calibration device 400 provides a way to measure the movement of the unaffected eye (the movement in all directions), and also provides a way to detect the color of the normal eye of the subject and the response of the pupil to light, and take this information and use this to direct the display of the ocular prosthesis 110 in order to program the controllers of the display device on how to have the image appear to "behave."

As shown in FIG. 5, an embodiment of the calibration device includes a processor 501, one or more scanners 503, for example to detect motion (e.g., direction of the motion, speed of the motion, acceleration of the motion), color, and other features of the normal eye or the eye being fitted with a prosthesis (e.g. a pupil velocity meter), a data storage device 505 for storage of measurement data, and other configuration data, and a user interface 507 to allow an operator (such as the doctor or technician) to control the operation of the calibration device and processing of the measurements taken. The illustrated embodiment of the calibration device 400 also includes a communication device 513 that is configured to wirelessly (or via wires) communicate with the communication module 313 of the ocular prosthesis 110 in order to provide calibration information, including factors to correct the orientation, motion and other appearance shown by the ocular prosthesis 110. In some embodiments, the calibration device 400 also includes a charging station 512 that is configured to wirelessly (or via wires) provide power to the power source 302 on the ocular prosthesis 110.

For example, the following non-limiting, example of a calibration procedure is followed in some embodiments once the implant/prosthesis is fitted. For example, a picture of the eye before removal or of the subject's other eye (e.g., if the subject's other eye is healthy) can be scanned for color (high resolution digital image). Also, in some embodiments, a movement calibration is performed in order to measure one eye against the other by instructing the subject to look in a range of directions. For example, the subject is instructed to look as far left as possible and the degrees from center are measured for the unaffected eye, and measured for the orbital implant or the eye image (or some calibration point) on the ocular prosthesis. Measurement data of such movements is recorded by the calibration device 400, and communicated to the ocular prosthesis 110 through communication module 313. The processor 301 in the ocular prosthesis 110 is then programmed to compensate so that the image on the display will act in the same manner as the unaffected eye. For example, if the marker on the orbital implant can only be shifted five degrees to the left by muscle movement, but the normal eye can look thirty degrees to the left, then the calibration algorithm will indicate that this five degrees of movement scales so that the image appears to move thirty degrees. In some embodiments, the calibration device is worn like a pair of glasses that measures the unaffected eye movement and response as a standard, and then directs the processor in the ocular prosthesis. In some embodiments, the movements can be measured using the calibration device with the ocular prosthesis 110 in the inserted state. The ocular prosthesis is then removed (to the non-inserted state) and connected to the calibration unit in order to synchronize the calibration measurements with the processor of the ocular prosthesis.

In various embodiments, software executing on a processor is utilized to implement embedded controls for the hardware on the ocular prosthesis, as well as for the various control systems for motion control of the eye. In some embodiments, fuzzy logic is used for designing a realistic pupil response to incident light. In various embodiments, microprocessor programming is written utilizing a Hi-Tech C compiler along with a MPLAB suite of tools from the Microchip Corporation line of microcontrollers. In various embodiments, the microcontroller is an 8 bit 4MIPS unit, or a 16 bit MIPS for increased performance, among others, or some combination.

In some embodiments, the ocular prosthetic system is configured to provide a computerized image of an iris with realistic conjunctival blood vessels, which moves like a human eye, is colored to match a human eye, and responds to ambient light levels. In some embodiments the display device is a screen mounted into a molded methylmethracylate prosthesis with a form factor suited for insertion under the subject's eyelid and adjacent and anterior to the surgically implanted orbital implant. These prostheses can be molded, for example, utilizing dental prosthodontic techniques. A mold of the subject's anophthalmic socket (socket without an eye) is made, in some embodiments, utilizing alginate; and, the mold is transferred into plastic.

The ocular prosthesis itself (with embedded display device) is configured to respond to movement of the surgically implanted orbital implant on or into which zero or more markers have been placed. In some embodiments, motion sensing technology is utilized to detect the movement of the marker(s), and the ocular prosthesis is individually programmed so that horizontal movement of the embedded marker translates into horizontal movement of the image on the display device disposed within the ocular prosthesis, and similarly vertical movement detected in the implant translates into vertical movement of the image on the display device.

Various embodiments of the invention provide a miniaturized, functional, multicolor, embedded, powered electronic or mechanical prosthesis and equipment that can convert movement of the embedded implant into life like movement of the image displayed by the prosthesis.

Enucleation is generally the surgical removal of the entire eye but leaving the six extraocular muscles and part of the optic nerve. As discussed above and shown in FIG. 1, the ocular prosthetic system can be utilized by a subject that has undergone surgical enucleation.

Figure 6A:
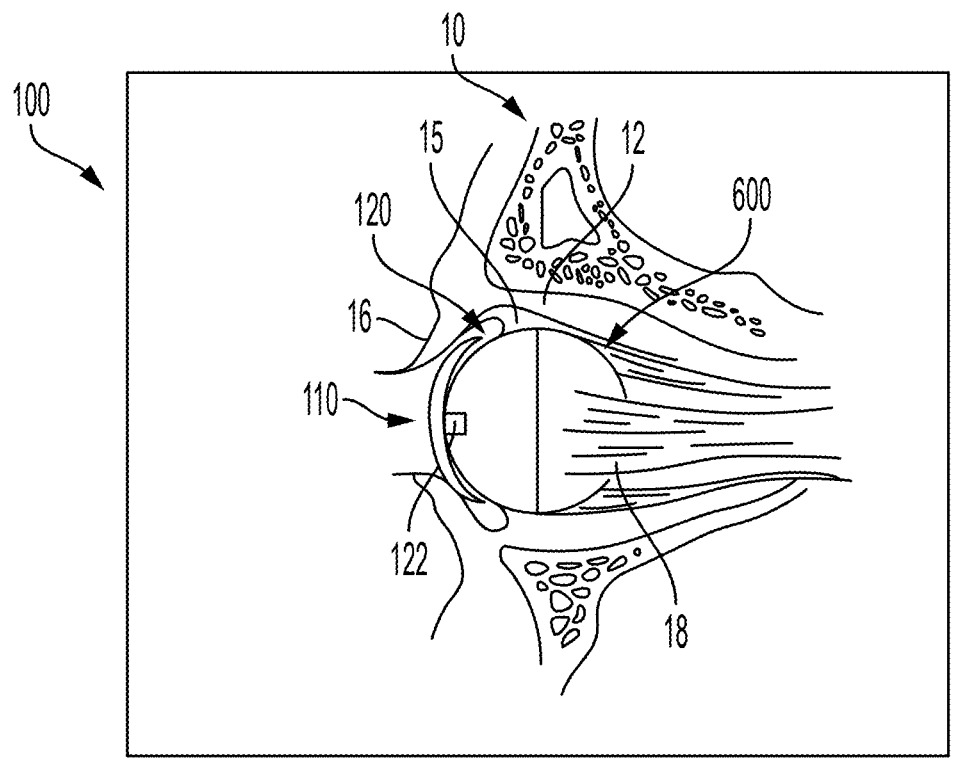
FIG. 6A is a block diagram that illustrates an example ocular prosthetic system that includes an ocular prosthesis and an orbital implant utilized by a patient that has undergone evisceration, where the ocular prosthesis is shown in an inserted state adjacent and anterior to the orbital implant, according to an embodiment.

Additionally, the ocular prosthetic system can be used after a technique called "evisceration." An evisceration is a surgical procedure by which only partial removal of the eye is performed (e.g., such a procedure can be performed after trauma to the eye). The front half of the eye is removed and the contents inside the eye removed but the sclera, muscles and optic nerve (and supplying blood vessels) are left. In this situation, in some embodiments, an orbital implant is then placed into the remaining half of the eye, and the ocular prosthesis used therewith. FIG. 6A is block diagram that illustrates an example ocular prosthetic system that includes an ocular prosthesis and an orbital implant utilized by a subject that has undergone evisceration, where the ocular prosthesis 110 is shown in an inserted state adjacent and anterior to the orbital implant 120, according to an embodiment. The orbital implant 120 is surgically inserted within the remaining half of the eye 600. In this situation, the muscles 18 around the eye (six of them) typically remain connected to the remaining half of the eye 600.

In some embodiments, the ocular prosthetic system is available in several sizes to account for all size variations of subjects (infants through adults). This enables a practitioner to continue to provide a properly sized prosthesis to mimic natural volume, while allowing the computerization to account for movement, esthetics, and pupil dilatation.

In a further alternative embodiment, velocity and/or acceleration sensors are included in the implant detector 309. For example, one or more velocity and/or acceleration sensors are provided in the ocular prosthesis 110, and one or more velocity and/or acceleration transducers are provided in the orbital implant 120 in order to allow the ocular prosthesis 110 to detect and emulate the intended, lifelike motion of the eye using scaling factors based on calibration measurements. In various embodiments, the velocity/acceleration sensors or portions thereof are put into the orbital implant and/or ocular prosthesis to sense movement of the orbital implant and/or ocular prosthesis, and the ocular prosthesis 110 receives and utilizes this data to display life-life motion of an eye. For example, an embodiment includes such a sensor in both the orbital implant and the ocular prosthesis, and the ocular prosthesis uses output signals from both such sensors to cancel out any outside movement of the body of the person and only use relative movement between the orbital implant and ocular prosthesis to move the eye display. In some such embodiments, the output signal is wirelessly transmitted from the orbital implant by a transmitter therein to a receiver in the ocular prosthesis.

Figure 6B:
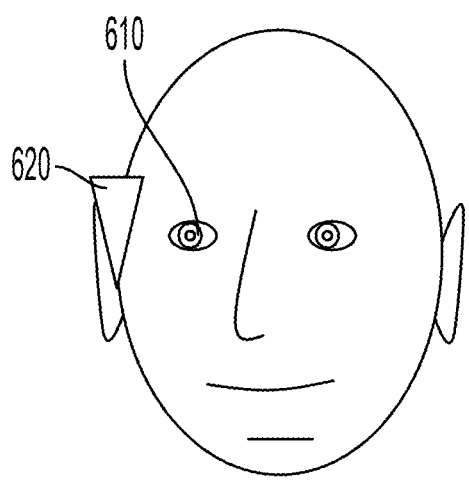
FIG. 6B and FIG. 6C are block diagrams that illustrate example various ocular prosthesis systems, each with an external wearable device that is configured to perform one or more functions for the ocular prosthesis, according to some embodiments.
Figure 6C:
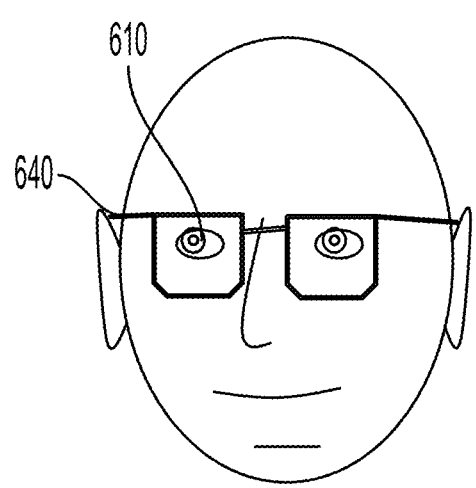

FIG. 6B and FIG. 6C are block diagrams that illustrate example various ocular prosthesis systems, each with an external wearable device 620 or 640 that is configured to perform one or more functions for the ocular prosthesis 610, according to some embodiments. For example, in various embodiments, an earpiece device 620 resting on an ear, e.g., an ear closest to the ocular prosthesis 610, or a portion 640 of a frame of a pair of glasses closest to the ocular prosthesis 610, houses one or more components that augment or replace components depicted in FIG. 3A for the ocular prosthesis 110 or one or more components of the calibration device 400 depicted in FIG. 5, or some combination. Power and information are transferred to the ocular prosthesis 610 through one or more wired or wireless means, e.g., one or more tiny skin colored wires or one or more antenna and induction coils.

Although processes, equipment, and data structures are depicted in FIG. 3A, FIG. 3B, FIG. 5, FIG. 6B and FIG. 6C, as integral blocks in a particular arrangement for purposes of illustration, in other embodiments one or more processes, equipment or data structures, or portions thereof, are arranged in a different manner, on the same or different hosts, in one or more databases, or are omitted, or one or more different processes or data structures are included on the same or different hosts. For example, a processor in earpiece 620 or frame portion 640 includes one or more processors or power sources or memory to replace or assist the functions of those components in FIG. 3A and FIG. 5.

FIG. 7 is a flow diagram that illustrates an example method 700 for operating an ocular prosthesis with a display device, according to an embodiment. Although steps are depicted in FIG. 7, and in subsequent flowchart FIG. 8, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 701, one or more implant markers are attached to move with an orbital implant. For example, as described above, in various embodiments, a hole is drilled in an implant, either before or after the orbital implant is surgically attached to one or more optic muscles 18, and a marker, such as a magnet or light emitting diode is inserted in the hole and sealed in. In other embodiments, the marker, such as one or more tattoos or one or more foils for a variable capacitor, as described in more detail below, are attached to an outside of the orbital implant and sealed in place. The conjunctiva may then subsequently form over the seal. In some embodiments, no marker is required, and step 701 is omitted.

In some embodiments, during step 701, the marker is attached to the conjunctiva that moves more or less with the orbital implant; but, the marker is not directly attached to the implant. In some of these embodiments, as described in more detail below, step 701 includes inserting the one or more markers into a tube of biologically inert material, such as silicone or some type of plastic, either before or after one end of the tube has been closed, e.g., by crimping or heat. Then the remaining end or ends of the tube are closed and the tube with enclosed ends is sutured to the conjunctiva or scar-conjunctiva complex that forms over the orbital implant. Such placement of the implant marker is especially suitable for retro fitting an implant already surgically attached, or replacing markers after their useful lifetime. This and other alternatives for the marker, such as a paddle marker, are described in more detail below with reference to FIG. 11E through FIG. 11J.

In step 703, the power source on the ocular prosthesis is charged or configuration data is sent to the processor/memory in the ocular prosthesis, or both. In some embodiments, step 703 is performed before step 705, while the ocular prosthesis 110 is in a non-inserted stated, as depicted in FIG. 1. For example, in some embodiments, the ocular prosthesis is placed in a charging station for a suitable period of time. In some embodiments, step 703 is performed after step 705, while the ocular prosthesis 110 is in an inserted state, as depicted in FIG. 2. For example, the calibration device 400 or earpiece 620 or glasses frame portion 640 emits an electromagnetic wave that produces a current in an induction coil in a charge receiving device 305 of the power source 302, as well as in an antenna of the communications module 313. In some embodiments, contacts on a surface of the ocular prosthesis are connected by wires to a charging station, such as calibration device 400, earpiece 620 or glasses frame portion 640, or some combination, during step 703.

In some embodiments, configuration data comprises an image or a compressed image of a natural eye for the subject, or some combination. In some embodiments, the configuration data includes values for various parameters, such as a size for the iris, a color selected from a limited color palette, or a particular combination of a limited color palette, a size range for a pupil, a rate of change for a pupil, and scaling factors for transforming detected motion of the orbital implant into natural motion (e.g., angular range and speed and or acceleration) of the iris. In some embodiments, configuration data includes values for parameters used by the implant detector, such as spacing associated with photodiodes and light intensity calibration data. In some embodiments, configuration data includes software instructions to cause the processor to perform one or more functions, and calibration data for one or more other sensors, such as ambient light sensor or accelerometer or sensor to determine orientation in gravity field. Further detailed examples of configuration data are described below in the context of one or more embodiments with various display devices and implant detectors.

In some embodiments, step 703 includes operating the calibration device 400 to determine one or more properties of the image or scaling factors, as described in more detail below with reference to FIG. 8. For example, during an initialization phase, the calibration device 400 is operated to observe the other eye of the subject, either alone or in concert with a marker on the orbital implant or ocular prosthesis, to determine initial scaling factors, properties of the appearance of the other eye or some combination. In some embodiments, step 703 includes communicating software instruction upgrades for the processor 301 in the ocular prosthesis 110.

In step 705, the ocular prosthesis is inserted into the prosthesis space under the eyelids and anterior to the orbital implant. When inserted into the prosthesis space, the ocular prosthesis is herein described to be "adjacent" to the orbital implant. However the prosthesis may or may not be in contact with the orbital implant or the conjunctiva or scar-conjunctiva complex. However, when adjacent to the orbital implant, an implant detector disposed in the ocular prosthesis, in some embodiments, is within range to detect the orbital implant or any marker that moves with the orbital implant.

The following steps from step 711 through step 721 are performed, in various embodiments by the ocular prosthesis acting alone, or in combination with an external wearable device, such as earpiece 620 or glasses frame portion 640, or some combination.

In step 711, the configuration data sent in step 703 is received. The configuration data is configured to indicate one or more properties for rendering a natural appearance for an eyeball on the display device 311 disposed in the ocular prosthesis. Example configuration data are described above with reference to step 703.

In step 713, the position or movement of the orbital implant, or other eye, is detected. In several illustrated embodiments described below, different implant detectors are described. In some embodiments, step 713 includes detecting orientation or motion of natural or other eye, e.g., using one or more sensors disposed in earpiece 620 or glasses frame portion 640, or some combination. In some embodiments, absolute orientation is not utilized, and only changes in orientation or rate of change of orientation are detected during step 713. In some embodiments, step 713 involves detecting one or more markers. In some embodiments, step 713 involves detecting mechanical sliding of conjunctiva past the ocular prosthesis, such as used in an optical computer mouse pointing device, without a marker attached to the implant. In some embodiments, step 713 includes activating the marker 122 that moves with the orbital implant, or powering the marker 122, or some combination, as described in more detail below with regard to a particular embodiment. Thus, during step 713, a change is determined in orientation of an orbital implant in a subject.

In step 715, the ambient light detected on an anterior surface of the ocular prosthesis is determined. For example, based on output from light sensor 307, the ambient light level in the neighborhood of the prosthesis is determined and provided as a specific value of the light intensity or a code representing same. In some embodiments, the light sensor 307 is omitted and step 715 is likewise omitted.

In step 717, an update is determined for the natural appearance of a visible portion of an eyeball for the subject based on the position or movement of the orbital implant or ambient light or some combination. For example, movement of the center of the iris is determined both horizontally and vertically based on the change or movement in the orientation of the orbital implant and change in size of the pupil is determined based on the ambient light level. Thus, in step 715, an update is determined to a natural appearance for a visible portion of an eyeball for the subject based on the change in orientation of the orbital implant.

In step 719, the natural appearance of the visible portion of the eyeball of the subject is rendered on the display device 311. Any method known in the art to render an image may be used. As described in more detail below, the display device is configured with a certain number of pixels in the horizontal and vertical dimensions and with a certain refresh rate. For example, instructions and power are sent to operate various pixels of the display device 311 as described in more detail below. Only the pixels that are affected by the change determined in step 717 over a time interval corresponding to the refresh rate are updated in some embodiments. In some embodiments, a new image is determined entirely at the refresh rate. In other embodiments, based on the previous image and the changes in position of the orbital implant or ambient light, only pixels that are affected by the change are updated. In some embodiments, such as embodiments using the Motion Picture Engineering Group (MPEG) protocol, panels of the image that are affected by the change and the changes to those panels are determined and rendered on the display device 311. Thus step 719 includes rendering an update to an image of the natural appearance for a display device disposed in an ocular prosthesis configured to be inserted in the subject anterior to the orbital implant.

Various efficiencies are implemented in various embodiments. For example, as described in more detail below, in some embodiments, only a few bits are utilized to represent the color at each pixel based on a reduced color palette. In some embodiments, the reduced color palette refers only to colors enabled to render the appearance of the eye of a particular subject. In some embodiments, the reduced color palette refers to colors enabled to render the appearance of the eye of a limited population of subjects, such as brown eyed subjects or blue-eyed subjects. In some embodiments, the reduced color palette refers to colors enabled to render the appearance of all possible subjects. Even so, the number of colors in the palette is substantially less than the number of colors used in photographic imagery because many colors are just not found among the iris colors of the population of subjects.

In step 721, the various components disposed in the ocular prosthesis are operated to conserve power. In general, step 721 is performed simultaneously with step 713 through step 719. For example, in some embodiments, display device 311 is a reflective display device that requires little power to retain an image and consumes power only when the value at a pixel is changed in an amount that depends on the number of pixels changed. In such embodiments, the circuits that power each pixel are deactivated between refresh events.

In some embodiments, the following steps from step 723 through step 733 are performed by an operator of the ocular prosthesis system, such as the subject, a care giver, a technician or a practitioner.

In step 723, it is determined whether a wear cycle has ended. If not, then control returns to step 713 and following steps to determining an updated position of the orbital implant 120 or other eye and updating the display device 311. In some embodiments, it is determined from recent orientations of the orbital implant or other eye, that the orbital implant or other eye is not moving; and, the time to cycle through steps 713 and following is extended. In some of these embodiments, when it is determined that the orbital implant or other eye is moving, the time to cycle through step 713 and following is decreased based on the rate of movement of the orbital implant or other eye down to the shortest time associated with the refresh rate of the display device 311.

If it is determined in step 723 that they wear cycle has ended, then in step 731 the ocular prosthesis is removed from the subject's eye, e.g. is removed from the prosthesis space behind the subject's eyelids and in front of the orbital implant. In some embodiments, the subject determines that the wear cycle has ended, e.g. at the end of the day, and the subject removes the ocular prosthesis. In some embodiments, depletion of power from the power source determines that the wear cycle has ended; and, the subject is alerted to remove the ocular prosthesis, e.g., by an audible sound or a vibration.

In step 733, it is determined whether the ocular prosthesis should be recharged or recalibrated. If not, the process ends. If so, then control passes back to step 703 to recharge the power source or send new configuration data, or some combination.

FIG. 8 is a flow diagram that illustrates an example method 800 for externally calibrating and charging an ocular prosthesis with a display device, according to an embodiment. In step 801, the appearance of the ocular prosthesis and the appearance of the other eye (natural or not) are observed simultaneously, e.g. using the calibration device 400 or similar components in earpiece 620 or glasses frames 640. In some embodiments, in step 801, movement of the orbital implant is detected along with, or in place of, the appearance of the ocular prosthesis. For example, in some embodiments, digital video is collected from each eye while the subject executes one or more movements for calibration purposes, such as rolling eyes left and right as well as up-and-down to the maximum extent possible.

In step 803, difference in appearances of the ocular prosthesis and the other eye are determined. In some embodiments, step 803 includes determining a difference between movement of the orbital implant and the other eye in addition to or instead of determining the difference from the appearance of the ocular prosthesis. For example, the digital video of each eye collected during step 801 are registered to each other, e.g. by the center of the pupil, and two dimensional correlation coefficients are determined as a function of time.

In step 805, a first factor is determined. The first factor relates movement of an image of an eyeball on display device 311 of the ocular prosthesis to the detected movement of the orbital implant 120. The movement of the orbital implant 120 can be detected directly by the calibration device 400, or indirectly through movement of the image on the display device 311 of the ocular prosthesis 110. In some embodiments, the first factor is a vector of values representing different directions or rates of change, or some combination. For example, in some embodiments the values of the vector of the first factor are determined such that the two dimensional correlation coefficients of the scaled video of the image of the ocular prosthesis with the video of the other eye are maximized.

In step 807, a second factor is determined. The second factor relates a change in a size of the pupil to the change in amount of detected ambient light. The change in amount of detected ambient light can be detected directly by the calibration device 400, or indirectly through communication of the output of the ambient light sensor 307 from the ocular prosthesis 110 or size of the pupil on the display device 311 of the ocular prosthesis 110. In some embodiments, the second factor is a vector of values representing different light levels or rates of change, or some combination.

In step 809, the first and second factors are communicated as part of the configuration data transmitted by communication module 513 to the ocular prosthesis 110, as received during step 711, described above. As also described above, in some embodiments the configuration data transmitted by communication module 513 during step 809 also includes one or more properties of the natural appearance of a visible portion of an eyeball of the subject, such as iris size and color, pupil size and range of sizes, and position or density of blood vessels apparent on the sclera. In some embodiments, the configuration data includes software instructions for the processor 301 on the ocular prosthesis 110.

In step 811, a power source for the ocular prosthesis or for the orbital implant or both is charged. For example, an antenna or coil in charging station 512 of calibration device 400, or equivalent components in earpiece 620 or glasses frame portion 640, wirelessly induces a current in an induction coil in the ocular prosthesis, or orbital implant, or marker 122 that moves with the orbital implant 120, or some combination. In some embodiments, the charging station 512, or equivalent components in earpiece 620 or glasses frame portion 640, is connected by wires to contacts on the ocular prosthesis 110 or orbital implant 120 or marker 122 that moves with the orbital implant 120, or some combination. A power source for the charging station 512, or equivalent components in earpiece 620 or glasses frame portion 640, is engage to transmit power to the device being charged.

In step 821, it is determined whether conditions are satisfied to recalibrate the ocular prosthesis 110. For example, in some embodiments, the conditions to recalibrate include the current time reaching a particular scheduled date for recalibration, or notification that an update to software is available, or replacement of the ocular prosthesis 110, or receiving error messages from the ocular prosthesis during step 809, or upon the recommendation for recalibration from a practitioner or technician who has examined the operation of the ocular prosthesis in the subject, among others, or some combination. If conditions are satisfied for recalibration, then control passes back to step 801 and following steps. If not, control passes to step 823.

In step 823, it is determined whether conditions are satisfied to recharge the ocular prosthesis 110. If so, then control passes back to step 811. If not, then the process ends.

Using the methods 700 and 800, or portions thereof, with ocular prosthesis 110 and calibration device 400, respectively, it is possible to accurately scale movement of an image of an eye to match the movement of a natural eye of a subject. Orbital implant motion is calibrated, compensating for any physiological movement limitations as a result of the surgery that attached the orbital implant 120 to the eye muscles 18. A digital image of an iris is determined with realistic conjunctival blood vessels, which is color matched to the human eye, and which accurately moves like a human eye with a realistic and dynamic response to ambient light.

2. Example Embodiments

In this section, various specific embodiments of one or more components of the ocular prosthesis system are described, along with results of one or more experimental embodiments.

2.1 Display Device

In the following example embodiments, ranges of display size, resolution, and refresh rate are determined that provide a natural appearance of a visible portion of an eyeball on a flexible display bent into horizontally curved surface that occupies space and consumes power at a reasonable rate for the ocular prosthesis 110.

Figure 9A:
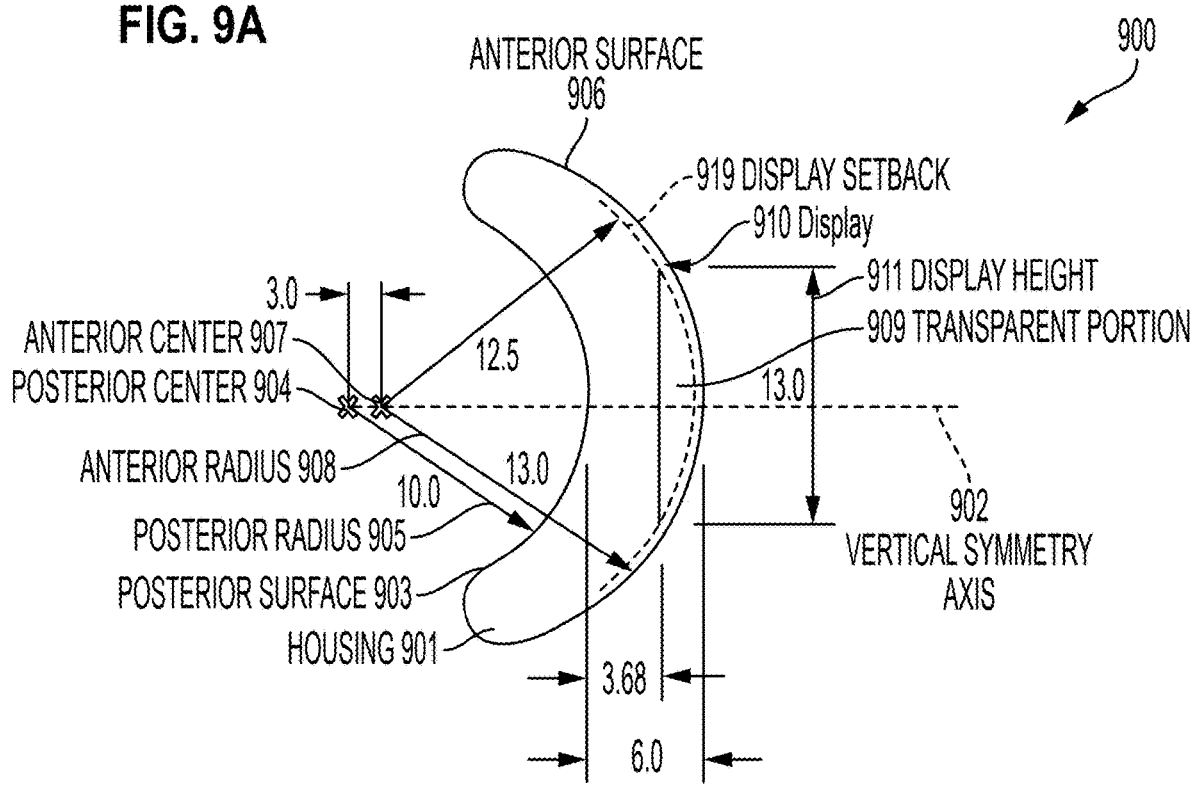
FIG. 9A and FIG. 9B are block diagrams that illustrate an example display device disposed in a housing having a form factor for an ocular prosthesis, according to an embodiment.
Figure 9B:
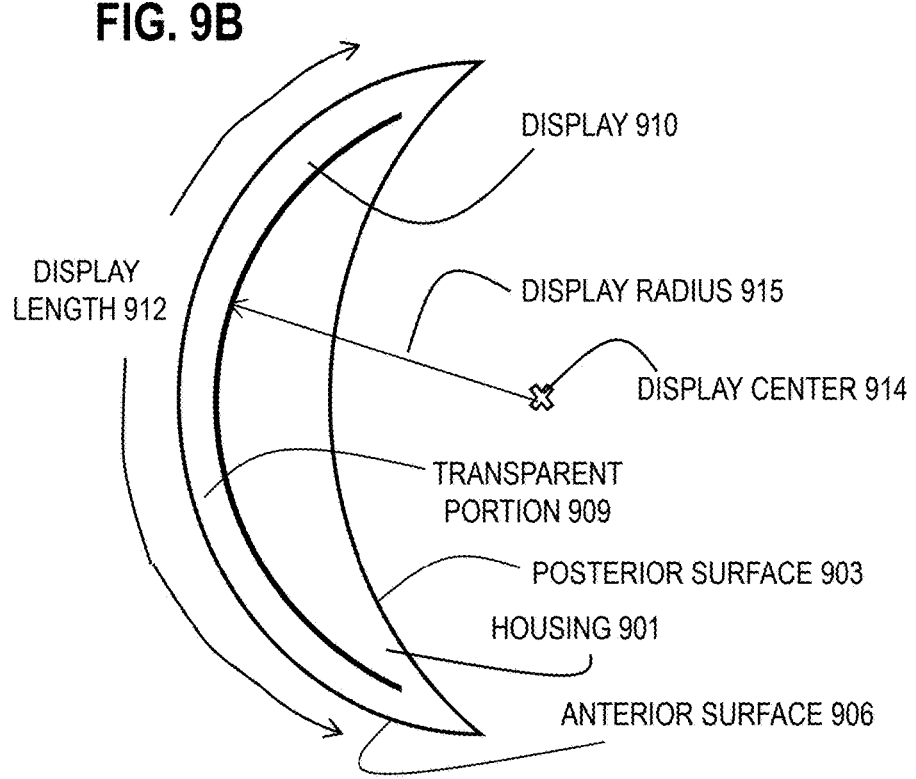

FIG. 9A and FIG. 9B are block diagrams that illustrate an example display device disposed in a housing having a form factor for an ocular prosthesis, according to an embodiment. According to the illustrated embodiment, the ocular prosthesis comprises a housing 901 with a form factor suited for insertion in the prosthesis space behind the eyelid and anterior to the orbital implant. FIG. 9A is a block diagram that illustrates an example vertical cross-section through the housing 901. The posterior surface 903 of the housing 901 has a posterior radius of curvature 905 of about 10 millimeters (mm, 1 mm=$10^{-3}$ meters) around a posterior center 904. The anterior surface 906 of the housing 901 has an anterior radius of curvature 908 of about 13 mm around an anterior center 907 displaced 3 mm forward of the posterior center 904. The housing 901 is vertically symmetric about a vertical symmetry axis 902.

In the vertical cross-section of FIG. 9A, the display device 910 is not curved, is about 13 mm high, and is set back from the anterior surface of the housing 901 by a display setback 919 of about 0.5 mm. Thus the display 910 has a display height 911 of about 13 mm. Combined with the other dimensions already cited, this places the display 910 about 3.68 mm in front of the posterior surface 903, and the anterior surface 906 about 6 mm in front of the anterior surface 903, along the vertical symmetry axis 902. In order that the display 910 is visible at the anterior surface of the ocular prosthesis, at least a transparent portion 909 of the housing 901 is transparent to light. In some embodiments, one or more lenses are disposed in the transparent portion 909 in order to give the appearance of curvature in the vertical. In the horizontal cross-section of FIG. 9B along the vertical symmetry axis 902, the display device 910 is curved, with a display radius of curvature 915 and a display center 914. The display length 912 is about 26 mm. The display 910 is separated from the posterior surface 903 of the housing 901 by about 3.68 mm as depicted in FIG. 9A. Between the display 910 and the anterior surface 906 of housing 901 is transparent portion 909 of housing 901. In some embodiments, the centers and radii of curvature of the anterior surface 906 and the posterior surface 903 in the horizontal cross-section are the same as in the vertical cross-section.

Both emissive and reflective displays can be fabricated with the size and shape of display 910, as described in more detail below. In various embodiments, the display area of the ocular prosthesis for a normal adult ranges from about 24 mm length to about 26 mm length and from about 12 mm height to about 18 mm height. In various embodiments, a range of display areas of the ocular prosthesis for a child or small adult is selected from a set that is about two thirds or more of the size for a normal adult. In some embodiments, memory-in-pixel and an LCD over reflective backing layer is used to produce an excellent color display with very low power while the display is static, yet capable of video rate updates.

FIG. 9C is block diagram that illustrates an example image 920 for rendering on a display device 910, according to an embodiment. The image has an image length 922 that is greater than the display length 912, and an image height 921 that is greater than the display height 911. For example, in some embodiments, the image height 921 is twice the display height 911 and the image length 922 is twice the display length 912, so the image area is quadruple the display area 913.

The image 920 is made up of a background 923 that represents the sclera with one or more conjunctival blood vessels 924. The image 920 also includes an iris 925 and a variable sized pupil 926 centered on image center 927. Movement of an eye is represented by movement of the image 920 relative to the display area 913. As the eye is to be displayed moving up, the image 920 scrolls up relative to the display area 913, thus bringing the lower portions of the image 920 into the display area 913 and moving a portion of the image 920 above the iris 925 off the display area 913. The opposite occurs when the eye moves down. Similarly, as the eye is to be displayed moving left with respect to a person looking at the subject, the image 920 scrolls left relative to the display area 913, thus bringing the right portion of the image 920 into the display area 913 and moving a portion of the image 920 left of the iris 925 off the display area 913. In some embodiments, the area of image 920 is the same as the display area 913; and, as a row or column of pixels scrolls off one end of the display area 913, it appears along a corresponding row or column, respectively, on the opposite side of the display area 913. In some embodiments, the background is fixed and pixels that constitute the background are not moved as the eye is displayed to be moving. In these embodiments, only the iris 925 and the pupil 926 move across the display area 913.

FIG. 9D is a block diagram that illustrates an example image control screen 960 for controlling properties of the image and image changes over time to determine acceptable display properties, according to an embodiment. The screen includes one or more active areas that allow a user to input data to operate on data. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 9D as integral blocks in a particular arrangement on particular screen for purposes of illustration, in other embodiments, one or more screens, windows or active areas, or portions thereof, are arranged in a different order, are of different types, or one or more are omitted, or additional areas are included or the user interfaces are changed in some combination of ways.

In one portion of screen 960 is a representation of a display area 913 of display 910, e.g., 13 mm high by 26 mm long. Active area 930 is a pull down menu that allows selection of a frame refresh rate, e.g., 22 frames per second as depicted in active area 930. Active area 932 allows selection of contrast for the image presented in display area 913. Similarly, active area 934 allows selection of brightness for the image presented the display area 913; and, active area 936 allows selection of resolution, in pixels per inch (PPI), for the image presented in the display area 913. The example values of contrast brightness and resolution depicted in FIG. 9D are −3, −3 and 166, respectively, which represents moderate contrast and brightness and high resolution. It is expected that fewer pixels per inch will provide realistic representations of a visible portion of an eyeball of a subject and provide the advantage of fewer array elements, less power consumption, faster computations and better response.

Active area 938 allows selection of the number of bits used to represent each color at a pixel. The more bits used to represent a color at each pixel, the more memory and processing time is required to generate the portion of the image on the display area 913. The example value of a 16-bit bit depth allows a representation of 65,536 different colors and is expected to be greater than needed for realistic representations of a visible portion of an eyeball of a subject. Active area 940 is a button that causes the display area 913 to present an eye that appears to rotate to the viewer's left. Similarly, active area 942 is a button that causes the display area 913 to present an eye that appears to rotate to the viewer's right. Active area 944 is a button that allows a user to load a file of recorded natural movement, which can be played in display area 913 with different settings for brightness resolution bit depth etc. so one can determine which settings produce a natural appearance. Active area 946 allows a user to manipulate the direction of the iris in the display area 913 by moving a pointing device, such as a mouse.

Screen area 950 includes three buttons for controlling the display area by clearing the image, turning off the display area or turning on the display area, respectively. Screen area 952 includes two buttons for controlling which image is presented in the display area 913. One button allows a user to reset an image to its original orientation, and the second button allows a user to download a particular image from storage.

By operating the active elements of screen 960 in view of several practitioners, a range of image properties that provide acceptably natural and realistic appearance and movement of an eye of a subject was determined.

In an experimental embodiment, an active-matrix organic light-emitting diode (AMOLED) development system was procured and a Windows application was created to display a representative eye image on the display, as depicted in FIG. 9D. Image procession algorithms were created in MATLAB™ from MATHWORKS™ of Natlick, Massachusetts to render the image in the most accurate form and save it to a Joint Photographic Experts Group (JPEG) file. A MATLAB™ algorithm was also developed to create a real-time movie using eye kinematic data supplied by the Memorial Sloan Kettering Cancer Center (MSKCC) of New York, New York. This program produced an Audio Video Interleave (AVI) formatted movie file representing typical eye motions that may be encountered by the ocular prosthetic system in normal use. The movie was played back multiple times for the viewers while the display parameters (refresh rate, color depth, contrast and resolution) were varied. The minimal parameter values that yielded aesthetically acceptable (also called herein "realistic" or "natural") results were determined by a subjective judging panel assembled by MSKCC. The demonstrator was presented at MSKCC where the visual output was judged by Applicants as the display parameters were adjusted. Some general conclusions are presented next.

Frame rate (how often the display is updated) was determined to be important. Applicants determined that the image quality improved with higher frame rates, up to the 22 frames/second (FPS) limit of the experimental display. However, fast movements (cycads) were determined to look better at a lower frame rate whereas smooth movements (pursuits) improved at higher frame rates. The eye motion file used for this demonstration emphasized the cycad motions and selecting a lower frame rate eliminated some of the more extreme jumps. Overall, 17 FPS was judged to be adequate, which corresponds to a refresh time of 59 milliseconds (ms, 1 ms=$10^{-3}$ seconds). Thus a display frame rate in a range from about 17 FPS (refresh time of about 59 ms) to about 22 FPS (refresh time of about 45 ms) is advantageous for natural appearance of eye movements. In some embodiments, a refresh time of about 67 ms (a frame rate of about 15 FPS) is used. Similar results are expected for other display device types (electronic reflective and mechanical). In some embodiments, 10 FPS is acceptable. Thus, in various embodiments a frame rate is selected in a range extending from about 10 FPS and above to about 22 FPS or more.

Resolution was also determined to be important. The AMOLED display had a resolution expressed as a dot pitch (reciprocal of pixel size) of 166 pixels per inch (PPI), which proved more than adequate for a good rendition of the image. Applicants determined resolution was adequate for a natural appearance until the simulated pixel size was increased to 50 PPI. Due to the way that this down-sampled image was created, the edges of the (larger) simulated pixels were softened, making a less blocky appearance than a display having physically large pixels. Thus a display resolution in a range from about 50 PPI to about 166 PPI provide a natural appearance of a visible portion of an eyeball of a subject. A more advantageous range of resolutions extends from about 60 PPI to about 80 PPI. Applicants have determined that a resolution of about 70 PPI (pixel size of about 0.36 mm) is even more advantageous because it provides an acceptable appearance and can be achieved with fewer pixels, which reduces complexity and power consumption over displays that have higher resolution, e.g., 80 PPI to about 166 PPI. Similar results are expected for other display device types (electronic reflective and mechanical).

At 70 PPI (pixel size of 0.36 mm), the 26 mm by 13 mm display area comprises an array of about 72×36 pixels (about 2592 pixels). In some embodiments, to achieve the advantage of efficiency in addressing pixel elements using binary arithmetic, the display area comprises 64 by 32 pixels (2048 pixels) for a display area of about 23 mm in length and about 11.5 mm in height at 70 PPI, or the originally stated display area of 26 mm by 13 mm with a resolution of about 62.5 PPI. Applicants also determined that acceptable appearance is achieved with a display area that is about 24 mm long and about 12 mm high. This smaller display area, used in some embodiments, offers the advantage of fewer components to realistically present an image of an eyeball of the subject or greater resolution for a display area comprising 64×32 pixels. Thus, in various embodiments, resolution is selected in a range extending from about 60 PPI and greater.

Unlike a reflective display (or the natural eye) the AMOLED display emits light. It was difficult to adjust color and contrast of the AMOLED display for a lifelike appearance as the lighting conditions in the room changed. In dim light it was found to be difficult to prevent the eye from glowing, which yields a robotic appearance that is unpleasant and undesirable. Making the "white" of the sclera look natural required careful adjustment of the color balance and this also varied with the room light. Overall, it was felt that a reflective display would provide a more natural image with less difficulty. Thus, Applicants determined that a reflective display device provides the advantage of more realistic appearance with simpler computations under varying ambient light conditions.

In various embodiments, display technologies include emissive display devices such as liquid crystal display (LCD) and AMOLED, and reflective display devices such as electro-phoretic (EP), electro-fluidic (EF) and electro-wetting (EW). LCD display technology and manufacturing methods are by far the most mature, but the multiple polarization and electrode layers require fabrication on a rigid structure which makes these displays thicker relative to the other less mature technologies. LCDs also require a backlight which further adds to the overall thickness and power requirements.

AMOLED display devices, used in the experimental embodiment described above, are a newer and less mature technology than LCDs. These displays are commercially available on a limited basis in select sizes in newer products. AMOLEDs emit light and do not need a backlight or polarization layer like an LCD. This not only makes these displays thinner and less power hungry than LCDs, it also makes it possible to produce AMOLEDs on a flexible substrate, thus making this technology suitable for the display 910. As described above, AMOLED displays share a common disadvantage with LCD backlights, that is, the ambient light condition would desirably be monitored closely and the brightness of the display adjusted so that it does not glow or appear to give off light. When the device battery becomes discharged, an AMOLED display will go dark resulting in an undesirable appearance.

Reflective electro-phoretic (EP) displays use charged colored pigment particles in a clear fluid medium to create images when these particles are attracted or repelled by capacitive elements on the face and substrate of the display. The pixel takes on the color of the pigmented particles that are forced to the top (visible) surface.

Reflective electro-fluidic (EF) display devices use a variable volume micro-electromechanical system (MEMS) chamber to draw-in or expel a dyed liquid medium to produce various shades of color. When the pixel chamber is expanded by electrostatic forces, the colored fluid flows into the visible chamber and the pixel becomes the color of the dye. When the pixel chamber contracts, most of the fluid is expelled and the pixel approximates the substrate color. The shade can be modulated by varying the volume of the chamber. In some embodiments, this is a two color system—arbitrary combo of one fluid color and one substrate color—and is adequate for some uses. In other embodiments, more than one fluid chamber can be included in each pixel for additional color layers and a full color system.

Reflective electro-wetting (EW) display devices use a voltage to modify the wetting properties of a solid material. A display using this principle creates an optical switch by contracting a colored oil film with a voltage applied to an electrode in contact with it. As with EF displays, the colored region of a pixel can be modulated to produce varying shades of the color. More than one fluid chamber can be included in each pixel.

These reflective displays are the newest and least mature display technologies; however, improvements in device performance are continually and rapidly being achieved. At the time of this writing the characteristics of reflective displays include: 1) material selection and fabrication methods are intrinsically linked; 2) at FUJIFILM™ DIMATIX™ of Santa Clara, California, 0.047 mm features are possible with a drop volume of 10 picoLiter (pL, 1 pL $=10^{-12}$ Liters); 3) at DIMATIX™ 0.023 mm features are possible with a 1 pL drop; 4) at NANOMAS TECHNOLOGIES™ of Vestal, New York, silver inks make possible 0.010 mm features. With features this small, several colors can be combined at each 0.360 mm pixel for full red-green-blue (RGB) or cyan-magenta-yellow-black (CMYK) spectrum of color combinations. Each color can be expressed at any degree of precision, but typically in 16 to 256 steps, using 4 bits to 8 bits, respectively, for each color.

In some embodiments, holographically formed polymer dispersed liquid crystals (HPDLC) are used.

Color palette and bit depth ranges are advantageously kept as small as possible to still provide realistic renderings of sclera, iris and pupil while reducing pixel circuitry complexity and computational loads. Clearly, a full color (CMYK) display (4×8 bits=32 bits) will satisfy the color gamut useful to reproduce a realistic eye image. But given the complexities of fabricating a flexible display and thin film transistor (TFT) backplane in the confined volume of this product, a significant advantage may be achieved by limiting the color gamut of the display used to produce a realistic rendering of the eye.

The color range of a typical eye can be an appreciable portion of the visual spectrum. A typical human sclera has surface vascular structures that appear as random red lines that are concentrated toward the peripheral regions. Hues of yellow, beige and blue are also common in the sclera thus giving the "white" of the eye a significant color spectrum especially when added to very different iris colors. The iris and pupil tend to have a narrower color spectrum than the sclera and are reproduced to an acceptable level with a two color system, assuming that the two colors were chosen to be near the mean hues of these features, in some embodiments. Such two color systems can be expressed in as little as 2×4=8 bits or as much as 2×8=16 bits, depending on the granularity of color changes supported.

A traditional prosthesis uses red threads to emulate the surface vascular structures of the sclera. It was observed under a 20× microscope that these red threads actually continue for some distance into the iris. Even though the iris was a light shade of blue, these threads were not visible to an unaided eye. Applicants determined that the color gamut of the display device could be reduced if the visible sclera and its fine red features were fabricated into the molded prosthetic package. Thus in some embodiments, the sclera image would be the background "color" of the display, apparent everywhere but in the region of the iris and pupil. The iris and pupil are adequately rendered, in some embodiments, using just a two color scheme, thus greatly reducing the complexity of the display, backplane and data processing. In at least some such embodiments, the two base colors for this two color display are specialized for a specific eye color group, for instance one pair of colors for rendering the iris of subjects with blue eyes and a second pair of colors for rendering the iris of subjects with brown eyes. In these embodiments, the sclera features are static as the iris and pupil image moves about the display area. It is anticipated that the effects of this will not be noticeable in normal use; and, thus, that the display will appear natural. In some such embodiments, displays incorporating different pigments are inventoried to create prostheses covering the wide range of individual eye coloration. Some degree of customization of the sclera background is also performed in some embodiments. Thus, in various embodiments, the color palette bit depth is selected in a range from about 8 bits to about 32 bits. In some embodiments, 16 bits are arranged as 5-5-6 for each of three colors, which provides a color depth of at least 5, a reasonably good color image if the palette is adjusted properly.

In some embodiments, creating a realistic eye image includes properly representing the changes which occur during pupil dilation/contraction. If the pupil were represented as a simple black dot that occludes either more or less of a fixed iris pattern, the result isn't very realistic as ambient light changes. This is because there are visible changes in the structure of the iris as the pupil changes size. In some embodiments, a much more realistic display is obtained using a physiologically accurate image of the eye for a range of possible dilation of the pupil. An algorithm is applied in some embodiments to smoothly transition from one image to another, e.g., using morphing techniques widely known in the art. This image is translated in response to position sensor information so that the eye appears to be gazing in the correct direction.

The reflective EP, EF and EW display devices share common characteristics and have significant advantages over AMOLED display devices. EP/EF/EW display device power usage is each lower than emissive display devices because power is consumed only when pixels are changing state. In contrast, for example, power in each AMOLED pixel is continually consumed while an image is presented. EP/EF/EW display devices are reflective display devices and do not emit light so ambient light sensing and complex corrections are not required to keep such display devices from appearing to glow under low light conditions. EP/EF/EW display device images are persistent and do not change after power is removed. This allows the display to have the appearance of a traditional eye prosthesis after battery discharge or device electronic failure. This makes a confidence alarm that issues when power reaches a critically low level less desirable for such displays and also makes carrying a back-up traditional prosthesis less desirable.

In some embodiments, degraded performance or failure of one or more components of the ocular prosthesis causes the subject to be alerted by a confidence alarm. For example, when power is about to be depleted for an emissive display device, the confidence alarm alerts the wearer when the battery has discharged to a predetermined level. Embodiments that do not employee a confidence alarm offer the advantage of removing the added size, power and complex computational load of the confidence alarm.

Whichever display technology is employed in various embodiments, it is advantageous that the display elements are fabricated on a flexible substrate so that the display can be fabricated flat using standard process and then curved onto a cylinder about a vertical axis. This will fit it to the curve of the eye (horizontally at least) while avoiding crinkling problems. It is noted that flexible is not stretchable, so conforming to a doubly curved surface (portion of a sphere) presents challenges to avoid display damage. Thus a cylindrical curved display is advantageous over a spherically curved display. PLASTIC LOGIC™ of Cambridge, United Kingdom fabricates flexible printable electronics. In an example method for assembling the display device, a display medium in sheet form is purchased from a manufacturer of a reflective display, such as a color electronic ink medium from E INK™ Corporation of Cambridge, Massachusetts (used in the well known KINDLE™ reader from AMAZON™ USA of Seattle, Washington) and mated to a flexible TFT backplane from a printable electronics fabrication facility, such as E3 DISPLAYS of Phoenix, Arizona Thus, in some embodiments, the display device is built on a flat, flexible substrate. As shown in FIG. 9A, Applicants have determined that there is sufficient internal volume to accommodate the display 910 with adequate room left over for the electronics (including communications module, processor and memory) and battery and sensor systems (including the implant detector and, in some embodiments, an ambient light sensor).

2.2 Power Source

Simulations were performed to determine the power demands of the display device and other systems disposed in the ocular prosthesis. It was then determined that the power demand could be satisfactorily met with a power source, including battery, that fits within the housing 901 for the ocular prosthesis. In some embodiments, a supercapacitor is used, even though the energy storage density (by volume) of the supercapacitor presently is much lower than for a lithium cell.

Applicants were able to extrapolate an electrical model for a display pixel and the associated TFT backplane, which is believed to be conservative. A usage model has been developed that approximates the number of pixel transitions over a given time. The switching speed of the display (refresh rate) is dependent on the drive voltage and consequently, the power consumed. For the display device modeled, there are 3380 addressable pixels and a refresh rate of 20 FPS (more than the 2592 pixels in a 26 mm by 13 mm display area at 70 PPI resolution and 17 FPS of an example embodiment, described above, capable of presenting an image of an eye with a natural appearance) and the sclera is represented by a fixed background.

A typical 12 mm diameter iris is comprised of approximately 1130 pixels. If the iris image were to move from one area of the display to a totally different area in a single frame, there would be a change of 2×1130=2260 pixels. A more reasonable estimate is about 20% of this number, e.g., about 452 pixels per frame. At 20 frames per second, the total activity is about 20×452=9040 pixels per second.

Each pixel is effectively modeled as a capacitor. Each pixel is approximated as a parallel plate capacitor with an area (A) of $(320 \mu m)^2 = 1.024 \times 10^{-7} m^2$, a plate separation (D) of 30 μm and a relative permittivity (εr, also called a "dielectric constant") of a medium value of 80. The plate area is fixed by the size of the pixels. Plate separation is estimated and the dielectric constant for water is used, which is an extremely high dielectric liquid. Capacitance, C, is given by Equation 1.

$$C = \varepsilon A/D = \varepsilon r \varepsilon 0 A/D \quad (1)$$

Where ε is specific permittivity and ε0 is permittivity of free space, equal to $8.85 \times 10^{-12}$ Farads per meter. Thus the capacitance per pixel is 2.4 picoFarads (pF, 1 pF=$10^{-12}$ Farads). The energy, E, used to charge a capacitor is given by Equation 2 in Watts per second (Joules) based on the voltage difference V between the two conducting plates of the capacitor.

$$E = V^2 C/2 \quad (2)$$

The display drive voltage is proportional to the desired frame rate. A manufacturer of electro-wetting (EW) display devices has characterized their technology as having a 20V drive voltage. It is estimated that a drive voltage at the pixel electrode of 10 V might be a better compromise between backplane transistor size, power consumption and display update time. The power calculations were performed for three sets of assumptions to show that power consumption is extremely low for even worst case conditions of drive voltage and capacitance. For V=drive voltage of 10 V, Equation 2 yields $120 \times 10^{-12}$ Joules per pixel. The power P is energy per unit time, t, and given by Equation 3.

$$P = E/t = E \times U \quad (3)$$

where U is the usage in pixels per unit time. For the usage model of 9040 pixels per second, the total display power is 1.08 microWatts (μW, 1 μW=$10^{-6}$ Watts). For V=drive voltage of 20 V, the total display power is 4.34 μW. For a worst case with quadruple the capacitance to 10 pF, 20 V driving voltage, and changing every pixel on every frame, the total display power is 135 μW.

In addition to the power consumed to change pixels, there is the power consumed by the backplane. The thin film transistor (TFT) backplane is the active circuitry that supplies power to the pixels to change their operating state. The operating model presented here is simplified but represents a conservative estimate of the TFT backplane power requirements. Assuming the backplane involves 3 transistors per pixel to achieve full color (fewer transistors are used for a two color system as proposed for some embodiments), the total number of TFTs for the 3380 pixels is 10,140. For a TFT backplane of conventional design, each of these transistors is driven (transitioned) once per frame, even if the display content is unchanged. It turns out that this constitutes the dominant power sink for the display. For an update rate of 20 FPS, the circuit load is 202,880 transitions per second.

Each TFT is estimated to have at most 5 pF gate-to-source capacitance. Driving this capacitance constitutes the primary energy dissipation factor in the backplane. The gate drive voltage is typically 5 V higher than the pixel voltage. For a 20 V pixel, the backplane energy per pixel is $1563 \times 10^{-12}$ Joules per transition. Therefore, the total backplane power consumption is 317 μW. For a 10 V pixel, the backplane power consumption is only 79 μW.

Figures 10A, 10B:
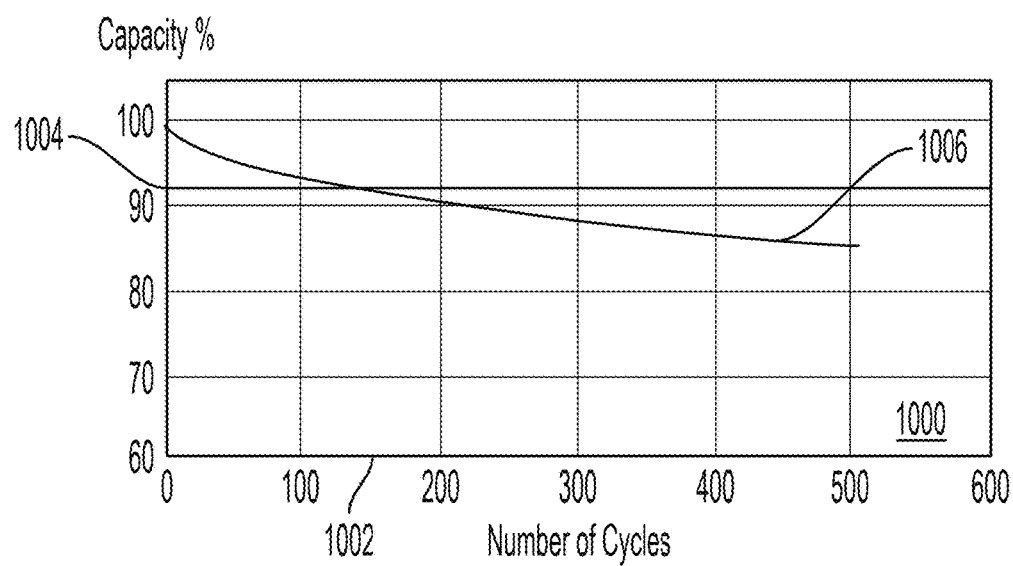
FIG. 10A is a table that illustrates example power consumption for an electronic display device suitable for an ocular prosthesis, according to various embodiments.
FIG. 10B is a graph that illustrates example recharge power for a battery suitable for an ocular prosthesis, according to an embodiment.

The total power consumption for the display and backplane is given in the table of FIG. 10A for several embodiments. FIG. 10A is a table that illustrates example power consumption for an electronic display device suitable for an ocular prosthesis, according to various embodiments. In FIG. 10A, the display devices' assumed properties for each embodiment are given in column 1012a. In this column, pixel is further abbreviated to "pel." Row 1014a is for an embodiment with 10 V driving voltage per pixel, and 20% of pixels updated each frame, and three TFTs per pixel. Row 1014b is for an embodiment with 20 V driving voltage per pixel, and 20% of pixels updated each frame, and three TFTs per pixel. Row 1014c is for an embodiment with 20 V driving voltage per pixel, and 100% of pixels updated each frame, and three TFTs per pixel. Column 1012b lists the display plane power consumption for each embodiment. Column 1012c lists the backplane power consumption for each embodiment, which far outweighs the display plane power consumption. Column 1012d lists the total display device power consumption for each embodiment. The values in microWatts are as recited above.

Given the power consumption rates of the example embodiments of the display device, the adequacy of storage battery properties appropriate to fit in the housing 901 of the ocular prosthesis can be evaluated. Several batteries with appropriate specifications are known to be commercially available. For example, at SOLICORE™ of Lakeland, Florida, lithium polymer batteries about 0.45 mm in size provide 100 microAmperes (μA, 1 μA=$10^{-6}$ Amperes of current) at 3.0 Volts. In an illustrated embodiment, a 3.7V and 25 milliAmperes (mA, 1 mA=$10^{-3}$ Amperes of current) hours (mAHr)rechargeable battery cell with dimension of 10.8 mm×19.0 mm×2.4 mm available from TENERGY CORP.™ of Fremont, California and found on All-Battery website as part number 241019 is used, which would fit into the available volume of housing 901. Based on this battery, the available energy is 333 Joules. The amount of time this battery can supply power for the example embodiment of 10 V display and backplane with 20% change per frame is 333 joules/80 μW, which is equal to about 48 days. Even for the worst case, of 452 mW consumption, this battery lasts 205 hours (about 8.5 days). This leaves most of the power for other components of the ocular prosthesis during a daily wear and recharge cycle. For a 16-hour wear duration, the example display consumes only 1.4% of the available power; and, the worst case display consumes only 7.8% of the available power.

An additional component consuming power available for the display is a converter to up-convert the 3.7 V of the battery to the 10V or more (e.g., up to 25 V) for the display device. An efficient power conversion circuit would yield about 95% efficiency whereas a relatively wasteful design would yield only 80% efficiency. In either case, a good operating life is still retained for the example embodiments of the display device. Most other circuits in the ocular prosthesis will be able to run directly from the battery voltage.

Lithium polymer batteries have a desirable combination of characteristics for the ocular prosthesis with display device. These characteristics include: best power to weight and power to size ratio; capable of being fabricated into non-standard shapes; capable of being fabricated as flexible; low self discharge rate; and no memory effect. Battery manufacturers specify a wide range for the number of useful cycles that a battery can be charged and discharged, from a low of a couple hundred cycles to over 10,000. This is likely due to the fact that there is no standard for calculating this number which is highly dependent on the discharge state of the battery, temperature, and the definition of useful life. When a lithium polymer battery is new, it is capable of being recharged back to its rated capacity but, the more charging cycles a battery endures, the lower it's charging capacity becomes. So the question of battery life for a particular application is better defined in terms of acceptable continuous wearable time for that time.

FIG. 10B is a graph that illustrates example recharge power for a battery suitable for an ocular prosthesis, according to an embodiment. The horizontal axis 1002 is number of recharge cycles and the vertical axis 1004 is percent of initial power capacity. Trace 1006 indicates that as the number of discharge and recharge cycles increase, the capacity of the battery diminishes. However, even after 500 cycles, the battery is still able to provide over 85% of its initial capacity. It is expected that with normal use, the battery lifetime will be in excess of 3 years, with 5 years (about 2000 cycles) as a sensible goal. For an embodiment using a battery with a (nominally) 3.7V unit rated at 25 mA Hr available from TENERGY CORP.™ of Fremont, California and found on All-Battery website as part number 241019, and a 16-hour daily endurance, maximum power consumption of approximately 5 mW (equivalent current consumption is about 1.5 mA) should still be available after 2000 cycles.

Various voltages are used for the different functional blocks. The used voltages are expected to range, in various embodiments, from 1.0 V to 5.0 V for the electronics and up to 25 V for the TFT backplane and display. The voltage available from the battery itself may vary from 4.2 V to 2.5 V depending on the state of discharge. Therefore, power conversion circuitry is employed, in some embodiments, to convert and regulate the available battery power to meet the uses of the various system subcomponents. Circuit design and components that meet these specifications are well known and readily available, being used in diverse products such as cell phones, watch backlights and personal data assistants (PDAs). The art in implementing this functional block includes the mitigation of electrical noise coupled into the processor and display due to the close confines of the prosthesis housing 901.

From the standpoint of energy density, the obvious choice is a lithium chemistry. However, printable batteries are emerging that are based on other chemistries such as zinc. These batteries are less energy efficient than lithium, but the ability to print (shape) the battery to best utilize available space might yet make this approach the winner. If an absolute voltage reference is utilized in some embodiments, in order to effectively recharge the battery, a tiny primary cell that has a long shelf life and stable output voltage is included. In some embodiments a semiconductor reference is used instead of, or in addition to, the primary cell; but such semiconductor references are large and consume relatively more power.

2.3 Implant Markers and Detectors

In some embodiments, the position and movement of the iris 925 and pupil 926 in the display area 913 on the display device 311 is based on the orientation and movement of the orbital implant 120. In some of these embodiments, an implant detector comprises a plurality of sensors distributed in the housing 901 of the ocular prosthesis 110 to triangulate on the position of a marker 122 that moves with the orbital implant 120. In four embodiments described in this section, a magnetic marker is used with Hall Effect sensors, a non-magnetic conducting foil is used as a marker with capacitors, a conductor is used as a marker with inductance sensors, and a light emitting marker is used with photodiodes.

2.3.1 Hall Effect Implant Detectors

FIG. 11A through FIG. 11D are block diagrams that illustrate example detection of a magnet moving with the orbital implant using Hall effect sensors on the ocular prosthesis, according to an embodiment. FIG. 11A is a block diagram that illustrates an anterior portion of the orbital implant 1100 with a magnet 1102 configured to move with the orbital implant 1100. In some embodiments, the magnet 1120 is inserted in a hole drilled into the orbital implant 1100. In some embodiments, the magnet is attached to the conjunctiva to move with the orbital implant, such as described below with reference to FIG. 11E and FIG. 11F or FIG. 11G through FIG. 11J.

FIG. 11B is a block diagram that illustrates an anterior view of an ocular prosthesis 1110 with example locations indicated where are disposed, at some depth behind or beside the display device, four Hall effect sensors 1120a, 1120b, 1120c, 1120d (collectively referenced hereinafter as Hall effect sensors 1120) that are able to detect a moving magnetic field when in the vicinity of the magnet 1102. This method of determining eye position relies on measuring the magnetic field strength of the implanted magnet 1102 at three or more points and thereby triangulating the position of the magnet. Considering that the field strength of a magnetic dipole falls off roughly as the cube of distance, the four sensors 1120 are arranged to minimize the distance any Hall Effect sensors would be from the magnet. In other embodiments, more or fewer Hall Effect sensors 1120 are used.

FIG. 11C shows the anterior view of the ocular prosthesis of FIG. 11B with position 1104a of the magnet behind the ocular prosthesis indicated by a dashed circle. Three zones are created, by the four Hall Effect sensors 1120 taken three at a time, indicated by sections 1122a, section 1122b and section 1122c (collectively referenced hereinafter as Hall Effect sections 1122). As the magnet moves around, a process executing on the processor 301 determines which zone the magnet is in by using the 3 strongest measurements of the Hall Effect. Within a zone, the distance to the magnet from each sensor is determined by the strength of the Hall Effect, and the position of the magnet within the zone is determined by triangulating the distance from the three closest sensors. For example, when the implant has moved to the viewer's left and up, the magnet is in section 1122a, as depicted in FIG. 11D. FIG. 11D shows the anterior view of the ocular prosthesis of FIG. 11B with new position 1104b of the magnet behind the ocular prosthesis. The Hall Effect measurement is greatest for Hall Effect sensors 1120a, 1120b and 1120c, therefore the magnet is in Hall Effect section 1122a. The Hall Effect is greatest at sensor 1120a, second greatest at sensor 1120c and third greatest at sensor 1120b, indicating increasing distances from each sensor. The processor 301 determines the position 1104b based on these measurements.

A significant factor, in determining sensitivity of the measurement with distance, is the strength of the attached magnet. For the size of magnet suitable for attaching to the implant or conjunctiva, it appears that a field strength of 2500 gauss is practical in some embodiments. In various embodiments a field strength of half to twice this values is also acceptable. A reasonable goal is for the sensitivity of the Hall Effect measurement to equal the resolution of the display device, e.g., the size of a pixel, about 0.36 mm. While it is envisioned that a cylindrical magnet with the poles oriented facing out and back will be used in some embodiments, in other embodiments other configurations are used.

FIG. 11E through FIG. 11J are block diagrams that illustrate an example marker configured to be attached to the conjunctiva that moves with the orbital implant, according to various embodiments. As shown in a side view in FIG. 11E and a perpendicular view in FIG. 11F, a marker 1140, such as the magnet 1102, is inserted into a small tube 1130 less than about 1 mm in diameter. One end of the tube is compressed, either before or after insertion of the marker 1140, to form a compressed end 1131 that prevents passage of the marker through that end. Any method may be used to form the compressed end 1131, including crimping, gluing, stapling, or suturing, or some combination. After insertion of the marker 1140, the remaining end of the tube is compressed, as indicated by the dashed lines. The tube with both ends compressed and marker enclosed is then fixed with or without sutures to the conjunctiva over the orbital implant to move with the orbital implant, either exactly or in some related manner. This arrangement and method offers the advantage of being suitable for retrofitting an orbital implant formerly inserted into the eye socket 12 and surgically attached to the eye muscles 18.

A disadvantage of the implanted magnet as a marker is that it interferes with nuclear magnetic resonance (NMR) imaging (MRI) and equipment, which is a commonly used diagnostic tool that is desirably not off limits to a subject using the present ocular prosthesis. To address the issue of MRI exposure, the magnet could be arranged to be removable without a surgical procedure. One such arrangement is to affix a non-metallic container, such as the tube 1130 described above, into the conjunctiva in a way not to interfere with either the sphere or the ocular prosthesis, but open to the surface. A magnet is placed into the container and held in place by some method, such as friction, sutures or a clip. It is expected that a tool, which may be specially designed for this purpose, will be used for insertion and extraction of the magnet from the container.

It is anticipated that the magnetic sensor will be immune to most sources of man-made interference since there are relatively few electronic devices that emit strong magnetic fields. Furthermore, if a small magnetic field were to be emitted, say from a cell phone, it would be radiating in the GHz frequency range (its operating frequency) which is far from the nearly dc frequency the Hall Effect implant detector uses.

Power dissipation for operating the Hall Effect sensors is expected to be comparable to the display described above and processor, described below. Considering that a measurement is made once per frame (50 ms at 20 FPS) and it is expected that a measurement should take no more than 1 ms, the illustrated Hall Effect-sensors will only be operating 2% of the-time. For the Hall-Effect devices that have been identified, part numbers #A1391, A1392, A1393, A1395 from ALLEGRO MICROSYSTEMS INC.™ of Worcester, Massachusetts, the current consumption is computed to be less than 10 mA when operating, and therefore the sensor will have an average current consumption of only 2% of that, or around 200 μA. This is about 15% of the power budget when operating directly from the battery.

In some embodiments, a paddle marker is configured to hold a magnet or some other emitter or detectable device for use in detecting motion of the orbital implant, and any associated electronics. FIG. 11G depicts distal plan view of a paddle marker 1150 with an detectable device 1154 centrally located and six circular indentations 1152a. 1152b, 1152c, 1152d, 1152e, 1152f (collectively referenced hereinafter as fenestrations 1152), set three at a time in each blade (broad) portion of paddle marker 1150. These fenestrations 1152 are configured to allow conjunctiva tissue fixation through the holes to stabilize the paddle on the implant and prevent migration relative to the orbital implant. The paddle marker is implanted under the conjunctiva to the orbital implant and is not connected with other parts of the prosthetic device. The paddle marker contains within it the magnet or other emitting or detectable device and is placed in position surgically or with a sub-conjunctival injector or delivery device. For example, circular fenestrations 1152, 1152b and 1152c are found in broad portion A of marker 1150. Broad portion A makes up one blade of the paddle marker 1150.

The dimensions of the paddle marker are small enough so that the entire marker sits easily in front of the orbital implant. For example the narrow shaft connecting the blades is less than 0.1 inch (2.4 mm) wide. In the illustrated embodiment, the shaft is about 0.04 inches (0.9 mm) wide. FIG. 11H shows a side elevation view of the marker 1150 that is also preferably less that 0.1 inch (0.6 mm). In the illustrated embodiment the marker is about 0.04 inches (1.0 mm) at its widest in the shaft and narrows to about half that thickness in each blade portion of the marker 1150. FIG. 11I depicts close up of a blade, broad portion A, with example dimensions, such as circular indentation diameter of about 0.035 inches. Based on a coordinate system with origin at the center of the middle indentation 1152b, the widest portion of the blade extends about 1 millimeter above and below the origin, and the end of the marker is about 2.3 mm from the origin, and the two remaining indentations in the portion A are centered 1.1 mm left and right of the origin. FIG. 11J depicts a perspective view of the marker 1150 with indentations 1152 and detectable device 1154.

2.3.2 Capacitance Implant Detectors

The capacitive sensor is based on a variable capacitor principle. A circular conducting foil is implanted into the conjunctiva. Additional foils inside the prosthesis act to form simple serial plate capacitors. As these surfaces move with respect to one another, the overlapping areas change and so does the capacitance. This effect is easily seen from the defining equation of capacitance illustrated in FIG. 12A through FIG. 12 D. FIG. 12A through FIG. 12D are block diagrams that illustrate example detection of the orientation the orbital implant with sensors on the ocular prosthesis that measure variable capacitance, according to an embodiment. FIG. 12A is a block diagram that illustrates an anterior portion of the orbital implant 1200 with a non-magnetic electrically conducting implant foil 1202 configured to move with the orbital implant 1200. In some embodiments, the foil 1202 is inserted in a conjunctiva covering the orbital implant 1200.

FIG. 12B is a block diagram that illustrates an anterior view of an ocular prosthesis 1210 with example locations indicated where are disposed, at some depth behind or beside the display device, four conducting foils 1212a, 1212b, 1212c, 1212d (collectively referenced hereinafter as prosthesis foils 1212) that are able to form serial capacitors when in the vicinity of the implant foil 1202. This method of determining eye position relies on measuring the capacitance at three or more capacitors and thereby triangulating the position of the implant foil 1202. The circular central fixed foil is used to drive the larger circular foil on the moving surface. The geometric constraint is that the driving foil advantageously overlaps the driven foil completely for all motions of the eye. This keeps the driving signal to the moving foil constant. The capacitance between the moving foil and the three annular sense foils are measured. The ratio of these capacitances is used to determine position. This is considered series capacitance because the drive is first capacitively coupled to the moving foil, then capacitively coupled a second time back to the three fixed sense foils. In other embodiments, more or fewer prosthesis foils 1212 are used.

FIG. 12C shows the anterior view of the ocular prosthesis of FIG. 12B with position 1220a of the implant foil 1202 behind the ocular prosthesis indicated by a dashed circle. Four capacitors are created. As the implant foil 1202 moves around, a process executing on the processor 301 determines where the implant foil is centered using the 3 measurements of capacitance at the 3 peripheral foils. The coverage of the implant foil 1202 by each prosthesis foil 1212 is determined by the strength of the capacitance, and the position of the implant foil 1202 is determined by triangulating the coverage from the three peripheral foils.

Locating the foil in the conjunctiva instead of on the implanted sphere addresses two important issues. First, the vestigial motion of the sphere is actually driven by the motion of the conjunctiva. For a newly implanted sphere, it takes time for the conjunctiva to integrate with the sphere. Until this integration takes place, the sphere is free to move, resulting in an arbitrary final position of any attached foils. The second advantage is for patients who have had a prosthetic eye for quite some time. For these patients, performing a small procedure on the conjunctiva is favored over implanting a new sphere.

Depending on how the implant foil 1202 is surgically installed, there is a possibility that the foil 1202 could move and rotate before becoming integrated with the skin. To accommodate this motion, a single circular foil is placed somewhat centered as shown in FIG. 12A. This construction completely resolves the issue of rotation and it is believed that the exact placement is not critical. Desirable properties for the foil material are non-magnetic for compatibility with MRI equipment, electrically conductive, biologically inert and flexible. The construction of the implanted foil also needs to consider eddy currents, which will cause heating, when exposed to the strong RF magnetic fields of the MRI scanner. This issue is addressed in some embodiments by the combination of providing slots in the foil and using a marginally conductive material that will provide resistance to these circulating currents.

Referring to FIG. 12B, the prosthetic center circular foil 1212a stays essentially completely over the implanted circular foil 1202, creating a fixed capacitor. The remaining three prosthetic foil pieces, 1212b, 1212c and 1212d each form a variable capacitor depending on the position of the eye. It some embodiments, the computation of position is done as a relative measure of the 3 variable capacitances. This method reduces the effects of changing environmental conditions that will alter the absolute capacitance values which can be normalized by the value of the fixed capacitor formed by the center coil 121a and the implant foil 1202.

While the measurement technique is based on the ratio of the 3 variable capacitors, seemingly making the absolute capacitor values uninteresting, there are some practical aspects to be considered. FIG. 12E and FIG. 12F are block diagrams that illustrate example factors that affect the measured variable capacitance, according to an embodiment. The variables that mostly determine capacitance are the overlapping area of the two plates 1232 (given by length 1235, L, times width 1233, W), the distance 1237, D, separating the two plates and the dielectric constant of the material 1236 filling the space between the two plates. These properties describe capacitor 1230. The "textbook" formula that describes the capacitor 1230, shown in FIG. 12E, is simplified as it does not include fringing fields 1242 of the electric field lines 1240 illustrated in FIG. 12F. This simplification is valid when the aspect ratio of the overlapping space dimension 1234, L, is larger than the separating space 1237, D.

The capacitance C (in Farads) is given by Equation 1. The largest unknown for computing this capacitance is the dielectric constant, since the dielectric medium is the conjunctiva. According to published papers, the dielectric constant of human skin is dependent on a number of factors, including frequency. Considering that 70% of skin is composed of water which has a dielectric constant of only 80, then computing the total available capacitance across the surface of the eye, 20 mm diameter, with a 1 mm separation for the thickness of the conjunctiva, is about 70 pF. If the total area were to be evenly divided among the 4 prosthetic foils, each piece would measure one quarter of the total or 17.5 pF. The variable capacitors would then expect to see a capacitance range from around 1 pF to about 17.5 pF. The variable capacitors are in series with the fixed capacitor of 17.5 pF creating a circuit capacitance range of 0.9 pF to 8.75 pF. At these low values, stray capacitances in the driving and receiving circuitry could contaminate or obscure the measurement. In some embodiments, the effect of stray capacitances is compensated through a calibration procedure. Experiments were performed that confirmed for the frequencies of interest (low MHz range) the saline solution behaves substantially like pure water.

The variable conductivity of skin, which is highly dependent on moisture and salt (ion) content poses a considerable challenge. As previously mentioned, the conductivity of the skin has an impedance that competes with the capacitive reactance at the near 20 Hertz (Hz, 1 Hz=1 cycle per second) frequency of interest. In effect this places a resistor in parallel with the capacitor, which attenuates the capacitive effect. In some embodiments, a sinusoidal excitation around 100 kHz is used and the resulting signal measured at the processor 301. Providing a 10-to-1 oversampling and averaging many 100 kHz cycles together allow both amplitude and phase to be measured. In some embodiments, this approach is replaced with a more complicated experiment which measures the resonant frequency of an inductive/capacitive circuit. For this measurement, an inductor is placed in series with the foils to form a resonant tank circuit; and, when excited, exhibits the resonant frequency.

Since all electronic devices emit electric fields, the capacitive sensor is inherently more susceptible to its environment than the magnetic sensor. The amount of energy emitted from an electronic device is a known quantity which can be used to help quantify this issue. In some embodiments, filters and shielding are included to address external sources of electrical interference.

To maintain the lowest possible power consumption, it is desirable to prevent direct current (DC) from flowing through the conductive skin dielectric. To accomplish this, the foils are advantageously covered with an insulating material. The total power consumption is mostly dependent on the impedance of the sensor's capacitors (which depends on the dielectric constant of the skin) and on the percent of time it needs to run. As with the magnetic sensor, it's expected that this sensor will run about 2% of the time, making the average power consumption less than the display.

2.3.3 Inductance Implant Detectors

The inductance sensor is based on principles of the de-tuning effects of nearby conductors on LC circuits. An LC circuit, also called a resonant circuit, tank circuit, or tuned circuit, consists of two electronic components connected together; an inductor, represented by the letter L, and a capacitor, represented by the letter C. The circuit can act as an electrical resonator, an electrical analogue of a tuning fork, storing energy oscillating at the circuit's resonant frequency. The inductance sensor presented here offers an advantage over the Hall Effect sensors in that this inductance circuit does not interfere with magnetic resonance based medical imagers, such as MRI and MRSI. FIG. 12G through FIG. 12L are block diagrams that illustrate example detection of a conductor moving with the orbital implant using inductance sensors on the ocular prosthesis, according to an embodiment.

Figure 12G:
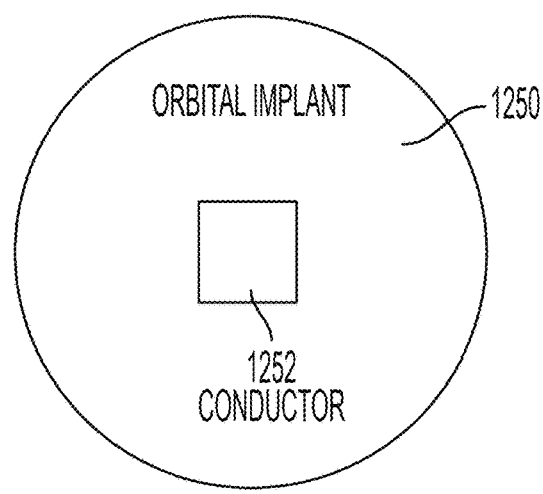

FIG. 12G is a block diagram that illustrates an anterior portion of the orbital implant 1250 with a conductor 1252 configured to move with the orbital implant 1250. In some embodiments, the conductor 1252 is attached to the orbital implant 1250. In some embodiments, the conductor 1252 is attached to the conjunctiva to move with the orbital implant, such as described above with reference to FIG. 11E and FIG. 11F or FIG. 11G through FIG. 11J.

Figure 12H:
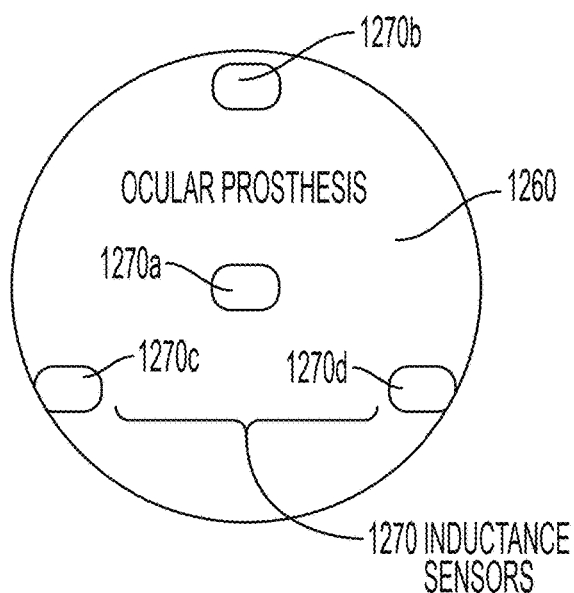

FIG. 12H is a block diagram that illustrates an anterior view of an ocular prosthesis 1260 with example locations indicated where are disposed, at some depth behind or beside the display device, four inductance sensors 1270a, 1270b, 1270c, 1270d (collectively referenced hereinafter as inductance sensors 1270). This method of determining eye position relies on measuring the distance from three or more points and thereby triangulating the position of the marker. In other embodiments, more or fewer inductance sensors 1270 are used.

Figure 12I:
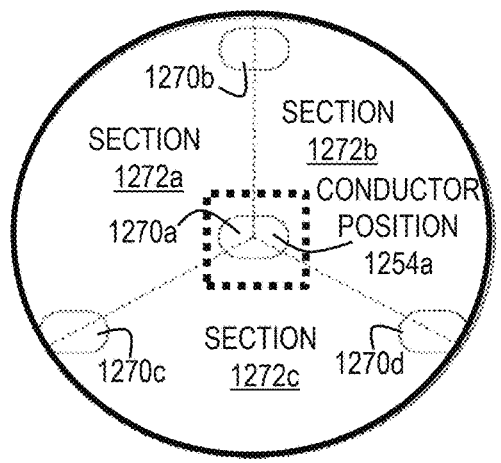
Figure 12J:
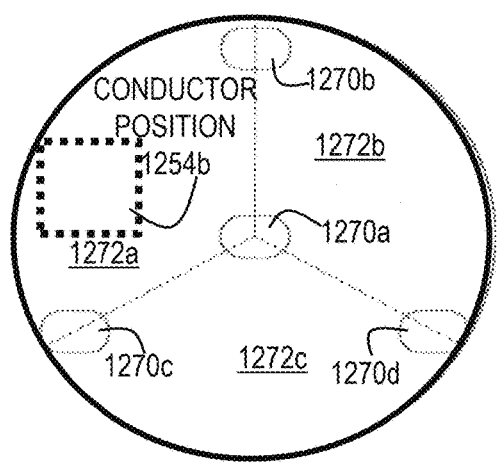

FIG. 12I shows the anterior view of the ocular prosthesis of FIG. 12H with position 1254a of the conductor behind the ocular prosthesis indicated by a dashed square. Three zones are created, by the four inductance sensors 1270 taken three at a time, indicated by sections 1272a, section 1272b and section 1272c (collectively referenced hereinafter as inductance sections 1272). As the conductor 1252 moves around, a process executing on the processor 301 determines which zone the conductor is in by using the 3 strongest measurements of the inductance. Within a zone, the distance to the conductor from each sensor is determined by the Equations 4a and 4b given below, and the position of the conductor within the zone is determined by triangulating the distance from the three closest sensors. For example, when the implant has moved to the viewer's left and up, the conductor is in section 1272a, as depicted in FIG. 12I. FIG. 12J shows the anterior view of the ocular prosthesis of FIG. 12H with new position 1254b of the conductor behind the ocular prosthesis. The inductance measurement is greatest for inductance sensors 1270a, 1270b and 1270c, therefore the conductor is in section 1272a. The processor 301 determines the position 1254b based on the distance measurements at these three sensors.

An example inductance sensor 1270, according to one embodiment, is depicted in FIG. 12K, and comprises a tank circuit between terminals 1276. The tank circuit includes sensor inductor Ls 1273 that comprises half of an open transformer, sensor resister Rs 1274, and sensor capacitor C 1275. As depicted in FIG. 12L, in the presence of a conductor, e.g., target metal surface 1252, the fields radiating form inductor L 1273 induce eddy currents in the conductor depending on the conductance 1253 of the metal, setting up fields that oppose those of inductor L 1273. The result is an equivalent circuit that resonates according to combined inductance and resistance of the sensor and the conductor (e.g., metal surface 1252). The effect of the conductor 1252 on the inductance of the equivalent circuit is given by L and depends on the distance d 1255 between the inductor Ls and the conductor 1252, so L is a function of d and represented as L(d). The energy drain to power the eddy currents appears as an additional resistance R, also a function of distance d 1255, and represented as R(d). Thus the equivalent circuit in the presence of a conductor appears to have inductance 1283 of LS+L(d) and resistance 1284 of Rs+R(d). The equivalent circuit has a different resonant frequency, which can be measured across terminals 1276.

The resonant frequency $f_0$ of the equivalent circuit depends on the inductance L and capacitance C of the equivalent circuit, as given by Equation 4a.

$$f_0 = 1/2\pi(LC)^{1/2} \qquad (4a)$$

The equivalent parallel resonance impedance, Zp, is given by Equation 4b $$Zp(d) = (1/([Rs+R(d)])*((Ls+L(d)])/C \qquad (4b)$$

By measuring simultaneously the resonant frequency $f_0$ and the power consumed at the resonant frequency, the distance d can be determined. The resonance frequency gives L=Ls+L(d) using equation 4a; and the power depends on Zp which is used to derive d based on Equation 4b.

Example inductance sensors include the LDC1000™ inductance-to-digital converter from Texas Instruments™ of Dallas, Texas, which provides a sensitive and versatile position-sensing technology. The LDC1000™ measures the equivalent parallel resonance impedance Zp given by Equation 4b. The LDC1000 regulates the oscillation amplitude to a constant level while monitoring the energy dissipated by the resonator. By monitoring the amount of power injected into the resonator, it calculates the value of Zp. Also, measuring the oscillation frequency of the LC tank circuit determines the inductance of the helical coil in the LC circuit. Zp and frequency are output as digital values. Calibrated to read out changes in the coil's inductance to 24-bit precision, the LDC1000 drives and monitors the tank circuit 1270. The drive frequency, which determines the dimensions of the coil to some extent, can be anywhere from 5 kiloHertz (kHz, 1 kHz=$10^3$ Hertz, Hz, 1 Hz=1 cycle per second) to 5 MegaHertz (MHz, 1 MHz=$10^6$ Hz). In addition to providing for oscillation frequencies from 5 kHz to 5 MHz, the value of Zp can theoretically range from 798 Ohms (Ω) to 3.93 MegaOhms (MΩ, 1 MΩ=$10^6$ Ohms). In practice, a circuit designer selects from a tighter range and enters those values in a pair of registers.

2.3.4 Optical Implant Detectors

In some embodiments, tracking the position of the conjunctiva is performed by disposing an imager on the curved posterior surface of the ocular prosthesis. The pixel density of the display device (approximately 72×36 pixels), which is visible at the anterior surface, can be matched by the imager on the posterior surface. Given an illumination source for a marker (such as a tattoo or light emitter) on the conjunctiva, movement of the conjunctiva can be tracked to the precision of the display device resolution. In some of these embodiments, the curved imager of the implant detector utilizes much of the same technology, such as the TFT backplane, also used for the display device. This sensing method has the advantage of being free from the MRI limitation and being inherently immune to other confounding influences such as magnetic fields or electrical interference. In some embodiments, the marker is placed on the conjunctiva as marker 1140 inserted into the tube 1130 described above with reference to FIG. 11E and FIG. 11F, or inserted as the detectable device 1154 of the paddle marker of FIG. 11G to 11J.

In some embodiments, the illumination source (such as a fluorescent dot or light emitting diode) used as a glowing implant marker is placed on the conjunctiva and the marker position is tracked using a sparse array of photo detectors in the prosthetic cover. Again, in some of these embodiments, the glowing implant marker is placed on the conjunctiva as marker 1140 inserted into the tube 1130 described above with reference to FIG. 11E and FIG. 11F, or inserted as the detectable device 1154 of the paddle marker of FIG. 11G to 11J. This sensing method is also free from the MRI limitation and immune to other confounding influences, and has the further advantage of consuming less space and power. Such embodiments use a much smaller array of photo detectors in a non-imaging configuration. The intensity at nearby photodiodes is used to compute the distance to the glowing implant marker. This approach is technologically less demanding than development of a complete imager and represents a lot less information that needs to be digested by the local processor 301. The result is determined in many fewer computational cycles, hence consuming less power by the processor. This sparse optical sensor array uses approximately 24 individual photodiodes, each of which has very low power consumption, compared to 2592 photodiodes for a 72×36 element imager.

In some embodiments, an array of illuminators, such as light emitting diodes (LEDs), are used to excite a fluorescent implant marker, presumably once per display frame, e.g., at about 20 Hz. In some of these embodiments, there is a sparse array of such illuminators; and, in some embodiments this sparse array of illuminators is matched to the array of optical sensors. Such illuminators are major power consumers for many of these embodiments. Fortunately, the fluorescent implant marker is useful even when it is not very bright, since it emits in a darkened environment when the illuminators are switched off, and the photodiodes are extremely sensitive. So, in such embodiments, total power consumption of the illuminators and photodiodes are acceptably low. In order to reduce power consumption, in some embodiments, these illuminators are not used all at once, since only a few would be line-of-sight to the fluorescent implant marker. In these embodiments, after the florescent implant marker is located, only the one illuminator that is closest is turned on. This pumps up the fluorescence while using the least possible illuminator power. If executed at the display frame rate, it suggests that the fluorescence half-life of the fluorescent implant marker should be at least a few frame times.

There are many common fluorescent materials to choose from for various embodiments. In some embodiments, quinine is used as a fluorescent tracer because quinine is a really bright emitter that's harmless if ingested in small quantities. Various fluorescent materials are used for medical procedures and are involved in some embodiments. For example, in some embodiments Fluorescein, which is used to visualize blood flow during ophthalmic exams, is used as a glowing implant marker.

In various embodiments, the fluorescent material used as the glowing implant marker is selected based on one or more of the following considerations. In some embodiments other emitters are used, such a chemical-luminescent or bioluminescent materials that emit light as a result of an internal chemical interaction, or materials that absorb light quickly and emit over an extended time on the order of one frame duration at the same optical wavelengths. For example, in some embodiments, "Luciferase" is used. The chemical mechanism for light emission from Luciferase is a reaction involving oxygen and Adenosine-5'-triphosphate (ATP).

For fluorescent and other light emitting materials, activating wavelength (usually expressed in nanometers, nm, where 1 nm=$10^{-9}$ meters) is well matched to an available LED illuminator. Emission wavelength is desirably in a range from about 500 nm to about 1000 nm. The shorter wavelengths can be detected more efficiently (if matched to a suitable photodiode) and they suffer less background noise from the patient's own black body radiation. The efficiency of converting activation wavelength power into fluorescent wavelength power (also called quantum efficiency) is desirable above 50%. This will dominate overall power consumption of the position detector. It is desirable for the fluorescence time constant (e.g., decay time) to be short, such as equal to just a few frame times, as described above. Some embodiments use materials that have very long time constants, e.g., many hours. In some of these embodiments, this type of material is activated up in the morning (e.g., using an external light source) and then would fluoresce for the entire day. This yields the lowest power consumption and smallest battery pack for the ocular prosthesis. Long term stability is desirable so that the fluorescent implant marker survives in-vivo for at least a year and preferably much longer. A bio-compatible material is used in some embodiments so that the marker can be placed on the conjunctiva like a tattoo mark. In other embodiments, the marker is encased in a durable biocompatible container that is transparent, such as the tube 1130 as described above with reference to FIG. 11E and FIG. 11F, or paddle marker described with reference to FIG. 11G through FIG. 11J. Existing FDA approval simplifies the adoption of a fluorescent emitter as the glowing implant marker.

In some embodiments a single light emitting diode (LED) is used as the glowing implant marker instead of or in addition to the fluorescent implant marker. Suitable visible band LEDs are packaged in a surface mount 0201 style. This package is a rectangular solid that is 0.010 inches (0.25 mm) square by 0.020 inches (0.5 mm) long. The LED can fit inside a tube that is about 0.025 inches (0.64 mm) diameter. Flattening the ends of the tube (a bit like a kayak paddle), as depicted in FIG. 11F, stabilizes the implant so that the LED shines in a predictable direction. In some of these embodiments, the ends of the tube include non-magnetic conductors that form an electric field antenna or induction coil that can be powered from a radio frequency transmitter in or used by the implant detector of the ocular prosthesis, causing the LED to glow. An advantage of using an electric field antenna instead of an induction coil, is that the antenna will not overheat when subjected to the strong magnetic fields of a MRI device.

The encapsulated LED is similar to other structures already accepted by the conjunctiva, so it should be well tolerated by the patient. Also, the materials used in the implant are safe for use in intense magnetic fields, so the implant can stay in place during an MRI exam. The amount of light needed from the LED is quite small, perhaps a few microwatts. The LED is powered for approximately 1 millisecond out of each frame of 59 milliseconds or longer, so the duty cycle is less than about 2%. This means that the transmitting antenna can be activated with many milliwatts of electrical energy to compensate for energy losses in the system, while consuming only a small percentage of the available battery power.

Figure 13A:
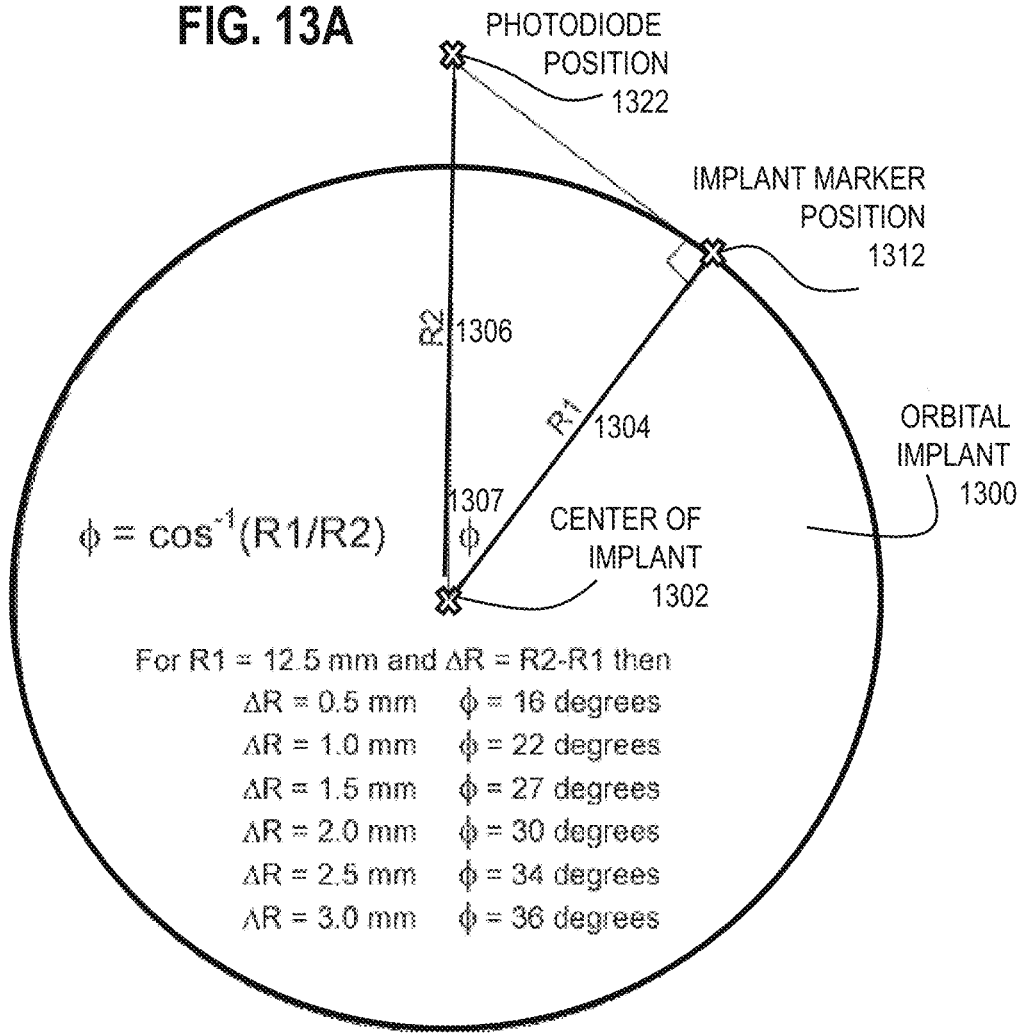
FIG. 13A is a block diagram that illustrates an example radius of a field of view of a photodiode disposed in the ocular prosthesis, according to an embodiment.

The placement of photodiodes on the posterior surface of the orbital implant is affected by the line of sight between the photodiode and the marker, which is limited because the marker is on a curved surface. FIG. 13A is a block diagram that illustrates an example radius of a field of view of a photodiode disposed in the ocular prosthesis, according to an embodiment. The orbital implant 1300 (and conjunctiva) has a radius R1 1304 of about 12.5 mm from a center 1302 of the orbital implant in an ocular prosthesis system for an adult. The photodiode is displaced from the surface of the orbital implant (and conjunctiva) by an air gap of some degree and the depth of the photodiode behind the posterior surface of the ocular prosthesis, which depth is desirably transparent to light. Thus the distance R2 1306 from the center 1302 of the orbital implant to the position o1322 of the photodiode is greater than R1 by ΔR, which varies in various embodiments from about 0.5 mm to about 3 mm. The implant marker is on the horizon of the photodiode field of view at an angle ϕ that depends on R1 and R2 (or ΔR) as given by Equation 5.

$$\phi = \arccos(R1/R2) = \arccos(R1/(R1+\Delta R)) \qquad (5)$$

The dependence of Don ΔR is listed in FIG. 13A, which shows that Ovaries in various embodiments from about 16 degrees to about 36 degrees. Therefore, in some embodiments, the photodiodes are disposed just 2 mm above the ball to achieve approximately a 60 degree field of view (30 degrees to either side of the photodiode). Gaining a bit more height widens the view, but not very quickly. For instance, in some embodiments, a 72 degrees field of view is achieved for photodiodes disposed at a height of 3 mm above the orbital implant (and conjunctiva).

Figure 13B:
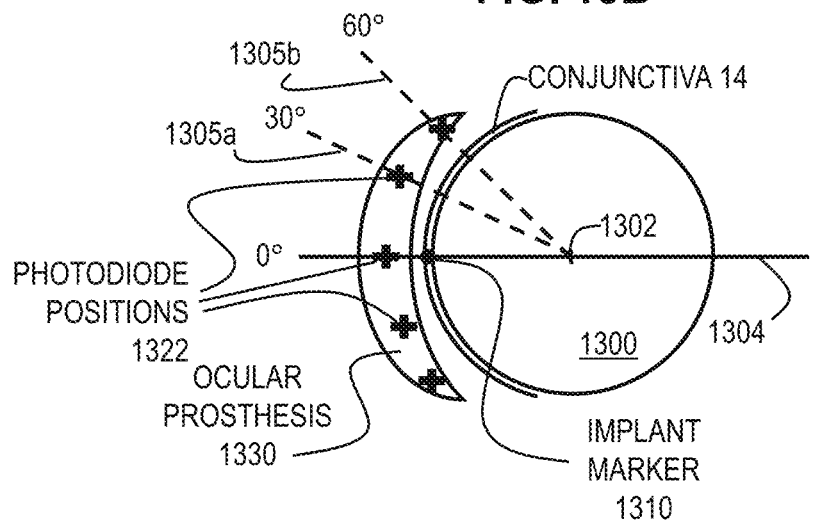
FIG. 13B is a block diagram that illustrates example distribution of photodiodes disposed in the ocular prosthesis to detect movement of an implant marker that moves with the orbital implant and emits light, according to an embodiment.

Using the 2 mm height and maximum rotation of the orbital implant (called "ocular deflection" hereinafter) of +/−60 degrees horizontally and +/−45 degrees vertically as an example, it only takes a few sensors to keep the implant marker in view at all times. However, it takes quite a few sensors before there is enough coverage so that the implant marker is always within view of multiple sensors at the largest ocular deflection angle. FIG. 13B is a block diagram that illustrates example distribution of photodiodes disposed in the ocular prosthesis to detect movement of an implant marker that moves with the orbital implant and emits light, according to an embodiment. The orbital implant 1300 is depicted in horizontal cross section with conjunctiva 14 into which has been attached the glowing implant marker 1310 (either fluorescent dot or LED, or some combination, in various embodiments). In some embodiments, the glowing implant marker is the detectable device 1154 in the paddle marker 1150. Also depicted is ocular prosthesis 1330 that includes multiple positions 1322 for photodiodes. Horizontal ocular deflections of 0 degrees at ray 1304, 30 degrees at ray 1305a and 60 degrees at ray 1305b are also depicted. When the horizontal ocular deflection is 60 degrees, the implant marker is on the 60 degree ray 1505 and is visible to a photodiode at a position on the 30 degree ray 1305a, but not to a photodiode at a position on the 0 degree ray 1304. Therefore additional photodiodes are includes at additional positions, such as on the 60 degree ray 1305b. To insure coverage by three photodiodes, additional positions are added.

Figure 13C:
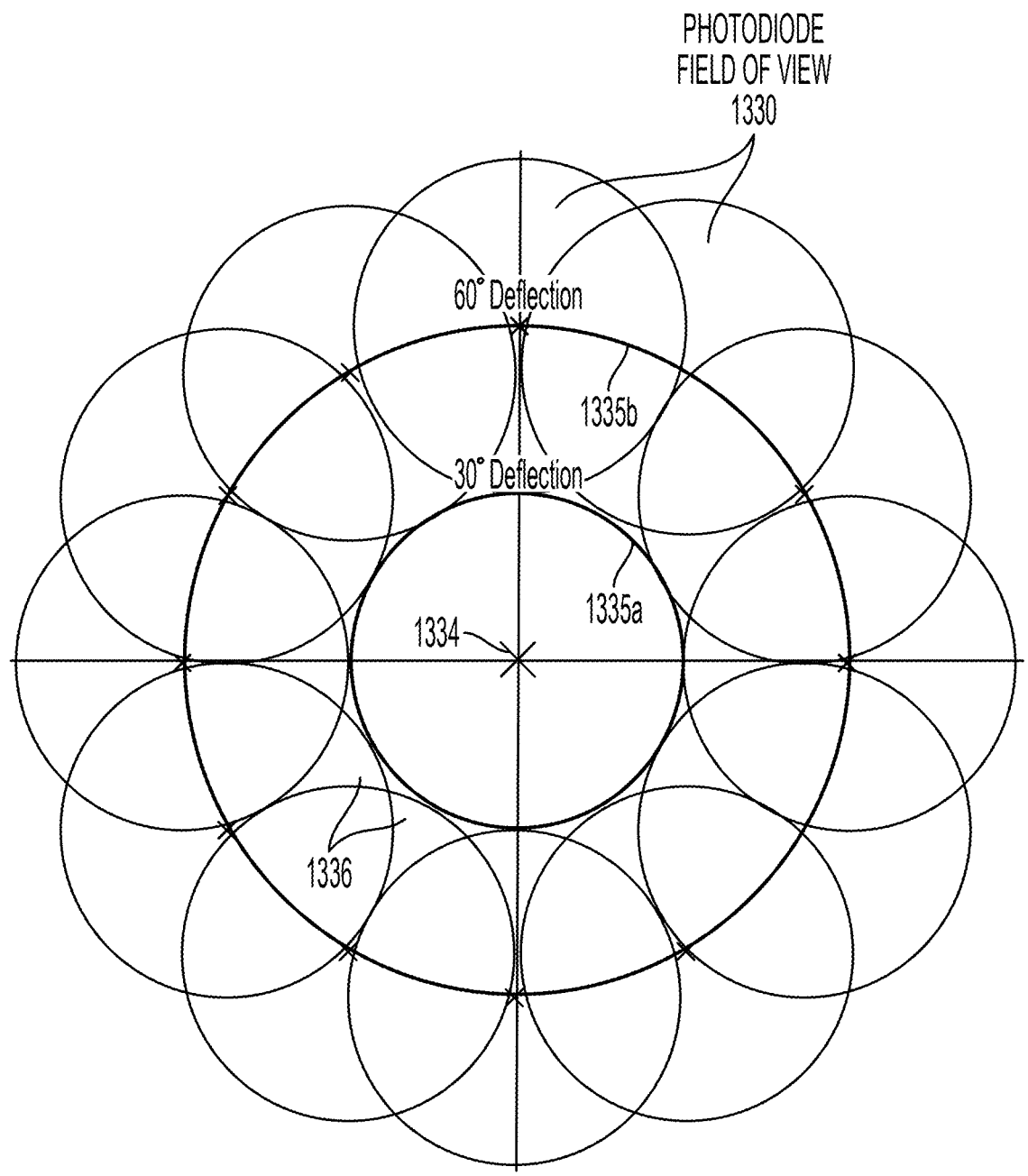
FIG. 13C and FIG. 13D are block diagrams that illustrates example overlapping fields of view of multiple photodiodes disposed in the ocular prosthesis, according to various embodiments.

In one set of embodiments, about 12 photodiode positions are distributed on the 60 degree deflection circle as shown in FIG. 13C and FIG. 13 D. FIG. 13C and FIG. 13D are block diagrams that illustrates example overlapping fields of view of multiple photodiodes disposed in the ocular prosthesis, according to various embodiments. FIG. 13C is a diagram that illustrates example positions for photodiodes on or within a posterior surface of an ocular prosthesis, according to some embodiments. FIG. 13C depicts the center 1334 of the posterior surface that corresponds to the 0 degree deflection ray 1304 of FIG. 13B, a 30 degree circle 1335a on the posterior surface that intersects the 30 degree ray 1305a of FIG. 13B, and a 60 degree circle 1335b on the posterior surface that intersects the 60 degree ray 1305b of FIG. 13B. A photodiode position is at the center of photodiode field of view circle 1330. To obtain at least two sensor coverage of each 60 degree ocular deflection, 12 photodiode fields of view 1330 overlap by positioning each photodiode 30 digress along the 60 degree circle 1335b. Even with a photodiode position at the center 1334, there are many positions where the implant marker is in view of only one photodiode, e.g. at areas 1336.

Figure 13D:
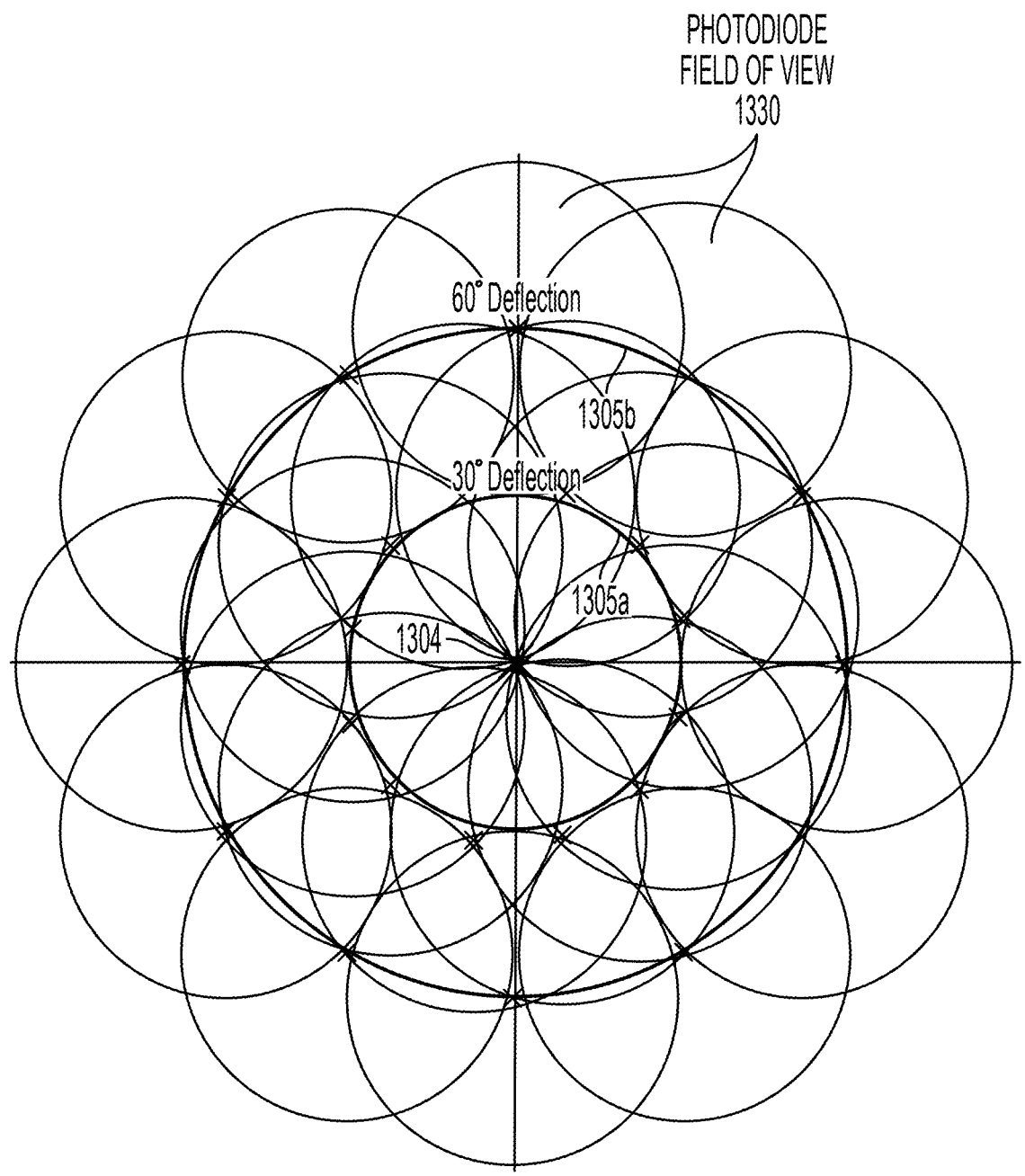

Placing a second ring of sensors on the 30 degree deflection circle 1335a provides the desired coverage, plus highly overlapped coverage in the central field of the eye. This arrangement is shown in FIG. 13D. FIG. 13D is a diagram that illustrates example positions for photodiodes on or within a posterior surface of an ocular prosthesis, according to some embodiments. FIG. 13D depicts the center 1334 of the posterior surface, the 30 degree circle 1335a, and the 60 degree circle 1335b. A photodiode position is at the center of photodiode field of view circles 1330. In this embodiment, 12 photodiode positions are added, arranged every 30 degrees along the 30 degree circle 1335a. Thus complete coverage with multiple photodiodes is achieved with 25 photodiodes. In some embodiments, the photodiode at the center is considered superfluous, and it is omitted, leaving the total number of photodiodes at 24. In other embodiments, other photodiode positions are also eliminated, or shifted, or both to reduce the complexity and computation load and power consumption of the optical implant detector. In some embodiments, one or more other photodiode positions are added.

In another embodiment, adequate coverage can be obtained by placing a single LED in the conjunctiva 14 at the zero degree ray 1304 of the orbital implant, as depicted in FIG. 13B, then a ring of about 6 optical sensors (e.g., photodiodes) at the 60 degree circle 1335b depicted in FIG. 13C and FIG. 13D and a second ring of 12 sensors at the 30 degrees circle 1335a depicted in those same figures, for a total of 18 optical sensors (e.g., photodiodes). With this geometry in mind, physical size becomes an important characteristic for the photodiodes.

Most optical sensors are packaged in pretty large hermetically sealed housings, typically 5 to 6 mm in diameter. Unpackaged chips are not readily available since a p-type/intrinsic/n-type semiconductor (PIN diode) used in many photodiodes has stringent packaging requirements. Ultimately nearly identical PIN diodes were identified from Hamamatsu (110805S10625) and Advance Photonics (PDB-C154SM).

For the wearable version, a similar sensor in a small surface mount package, or else as an unbonded die that can be attached directly to a flexible circuit card. These devices are inexpensive, around $1.00 in modest volume, suitable for an affordable prosthesis. For example, the HAMAMATSU™ 110805S10625 package is only 2.7 mm by 3.2 mm with an active area of 1.3 mm by 1.3 mm, and is suitable for use as a photodiode at the 12 positions along the 30 degree circle 1335a and is suitable for use in the ocular prosthesis depicted in FIG. 20, described in more detail below. Peak spectral response is at 940 nm (near infrared) falling to about 50% in the visible region (480 nm). Spectral sensitivity is approximately 550 mA per watt of illumination. Typical dark current is 2 pA at 1V reverse voltage, dropping to 0.1 pA at 10 mV bias. But the maximum dark current is much larger, at 10 nA. Maximum detector current is about 2 μA with 100% illumination. Noise equivalent power is 0.15 pW per square root Hz (bandwidth). Wide field of view is 133 degrees Full Width at Half Maximum, with better than 90% response over the desirable+−30 degree field of view.

A typical optical sensor is the HAMAMATSU™ 82386 line of silicon photodiodes from HAMAMATSU PHOTONICS K.K.™ of Hamamatsu City, Japan. These devices work well in the near infrared, with best sensitivity in the 800 nanometer (nm, 1 nm=$10^{-9}$ meters) to 1000 nm range of optical wavelengths. The S2386-18K is packaged as a TO-18 which is a 5.4 mm diameter can, a potential choice for an experimental bench model of the ocular prosthesis, described in more detail below. Using the S2386-18K as an example, the field of view is well matched to the embodiments described above, yielding more than 80% response throughout a 60 degree aperture (+/−30 degrees). Peak spectral sensitivity is 0.6 amperes per watt. Response times (depending on the load resistance) are in the 1 μs range. So this sensor is capable of being quickly powered up to take a look at the field of view and then de-activated to save power. In operation, the photodiode gets back biased by a few volts and exhibits room temperature leakage (dark current) of less than 10 pA. So power consumption is imperceptibly small even if the sensor is energized all the time.

Using this sensor as an example, the desirable properties of the glowing implant marker can be determined for various embodiments. The glowing implant marker desirably emits more optical power than the sensor dark current, even when viewed at the maximum distance and angle. A baseline computation of the required optical power is performed by assuming that the glowing implant marker emits its power uniformly over a hemispherical area. The maximum viewing distance is approximately R1*tan (30 degrees), which equals 7.2 mm for R1=12.5 mm. The hemisphere of this radius has surface area $2\pi RI^2$=327 mm$^2$. The example sensor has an area of 1.2 mm$^2$ so the sensor intercepts approximately 0.4% of the light emitted by the glowing implant marker. Using a sensor efficiency of 80% (at maximum viewing angle)×0.6 amperes/watt (sensitivity), it is determined that the glowing implant marker preferably emits 5.6 nW or more to raise a sensor current that is at least double the 10 pA dark current.

The detectors operate at very low power but it is desirable to operate the detectors at the lowest possible light level, especially for embodiments that use illuminators to power a fluorescent implant marker. Detector circuits often apply a reverse bias to the photodiode. The reverse bias minimizes the capacitance of the detector and thereby improves frequency response. But the penalty is increased dark current. Applicant's approach is to operate the PIN diode at zero bias voltage. In theory, this reduces the dark current to zero. Light input creates charged pairs in the detector, resulting in a current that can be measured.

In many embodiments, the photodiode output is amplified for further processing. To avoid amplifying ubiquitous 60 Hertz electromagnetic signals in the environment, careful design of the amplifier was found to be desirable for some embodiments. The noise equivalent power for the diode suggests a noise floor of less than 10 pA for the detector, so an amplifier that could work at such small currents is desirable for some embodiments. The amplifier circuit is described in more detail below.

Figure 14A:
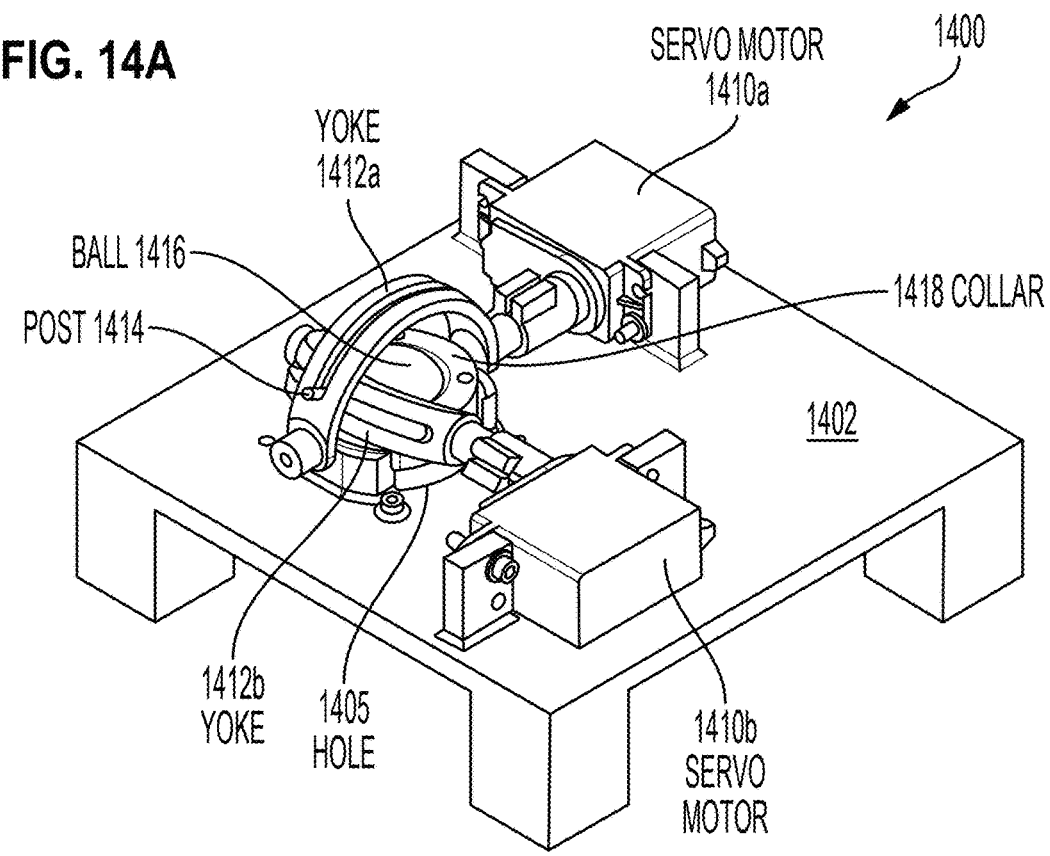
FIG. 14A through FIG. 14C are block diagrams that illustrate example test equipment used to demonstrate determining experimental orbital implant movement based on an light emitting implant marker and photodiodes arranged as on an ocular prosthesis, according to an embodiment.
Figure 14B:
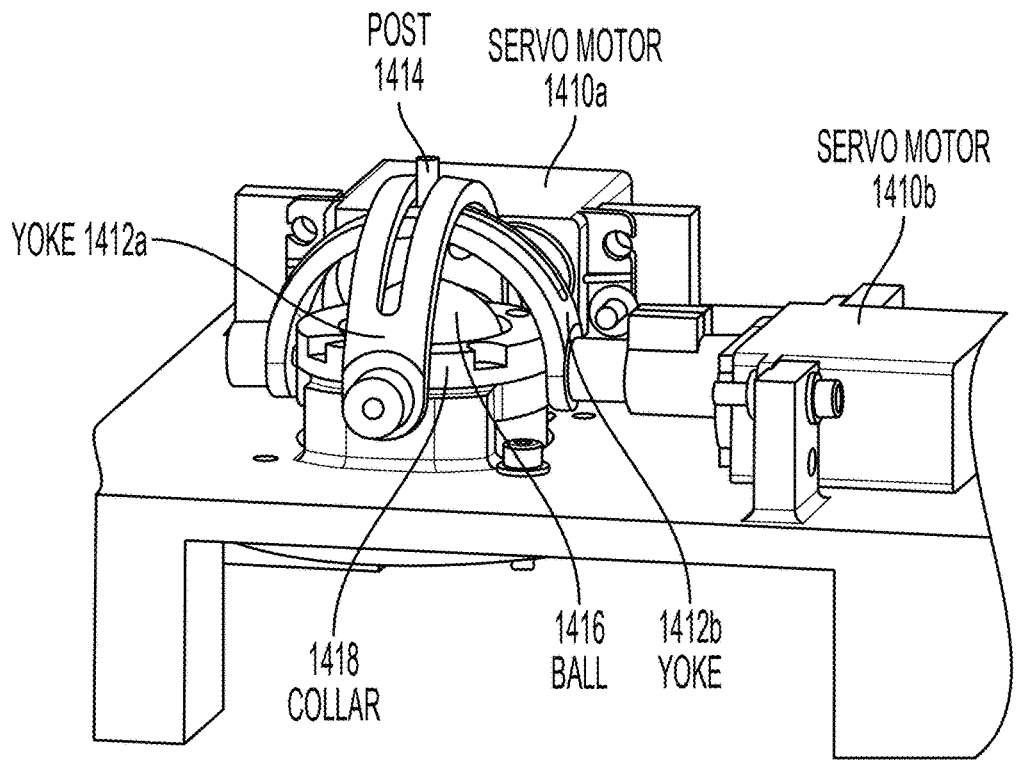
Figure 14C:
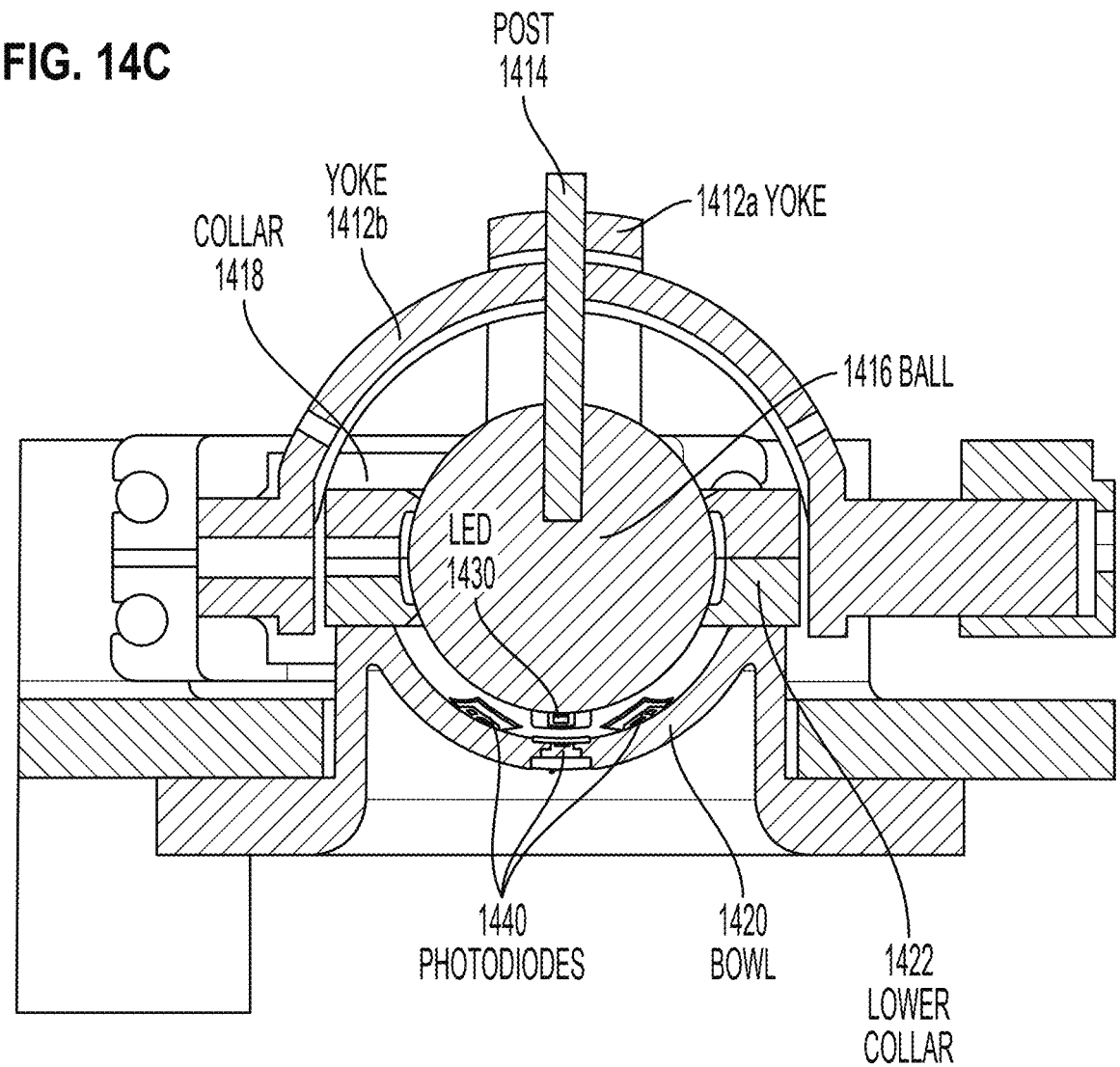

To evaluate the performance of various optical implant detector embodiments, a bench model was constructed as an experimental ocular prosthesis system to test measurements, circuitry and processing embodiments. This allows not only testing of position sensing methods, selection of appropriate optical sensors, and evaluation of signal-to-noise, but also allows the determination of achievable positioning accuracy. FIG. 14A through FIG. 14C are block diagrams that illustrate example test equipment used to demonstrate determining experimental orbital implant movement based on an light emitting implant marker and photodiodes arranged as on an ocular prosthesis, according to an embodiment. FIG. 14A though FIG. 14C are images rendered by a three dimensional computer aided design (CAD) software package called SolidWorks from Dassault Systemes SolidWorks Corporation of Waltham, Massachusetts operating on a general purpose computer, such a described below with reference to FIG. 21.

FIG. 14A is a block diagram that illustrates an example perspective view of the bench model 1400. Onto a bench 1402 with hole 1405 are mounted a first servo motor 1410a and a second servo motor 1410b that rotate a first Scotch yoke 1412a and a second Scotch yoke 1412b, respectively, around perpendicular axis representing horizontal and vertical rotations of an eyeball. Each driver translates from a pulse width modulated (PWM) electrical signal to a rotary position. A ball 1416 is placed above the hole and is constrained from moving upward away from the bench by a collar 1418. A post 1414 is attached to the ball and passes though slots in both yokes 1412a and 1412b. As the yokes 1412a and 1412b rotate when driven by the servo motors 1410a and 1410b, respectively, the post 1414 is pushed by the yokes to change orientation. The post 1414 is attached to the ball, so that when the orientation of the post 1414 changes, the ball 1416 rotates in response to operation of the servo motor 1410a or servo motor 1410b or both. FIG. 14B is a block diagram that illustrates an example different perspective view of the bench model 1400, showing the same elements described above. The rotation of the ball 1416 represents the rotation of the orbital implant 120 and is considered a experimental for the orbital implant in the following experimental embodiments.

FIG. 14C is a block diagram that illustrates an example vertical cross sectional view of the bench model 1400. The yoke 1412a, yoke 1412b, post 1414, ball 1416 and collar 1418 are as described above. A bowl 1420 is disposed in the hole 1405 and mounted to the bench 1402 from below. The upper curved surface of the bowl 1420 represents the posterior surface of the ocular prosthesis, and the bowl 1420 is considered a experimental ocular prosthesis in the following experiments. A lower collar 1422 disposed above the bowl is supported in place by the bowl 1420. The lower collar 1422 supports the ball 1416 and prevents the ball 1416 from falling through the hole or touching the upper surface of the bowl 1420. The ball 1416 is thus free to rotate between the lower collar 1422 and the collar 1418 as the ball is rotated by the post 1414 that is impelled by movement of the yokes 1412a and 1412b.

The implant detector system according to various embodiments is tested experimentally by disposing on the ball 1416 a LED 1430 as a glowing implant marker, and disposing along the upper surface of the bowl 1420 multiple photodiodes 1440. When the post is vertical, the experimental orbital implant is considered to be at rest as if a subject were staring straight ahead.

The Bench Model 1400 is built using a combination of Stereo Lithography (SLA) and Solid Printing. Both of these techniques are rapid prototyping methods that directly use the SolidWorks data files to produce the required mechanical pieces. The SLA method works in a liquid monomer vat. A laser polymerizes the top surface, creating a cross section of the desired object that is about 0.04" (0.1 mm) thick. This solidified layer is lowered just below the surface of the vat and the next layer is written by the laser. Repeating this process builds up the entire object in 0.1 mm steps. The Solid Printer works by jetting liquid polymer in layers onto a solid stage. This produces a smaller layer thickness, as thin as 0.0005 inches (0.012 mm), which yields a better surface finish and improved detail. The two printing methods permit different material choices including a variety of hard and soft plastics that can be either opaque or optically transparent.

The ball 1416 is a stock item that can be purchased in different materials ranging from Teflon to polycarbonate or ceramic. A hole gets drilled for the post 1414 which is also a stock item available in carbon fiber for a good combination of low weight and high strength Fasteners are stock plastic or steel items. Each yoke rides on two pivots: the driven end relies on the bearing inside the servo actuator; the free end is a steel pin (simple bushing).

To emulate a fluorescent dot, in some embodiments, the LED 1430 has a "frosted" plastic plug carrying a diffused light spot to the bottom surface of the ball 1416. This permits varying the optical power and periodicity as needed for the experiments. It was computed that only a few nanowatts of emitted power are sufficient for experimental embodiments, so the drive current applied to the LED is quite small. A small array of photodiodes 1440 is fitted to a upper surface of the bowl and then wired to an external circuit card that provides the electrical environment to energize the photodiodes and amplify their outputs. A high speed wide dynamic range data acquisition system borrowed from an FTIR infrared spectrometer was used to digitize the signals to values that were output to a spreadsheet form for analysis. In some experimental embodiments, the space between the bowl 1420 and ball 1416 is filled with saline solution to mimic the natural environment of the prosthesis.

The central photodiode was placed at the center of the upper surface of the bowl 1420, and the servo motors were used to drive the ball to various positions while measuring the detector response. The motor drives are quite accurate, so they provide a reproducible way of selecting exact positions.

For some bench test embodiments, a long lifetime green fluorescent material was used which was activated with a hand held ultraviolet (UV) lamp. The light output from this material decayed over a number of minutes, allowing the diminishing detector signals and the response at very low signal levels to be observed. A digital voltmeter (DVM) of a FLUKE™ multi-meter from FLUKE CORPORATION™ of Everett, Washington was used to measure the output of the detector circuit, manually recording the readings into an Excel spreadsheet.

FIG. 15A is a table that illustrates example variation of detected light intensity with angular separation between photodiode and light emitting implant marker, according to an embodiment. The two left columns 1512a and 1512b indicate a pair of X-positions for the motor driven ball using the first servo motor 1412a. "6000" represents the center position for the ball (the Y-axis using the second servo motor 1412b was always centered during this run). An excursion of 1000 counts represents 30 degrees of rotation. Each row 1514a through 1514v corresponds to a different step in the sequence of measurements. For each step of the sequence one reading was taken at center and another reading at some deflection angle. The digital voltmeter (DVM) readings are in microvolts and reported in columns 1512c and 1512d corresponding to X-positions in columns 1512a and 1512b, respectively. As can be seen from the "DVM at 6000" column, the light output of the fluorescent dot dropped significantly during the course of the data run. By the time the deflection of 7050 counts (about 32 degrees) was measured, the signal response had dropped off quite a bit. This is the expected result as it corresponds to nearing the local horizon as seen from the multi meter vantage point 3 mm from the surface of the ball.

In this experimental embodiment depicted in FIG. 15A, an input multiplexer is used to selects one of several photodiode inputs to be delivered to an analog to digital (A/D) converter for sampling. The maximum voltage is 720 μV which corresponds to 90 pA. The smallest voltage is 263 μV or about 33 pA input current. Almost all of this latter current is leakage from the multiplexer, not current from the photodiode. This bench circuit is stable to about 10 or 15 μV which equates to 1 or 2 pA. In this context, the 30+pA multiplexer current is seen to be a significant offset to the desired measurement. When this background (dark) current is subtracted from each reading, then the difference between the center (6000) and deflected (point) values indicate how much detector response is achieved.

Figure 15B:
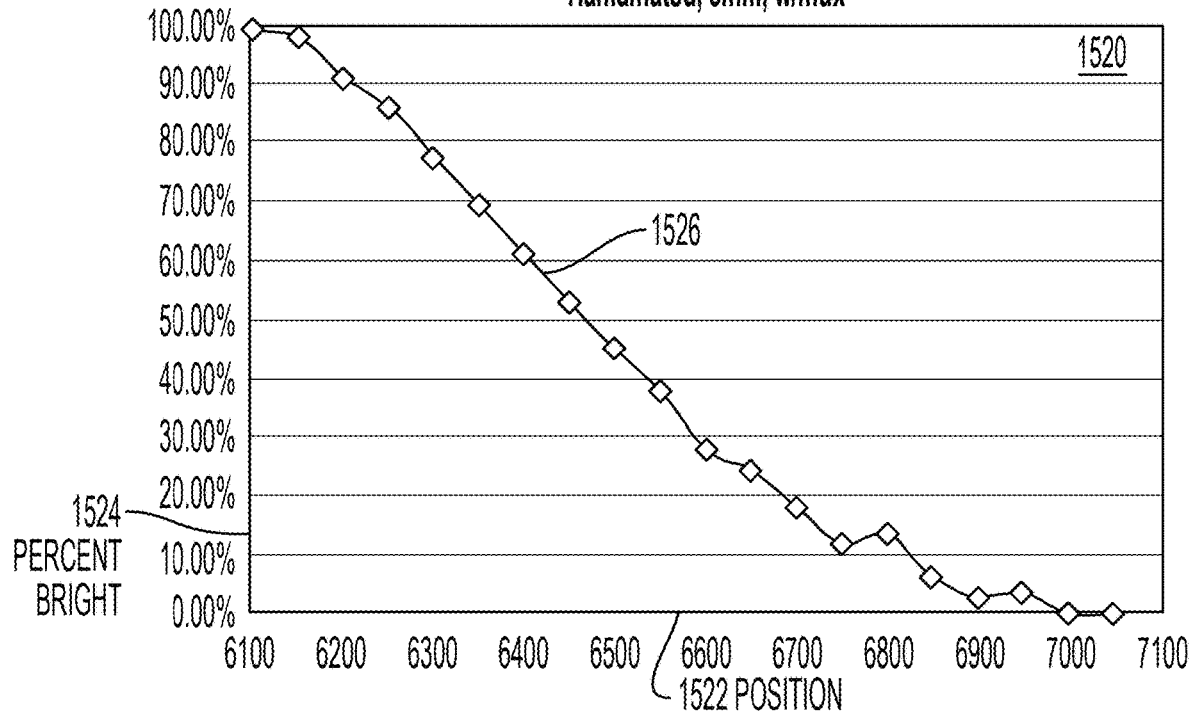

FIG. 15B through FIG. 15E are graphs that illustrate example variations of detected light intensity with angular separation between photodiode and light emitting marker on a experimental orbital implant, according to various embodiments. FIG. 15B is a graph 1520 for the deflection response with the multiplexer (mux) and including the subtraction step. The horizontal axis 1522 is X-position in servo motor step size. The vertical axis 1524 is percent brightness compared to the start of the experiment at a position directly in front of the glowing implant marker (e.g., the fluorescent dot). Trace 1526 indicates the response to deflection with the input multiplexer and the dark current subtracted out.

The data points of trace 1526 are 50 counts apart. This step size equates to just over one pixel at the display device. A rather linear response is indicated out to about position 7000 which represents 30 degrees deflection. The bump at 6800 was seen regularly which suggests it's an artifact such as a reflection. The response curve flattens at center and again as 30 degrees deflection is approached. Both behaviors are well predicted by the geometry of the ball and detector. But the nearly linear response is a surprise. The geometry suggests that the detector response should falloff much more sharply (in the order of distance squared) with increasing deflection. The linear response can be explained if reflections are occurring off the bowl or ball, or both. The energy from the reflections, while attenuated, combines with the energy from the direct path to produce a response that is proportional to distance, very much like the action of a waveguide. This linear response means that the detection system can work with less dynamic range than expected, thereby improving measurement quality, provided the conjunctiva over the orbital implant or the posterior surface of the ocular prosthesis, or both, are reflective at the wavelength of the glowing implant marker.

Figure 15C:
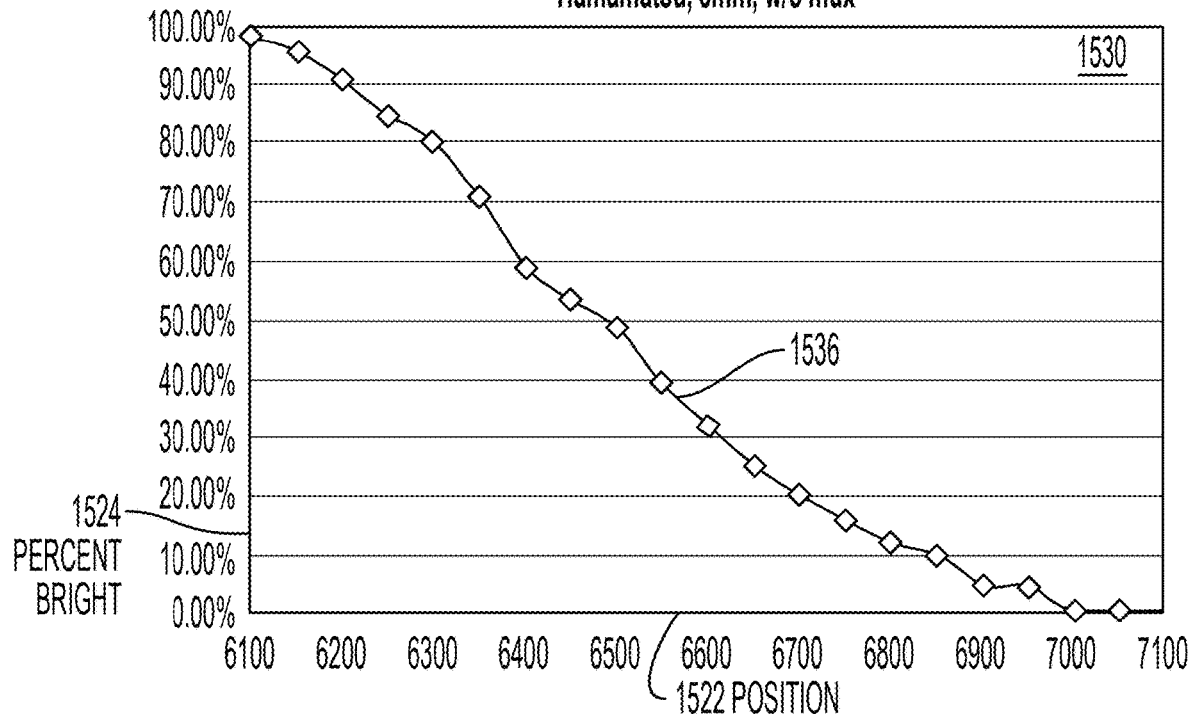

FIG. 15C is a graph 1530 for the deflection response without the multiplexer (mux). The horizontal axis 1522 and vertical axis 1524 are as described above. Trace 1536 indicates the response to deflection bypassing the input multiplexer to eliminate its dark current. The maximum measured current was about 45 pA in this experiment and the minimum was quite close to 0 pA. Removing the pedestal current from the mux improves the data slightly, but the qualitative result remains the same. It is easy to estimate the deflection to an accuracy of about one pixel.

FIG. 15D is a graph 1540 for the deflection response without the multiplexer (mux) and with 25% of the light used in FIG. 15C. The horizontal axis 1522 and vertical axis 1524 are as described above. Trace 1546 indicates the response to deflection with a weaker fluorescent source. Maximum detector current was about 15 pA in this experiment, hardly above the 10 pA noise equivalent power for the detector. The data are obviously not as good at this light level, but still quite usable.

FIG. 15E is a graph 1550 for the deflection response without the multiplexer (mux) using a different photodiode. The horizontal axis 1522 and vertical axis 1524 are as described above. Trace 1556 indicates the response to deflection with the ADVANCED PHOTONIX™ photodiode. Maximum detector current was about 38 pA for this experiment. The data are not qualitatively different from the Hamamatsu photodiode. This is an encouraging result since it indicates two different sources for the photodiodes of the optical implant detector.

Based on the results from the above experimental embodiments, the circuit components were determined for processing the output from various photodiodes in various embodiments.

Figure 16A:
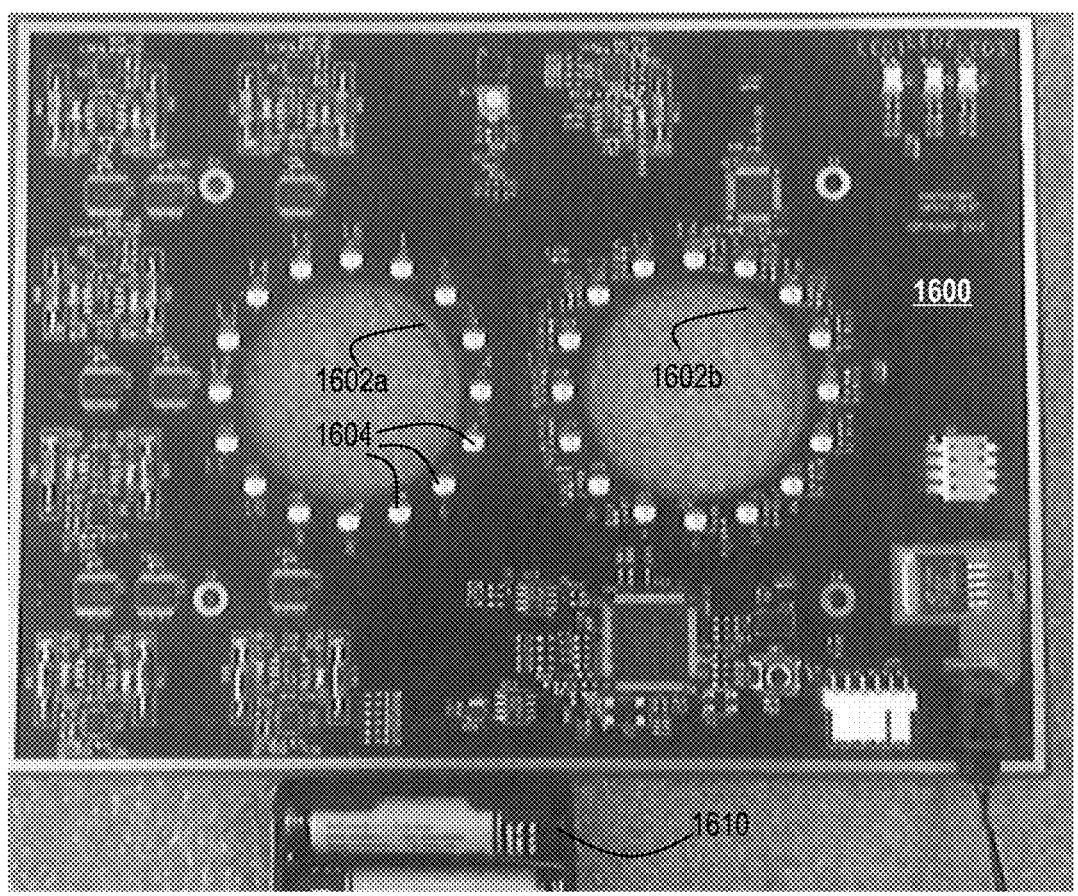
FIG. 16A is a photograph that illustrates an example test equipment circuit board configured to measure relative intensity at multiple photodiodes to determine orientation of the experimental orbital implant, according to an embodiment.

FIG. 16A is a photograph that illustrates an example test equipment circuit board 1600 configured to measure relative intensity at multiple photodiodes to determine orientation of the experimental orbital implant, according to an embodiment. The circuit board has two cutouts 1602a and 1602b so that it can mount to the mechanical model 1400 in either of two positions. The ring of objects around each cutout is the group of tiny coaxial connectors 1604 that bring in the photodiode signals from the bowl. This approach avoids a cost problems encountered with constructing prototype flex connectors to do the same job. The dual mounting locations allow exploration of two different circuit embodiments for the optical implant detector. Each circuit utilizes the same array of 16-photo-stmsors and the same single-chip computer to sample the results. The two circuits differ in the way the sensors get connected to the microprocessor. One circuit is optimized for highest performance, e.g., low leakage and best signal to noise. The other one is optimized for small size and low cost.

Figure 16B:
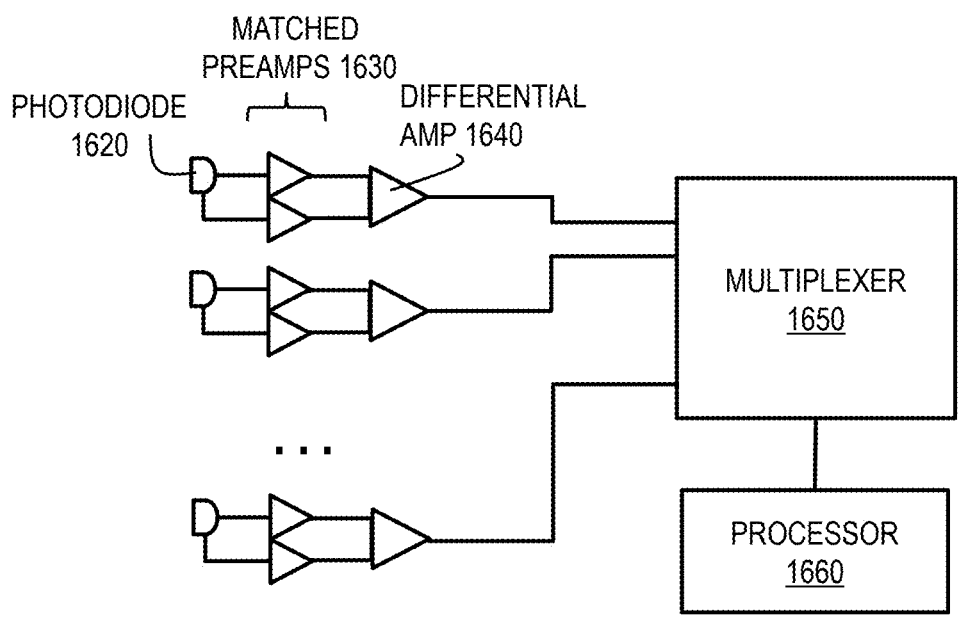
FIG. 16B is a block diagram that illustrates an example circuit on a circuit board of FIG. 16A configured to measure relative intensity at multiple photodiodes, according to an embodiment.

FIG. 16B is a block diagram that illustrates an example circuit on a circuit board of FIG. 16A configured to measure relative intensity at multiple photodiodes, according to an embodiment. In general, the circuit components include, for each photodiode 1620, a pair of matched preamplifiers 1630, a differential amplifier 1640 and a multiplexer 1650. Data from the multiplexer 1650 are processed by processor 1660 to determine deflection of the experimental (experimental) orbital implant. In various embodiments, processor 1660 is the same as the ocular prosthesis processor 301 or a separate processor in the implant detector 309, or some combination.

Dual matched preamps are built around a Linear Tech LTC6241CS8 device from LINEAR TECHNOLOGY CORPORATION™ of Milpitas, California Each input amplifier is a current-to-voltage converter that uses a 4 megaohm (M$\Omega$, 1 M$\Omega$=$10^6$ ohms) feedback resistor (actually constructed from four 1 M$\Omega$ resistors in a packaged array). This is the largest off-the shelf feedback resistor located. Ultimately this resistor sets both sensitivity and bandwidth. With the circuit as shown, sensitivity of 8 volts per μA of input current is achieved and a bandwidth of about 15 kHz. This is more bandwidth than is desirable to use; and, as the bench results show, additional sensitivity is desirable. In some embodiments, an even higher value feedback resistor is used to obtain more sensitivity at somewhat lower bandwidth. Note that the matched input preamps conspire to keep the photodiodes at zero bias voltage. Both ends of the photodiode get driven to a particular voltage designated Vcm but the differential voltage is quite small, essentially just the offset voltage of the preamps and multiplexer. This setup drives the photodiode dark current to essentially zero for best sensitivity.

Outputs of the matched preamps get summed in a unity gain differential amplifier. This removes common mode voltages to eliminate 60 Hz noise and other environmental electromagnetic contamination. The differential output of this amplifier can drive an analog to digital (A/D) converter or, in some embodiments, the experimental instruments. In the bench tests, it was found that the noise floor achieved by this configuration was quite low, permitting meaningful outputs in the low microvolt range. In other embodiments, more voltage gain is applied to this signal before driving an A/D converter.

A full array of detectors uses a multiplexer, such as multiplexer 1650, to connect various photodiodes to a measurement circuit. The ANALOG DEVICES™ ADG734BRUZ from ANALOG DEVICES INC.™ of Norwood, Massachusetts, is a suitable integrated multiplexer. In some embodiments, it is used in a T-switch configuration that keeps the detectors at the same bias point whether selected or not. This improves settling time as it switches from one detector to the next. The leakage current specification for the multiplexer is greater than a desirable 10 pA goal, so this affects the design of various embodiments.

The high performance/high cost/large size option uses full differential T-Switch connections. The multiplexer connects both terminals of the selected photodiode to a fully differential amplifier, as shown in FIG. 16B. This allows suppression of noise from external electrical sources. Each unconnected sensor has both terminals grounded. This prevents unwanted charge (photo-electrons) from accumulating during the "off" time of the sensor so there is no discharge or arcing when reconnecting to it.

The minimum acceptable performance option uses singled ended switch and amplifier. The multiplexer just connects the "hot" terminal of the selected photodiode to a single ended amplifier. All of the sensor ground terminals are connected to a common bias point. This is a simpler scheme with less noise rejection.

Testing revealed that the single ended switching matrix was too noisy to provide reliable data, so the results reported here are for the full T-switch implementation. Further tests indicate that the more advantageous feature of the complex multiplexer is its differential nature. The T-Switch feature (grounding each sensor when not selected) consumes half the resources of the multiplexer but adds little to signal quality.

Sensors are attached to the bench model circuit card using miniature coaxial cables and connectors. This is adequate for bench testing. In production embodiments, it is desirable to use flex circuitry to house the photodiodes and route their signals back to the A/D converter. In some embodiments, the multiplexer circuitry is distributed onto the flex circuit to minimize trace length and improve noise performance. This would likely make the production version of the sensor even more noise immune than the bench test embodiment of the circuit. The bench model sensor circuits have an input stage consisting of a current to voltage (I-V) converter (400 kiloohm, kΩ, feedback resistor, 1 kΩ=$10^3$ ohms) and a voltage gain stage (16 fold gain) for an overall gain of 6.4 volts/μA. The KINETIS central processing unit (CPU) processor, from FREESCALE SEMICONDUCTOR INC.™ of Austin, Texas, has an A/D converter with 1.2 Volts input range and (effectively) 12 bit resolution. This makes one least significant bit (LSB) at the A/D converter equal to 46 pA at bandwidth that is approximately 15 kHz. Settling time is limited by the photodiodes which are operated at zero bias voltage in order to minimize dark current. The photodiodes develop their maximum capacitance (typically 100 pF) at zero bias, so the resistor-capacitor (RC) circuit time constant developed via the preamp feedback resistor is 100 pF×400 kΩ=40 μs. This is validated by the desirable settling time of 160 μs (four RC time constants=98% settling) before taking each sensor measurement.

Figure 17A:
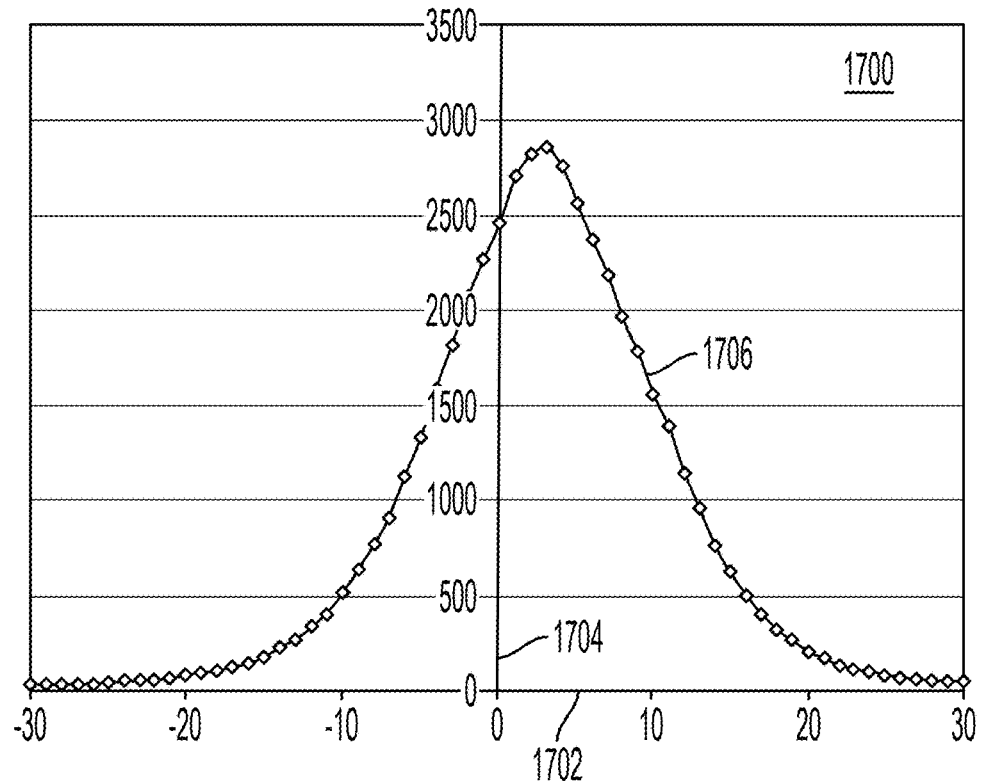
FIG. 17A and FIG. 17B are graphs that illustrate example variations of detected light intensity with positive and negative angular separations between photodiode and light emitting marker on an experimental orbital implant using the circuit of FIG. 16B, according to various embodiments.
Figure 17B:
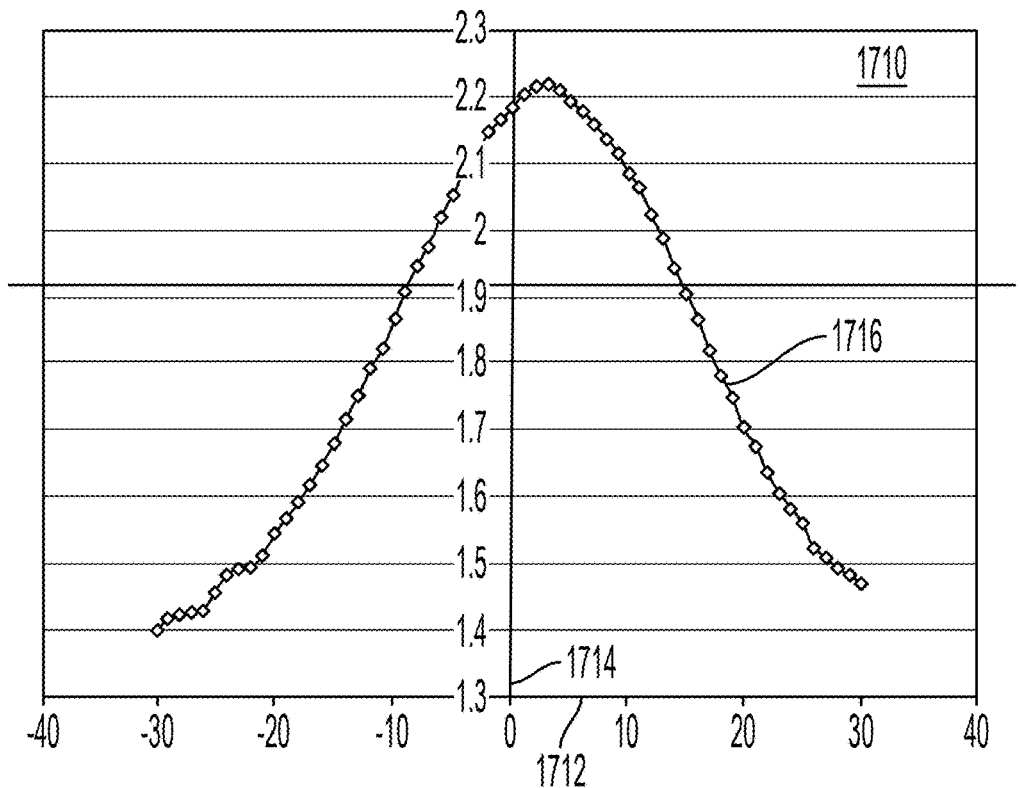

Static measurement were obtained by moving one axis of the servo while collecting optical sensor output from a microprocessor. FIG. 17A and FIG. 17B are graphs that illustrate example variations of detected light intensity with positive and negative angular separations between photodiode and light emitting marker on an experimental orbital implant using the circuit of FIG. 16B, according to various embodiments. FIG. 17A is a graph 1700 that illustrates example results from an embodiment of an experimental setup. The horizontal axis 1702 is deflection angle in degrees. The vertical axis 1704 is photodiode circuit response in counts (arbitrary units). Trace 1706 depicts the measured response of the high performance circuit to deflection of the experimental orbital implant. Note that the peak intensity is not at the center of the plot. This just indicates that the zero point of the servo motor system isn't directly in the center of the sensor array. Trace 1706 shows that sensor response is non-linear, falling off rapidly with distance, which is the expected result. If our light source (an LED) were a homogenous radiator, the intensity would fall off as distance squared because the detector is of constant size and the surface area of a sphere is proportional to radius squared. In the experimental embodiment, the LED is mounted on a sphere which is rolling away from the sensor. As the light source nears the local horizon, intensity falls rapidly to zero. This leads to another nonlinear term which probably behaves as distance to the power of x, where x is different from 2 and determined by experiment. Hence the overall distance vs. intensity relationship is a high order exponential function.

FIG. 17B is a graph 1710 that illustrates example results from an embodiment of an experimental setup with intensity raised to the 0.1 power. The horizontal axis 1712 is deflection angle in degrees. The vertical axis 1714 is photodiode circuit response intensity raised to the 0.1 power. Trace 1716 depicts the measured response of the high performance circuit to deflection of the experimental orbital implant. This data transform makes the plot look almost linear. The real lesson from this graph is that, even though the intensity values near+−30 degrees are small, they are still changing in a way that allows useful deflection data to be derived from the optical experiment. This makes it clear that these sensors can be used for triangulation of the light source.

Signal to noise ratio (SNR) for these measurements is good. In some embodiments, the KINETIS™ A/D converter is configured to take more than one input sample (5 μs each) per digital output. When 16 samples are taken per reading (80 μs) the signal has a standard deviation of 1.3 counts and a peak deviation of about 5 counts. This amounts to 10 or 11 bits of useful information from the A/D converter at a typical illumination level (about 100 nA maximum at the photodiode). Good triangulation can also be obtained with lower SNR than this if illumination intensity is reduced or the observation period is shortened. It takes about 160 vs for the signal to settle after a change in the multiplexer setting, so the present 80 μs observation period results in 240 μs per multiplexer setting or about 4 μs to scan the entire array of 16 photodiodes.

From the standpoint of power consumption, it is advantageous to shorten the total observation time so that the circuitry can spend more time in sleep mode. This is accomplished, in some embodiments, by first making a fast scan of the photodiodes (50 μs each) and then returning to the brightest three or four for a closer look (240 μs each). In this way, the total time is reduced to less the 2 ms or about 4% of the approximately 50 ms frame time (20 Hz display refresh rate).

It was found that the optical sensor works nearly equally well with saline or air in the gap between the LED and the sensor bowl. Actually, sensor intensity is a bit better with the saline in place. The data collection algorithm makes an estimate of the dark current (background) from each sensor. In some embodiments, the background gets subtracted from the foreground value to obtain an intensity figure.

The sensor array is strongly affected by ambient light, for instance fluorescent lighting with its 120 Hz oscillations. So it is advantageous to provide some shielding from a bright environment. This should be provided by the prosthesis itself, in some embodiments. Small amounts of light leakage are tolerated well. It was determined that whenever the LED is activated, the entire ball 1416 glows somewhat. This background glow amounts to about 15 counts at the A/D converter compared to peak intensities of 3000 counts. The glow gets treated as background signal so it does not affect the deflection computation.

The basic components of the circuit of FIG. 16B, such as microprocessor, sensors, multiplexers, and amplifiers are suitable for operation at extremely low power levels of the ocular prosthesis. Thus, it is useful to take a look at steady state power consumption to see what it implies about battery life. FIG. 16C is a table that illustrates example power consumption of various components of the optical sensor circuitry, according to some embodiments. The table of FIG. 16C shows that the example circuit typically consumes about 90 mA in its active mode. This was confirmed by direct measurement of 85 mA active current. Power consumption falls into the low micro-amp range when the circuit is in sleep mode (not sampling the sensors). With powered up active time at 4%, in some embodiments, this circuit consumes about 3.6 mA on average. Power consumption is further reduced, in some embodiments, by using a smaller number of sensor amplifiers. The illustrated design minimizes the number of multiplexers (to improve SNR) at the cost of extra amplifiers, but this precaution did not provide a great advantage. Since the multiplexer chips consume almost no power, the larger multiplexer is preferred. This reduces power consumption by about 30%.

The largest power consumer is the KINETIS™ K10 processor which is operating at 100 MHz. This chip has a lot of on-board resources including 512 kilobytes (kB, 1 kB=$10^3$ bytes, 1 byte=8 bits) of Flash memory, so it consumes quite a bit of power. For sensor handling alone, the power consumption is cut quite a bit. A typical figure for a small processor configuration is 160 μW per MHz which would lead to an active current consumption of just 5 mA and an average current consumption of about 200 µA. A major contributor to processor power consumption is the computation used to form the image for the display device. The amount of memory and the number of computational cycles used to update the display every frame (about 50 ms to 60 ms) will dictate how much CPU capability is included in various production embodiments. Efficient algorithms for display device updates conserve power in order to optimize battery life.

The present figure of 3.6 mA average for the entire circuit is near the maximum for our planned batteries. Current to the LED beacon was measured at 1.65 mA peak, which, using a 4% duty cycle, consumes on average about 66 µA. This is well within the power budget for illumination. In some embodiments, this power is delivered via radio frequency transmission, which is somewhat lossy. However a ten-fold power loss does not pose a threat to battery life.

Figure 18A:
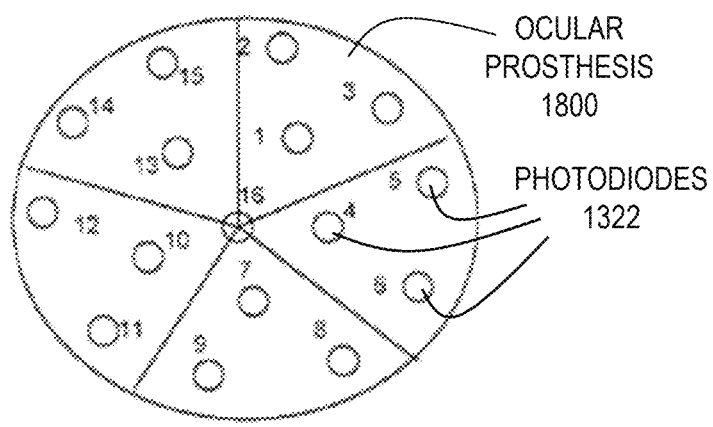
FIG. 18A is a block diagram that illustrates an example arrangement of photodiodes to detect motion of a experimental orbital implant with a light emitting marker, according to an embodiment.

FIG. 18A is a block diagram that illustrates an example arrangement of photodiodes to detect motion of an experimental orbital implant with a light emitting marker, according to an embodiment. A photodiode is disposed at the center, five photodiodes are disposed equally around at about the 30 degree circle, and ten photodiodes are disposed equally around at about the 60 degree circle. Both qualitative and quantitative measurements for dynamic performance of the optical implant detector were favorable.

The qualitative evaluation used the servos to "play back" an actual eye motion file supplied by MSKCC personnel. Real time position data from the sensor array were collected during playback. Using a personal computer, a human face was displayed with two computer driven eyes. One eye was driven by the original eye motion file that drove the servo motors of the bench model, and the other eye was driven by the sensor data from the bench model eye. When the eye is moving slowly or is at rest, the position sensor solution oscillates between two adjacent pixels. This is expected for any practical sensor, but it produces a jittery looking eye display. An anti-jitter algorithm was implemented to suppress small changes that were non-repeating; and, this step removed the display artifact. Even though the servo motors were fairly powerful, rapid eye motions (cycads) produced such high velocities that the servo motors were unable to keep up. This produced a small amount of lag which was visible on the two eye display. However this is not a problem for a production embodiment in which the orbital implant is driven by the subject and not by servo motors.

A quantitative test included stepping the servos through every possible position of the mechanical eye, taking multiple sensor measurements at each position. This data was imported into Excel spreadsheets and used to generate plots. While the servo was making 1 degree steps in the X-axis, 9 separate readings of the 16 sensors were taken at each position.

As expected, these data show some scatter. The sensitivity of the PIN diode photodiode array changes with position. When the LED beacon is located directly beneath one of the 16 PIN diode photodiodes, there is excellent signal amplitude and position sensitivity. When the LED is equidistant from the three nearest sensors (in the middle of a triangle), signal amplitude and position sensitivity are both reduced. The Euclidian distance between the sensor readings for adjacent servo positions are measured. This gives a sensitivity measure. Comparing the sensor uncertainty to this sensitivity gives a metric for accuracy.

Figure 18B:
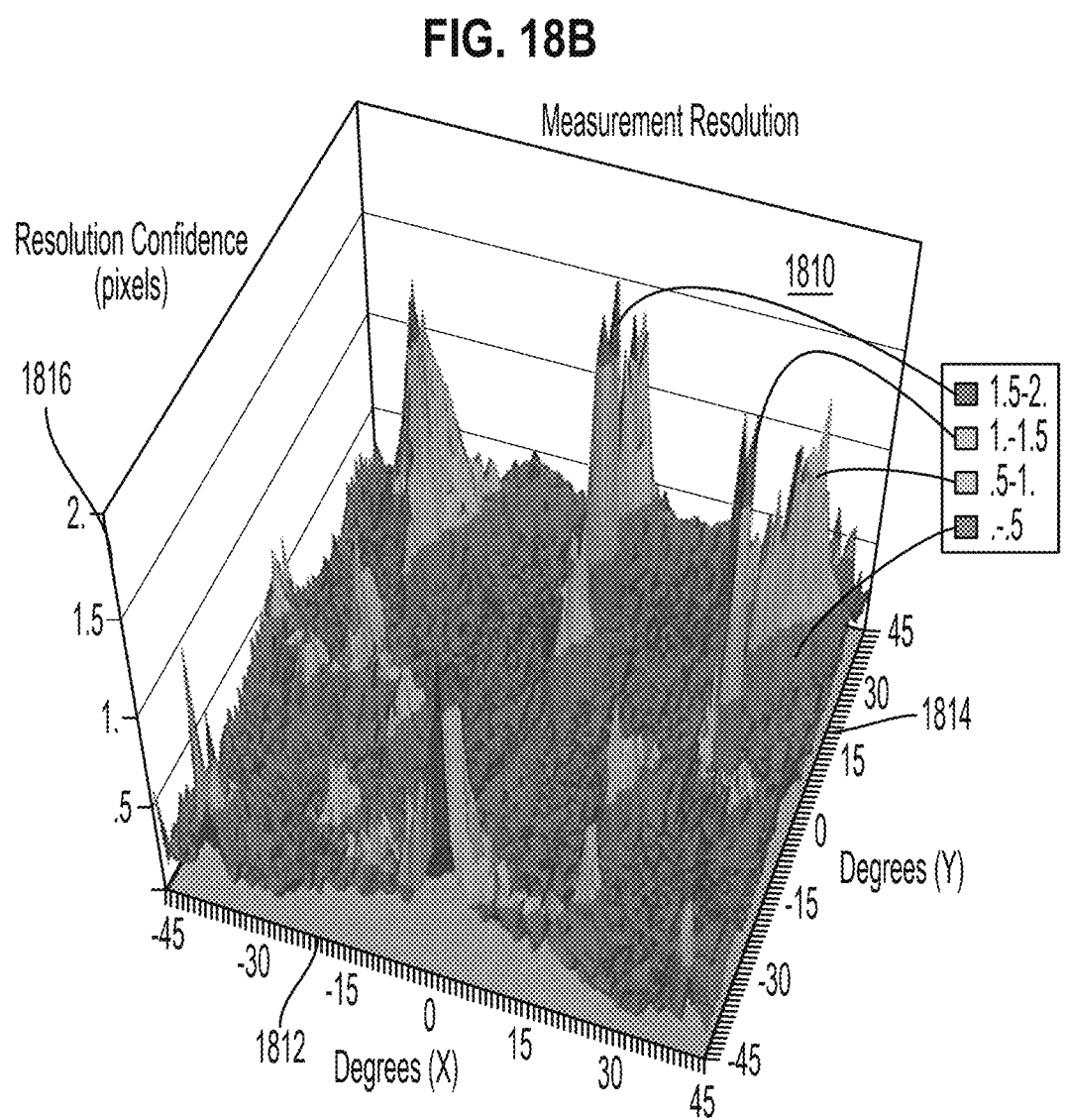
FIG. 18B is a graph that illustrates example orientation confidence for the experimental orbital implant using the photodiode arrangement of FIG. 18A, according to an embodiment.

FIG. 18B is a graph that illustrates example orientation confidence for the experimental orbital implant using the photodiode arrangement of FIG. 18A, according to an embodiment. The x axis 1812 indicates deflection in the X-direction in degrees (e.g., from rotation of the first servo motor 1412a). The y axis 1814 indicates deflection in the Y-direction in degrees (e.g., from rotation of the second servo motor 1412b). The z axis 1816 indicates the resolution confidence (in number of position elements, called pels hereinafter) at the combined deflection. Most of the surface enjoys good confidence (less than 0.5 pels) indicated by the dark regions at low elevation. This level of accuracy provides very secure position data. There are spots of moderate confidence (0.5 to 1 pels) indicated by the lighter regions. A few combinations lead to noticeable errors (1 to 1.5 pels). A few peaks indicate the largest errors of 1.5 to 2 pels.

Figure 19A:
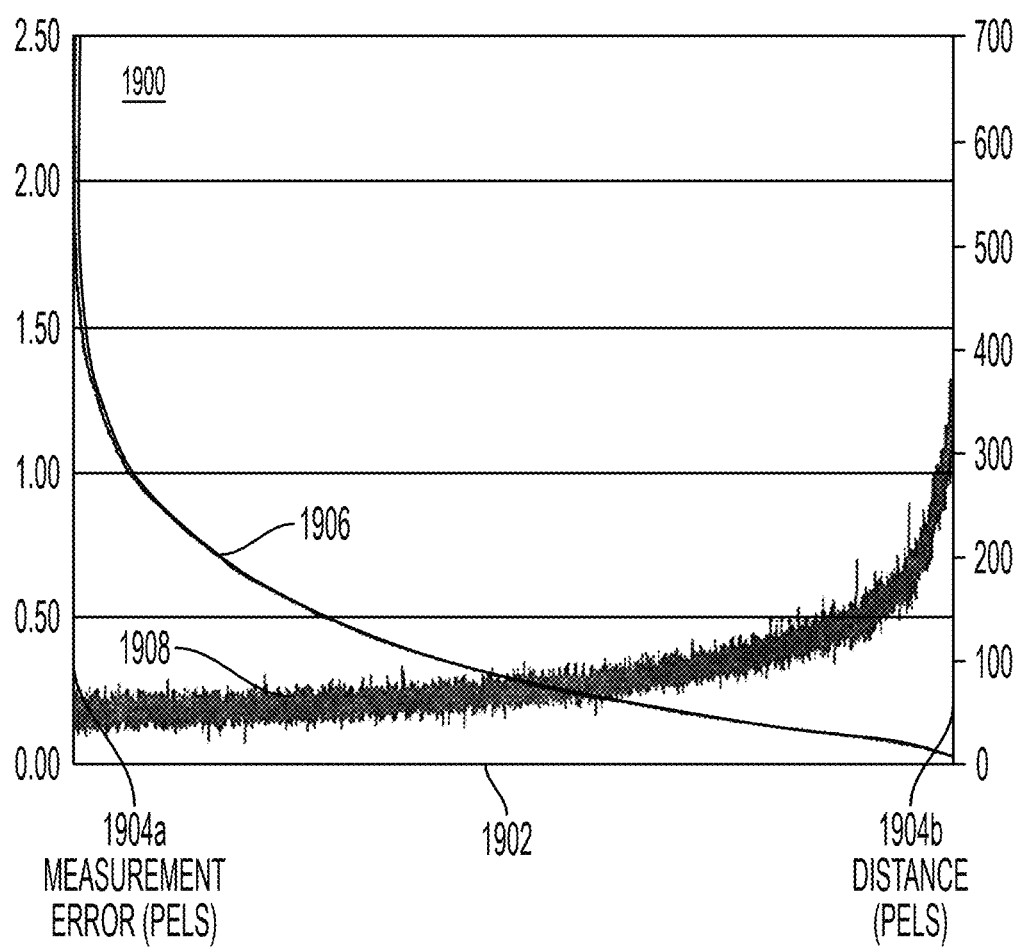
FIG. 19A and FIG. 19B are graphs that illustrates example distributions of errors with distance between light emitting marker and photodetectors used to triangulate position of the marker, according to an embodiment.
Figure 19B:
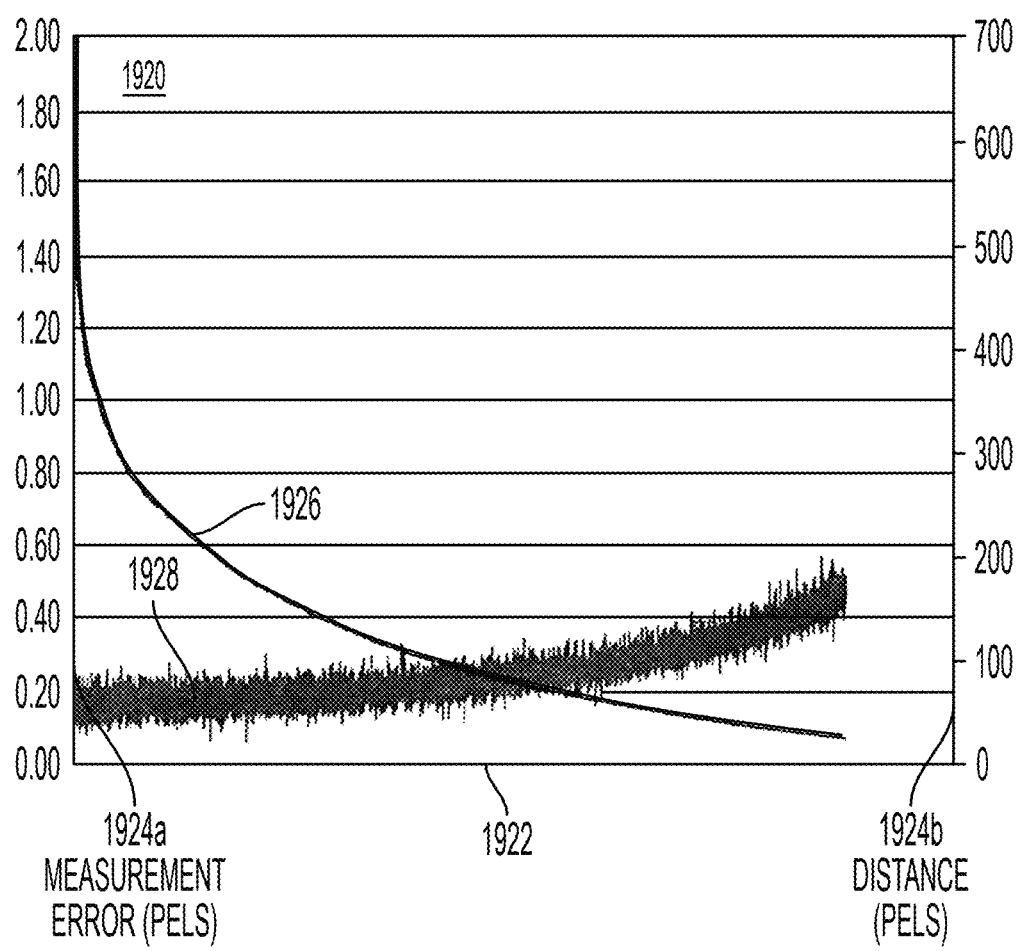

FIG. 19A and FIG. 19B are graphs that illustrates example distributions of errors with distance between light emitting marker and photodetectors used to triangulate position of the marker, according to an embodiment. FIG. 19A is a graph 1900 that illustrates example data points sorted by nearest neighbor distance (NND). NND is a Euclidian measure across the 16 sensors, summing the square of each sensor distance (in pels), then taking the square root of the sum. The horizontal axis 1902 represents different positions (orientations) for the experimental orbital implant. The right side vertical axis 1904b indicates the nearest neighbor distance in pels. The left axis 1904a indicates the position error in pels. Trace 1906 is the NND, according to which the data are sorted; and, therefore, trace 906 decreases continually from left to right. Trace 1908 indicates the error, which varies between adjacent sorted positions by about 0.1 pels. When the sensitivity is at its best (right near or under a PIN diode) the NND distance is large (over one hundred pels, the measurement error is less than one quarter pel. The minimum NND is nearly constant throughout the motion field, averaging about 15 pels. As trace 1906 declines to about this level, the error trace 908 increases to about one pel.

FIG. 19B is similar to FIG. 19A but with 10% of the positions with the lowest sensitivity removed. This amounts to moving the sensors 10% closer together. This result shows that by placing the sensors a bit closer together (might require 19 instead of 16 PIN diodes) all of the possible eye positions have accuracy better than 1 pel.

It is noted that the bench model test embodiment used+/− 60 degrees total range in both the horizontal and vertical axes for simplicity in construction. The production embodiment of this sensor array implements a reduced vertical deflection (e.g., about 45 degrees vertical deflection) to mimic the human eye. The same number of sensors then allows closer sensor spacing. This would further improve SNR since the optical signals improve rapidly with shorter distance, as indicated in FIG. 19B. In some embodiments, 21 sensors disposed in three rings of 3, 6 and 12 are used instead of the 16 sensors disposed at the center and in two rings of 5 and 10, described above.

In some embodiments, the implant detector 309 includes a practical circuit to drive the proposed LED implant marker. In some embodiments, this circuit uses a radio frequency (RF) transmitter. In these embodiments, the implant marker includes the LED, and an LED power source that includes, at least, a receive antenna. The RF driven LED is optimized for low power consumption, small size, and a short transmit distance. It is advantageous in various embodiments that the RF transmit antenna is also used for other purposes, such as in the communications module 313, or as the inductive coil for an inductive charger in charge receiving device 305 to replenish the on-board battery 303, or some combination. In some embodiments, the receiver in the implant marker is a dipole antenna which would respond to electric fields but not to magnetic fields (to avoid being over-driven by the magnetic fields in an MRI machine).

2.4 Ambient Light Sensor

Some embodiments include an ambient light sensor 307. In some embodiments this functional block includes a phototransistor and associated circuitry to filter, amplify and bias the output of the circuit to produce an analog voltage proportional to the ambient light level averaged over the normal human visual range. In some embodiments, the optics include appropriate optical filters to approximate the human visual response. The circuit output is interpreted by an A/D converter, which, in some embodiments is a peripheral sub-block of the CPU that serves as processor 301. The technology, circuitry and components are well known. The packaging and assembly aspects of this functional block are described in a later section with the packaging of the other components. One unique challenge relevant to this functional block is how light will reach the phototransistor. In various embodiments, the phototransistor is mounted at the prosthesis anterior surface, or a light pipe or optic fiber channels light from the anterior surface to the sensor. Because the display device covers much of the visible surface, a least visually intrusive configuration is chosen, such as a sensor under the eyelid outside the display device, or a fiber port that appears red, such as part of a blood vessel naturally seen on a sclera portion of an image or fixed background. In some embodiments, the surface location is in the area of the tear duct. The light sensor is expected to not significantly impact the power budget or battery life.

2.5 Processor

Various embodiments include a processor 301, of minimal or powerful capacity. In some embodiments, ultra-low power microcontrollers from different manufacturers are used, such as processors that have current consumption of 120 µA to 1000 µA per million instructions per second (MIPS). The MSP430 family from TEXAS INSTRUMENTS™ of Dallas, Texas, has a nominal current draw of 165 µA to 400 µA per MIPS depending on the configuration and peripherals. The microcontrollers from STMICROELECTRONICS™ of Geneva, Switzerland draw 195 µA to 233 µA per MHz depending on architecture.

In some embodiments, 20 FPS (frames per second) is achievable with readily available microcontrollers operating at 1 MHz with one instruction execution per clock cycle, or 1 MIPS. For a typical CPU consuming 300 µA per MIPS and operating directly from the battery voltage, this would consume about 20% of the power budget. In some embodiments, CPU speed is increased to increase processing bandwidth to support a higher frame rate, but power consumption would also rise proportionately.

In an experimental embodiment, the FREESCALE KINETIS K10 was used. This CPU is housed in a rather large package that isn't suitable for integration into a production prosthetic, but it provides resources that were useful in the bench model.

In some embodiments, the Freescale KL02 CSP microprocessor is used as the CPU. The device contains 32 KB Flash memory, 4 KB RAM, a 32 bit ARM core, and a 12 bit (effective) multi-channel A/D converter. The package is just 2×2 mm and supports 18 input/output pins. The optical sensor multiplexor is built from 5 enables and 5 A/D channels, permitting us to sample 25 different input signals. An optical array that uses 3-6-12 sensor rings consumes a total of 21 inputs. An additional optical channel handles the ambient light sensor, leaving three channels available for housekeeping functions such as battery management. By supporting 21 position sensors (instead of the 16 found in the earlier bench model) improved position detection and better utilization of the optical beacon are both achieved.

2.6 Memory

Memory is cheap and small but does consume power. The amount of memory depends on the configuration data and software instructions in various embodiments. In some embodiments, the amount of memory is strongly affected by the storage of images associated with different pupil dilations. The range of pupil dilations is approximately 2 to 6 mm. This equates to about 6 to 20 pixels. If a separate eye image for every 1 pixel change in pupil diameter, in some embodiments, then 15 images are stored. There are several methods of storing the eye image in memory.

In one set of embodiments, an iris image on an oversize sclera field is stored so that as the image pans left-right and up-down, the off-screen sclera image portion scrolls into view, as depicted in FIG. 9C. In some embodiments, the image size used for this image is twice the height and twice the width of the display area, which is four times the display size. In some embodiments this is 3380*4=13,520 pixels. The memory size at 2 bytes per pixel is 27,040 bytes.

In another set of embodiments, the eye image wraps around as the eye pans left to right and blanks as the eye pans up and down. The image size for this case is the same as the display size, 3380 pixels. The memory size is 6760 bytes.

In another set of embodiments, the sclera features are static and only the rectangular iris area is stored as an image, requiring 3380/2=1640 pixels. The memory size is 3380 bytes.

In another set of embodiments, the images are folded along the vertical and horizontal axis centered on the pupil so that only one quarter of the image is stored, thus reducing the image and memory sizes in cases 1 thru 4 to 25% of their unfolded size. The memory size for case 3 becomes 845 bytes.

In another set of embodiments, a 2 color scheme is used with a 4-bit color depth; and, only one byte per pixel is stored and the memory size for case 4 becomes 423 bytes.

In various embodiments, computer cycles are traded for memory size. That is, the 4× folded image takes up a less storage space, but it requires the CPU to unfold the image while updating the display. In some embodiments, the onboard memory of the CPU chip, typically 128 kB is used for the combination of program and image storage. It is estimated that, with this much memory available in some embodiments, the image construction algorithm supports 20 frames per second at 1 MIPS computational rate.

2.7 Communication Module

In various embodiments, communication module 313 is used for device configuration and programming through optical or RF means. The optical approach suggests itself because an ambient light sensor is already included in some embodiments. Thus in some embodiments, a second use is made of this sensor as an optical data receiver, although it would not be spectrally compatible with the Gas LEDs used in typical hand held optical programming devices (such as television remote controls). In some embodiments, an optical transmitter is added for a secure (verifiable) communication loop. The optical transmitter might represent a significant power sink.

In other embodiments, one or more of a number of radio frequency communication standards are used, which already target short range communication, medical devices, and very low power consumption. Additional RF circuitry is included in these embodiments. The RF antenna itself should not be problem and in various embodiments is shared with one or more other components. For example, in some embodiments, the electrodes inside the battery are driven as an antenna. Given the inherently low power consumption of these RF links and the intermittent need for communication (only during setup) the power consumption should not be an issue in these embodiments.

2.8 Housing Form Factor

Figure 20:
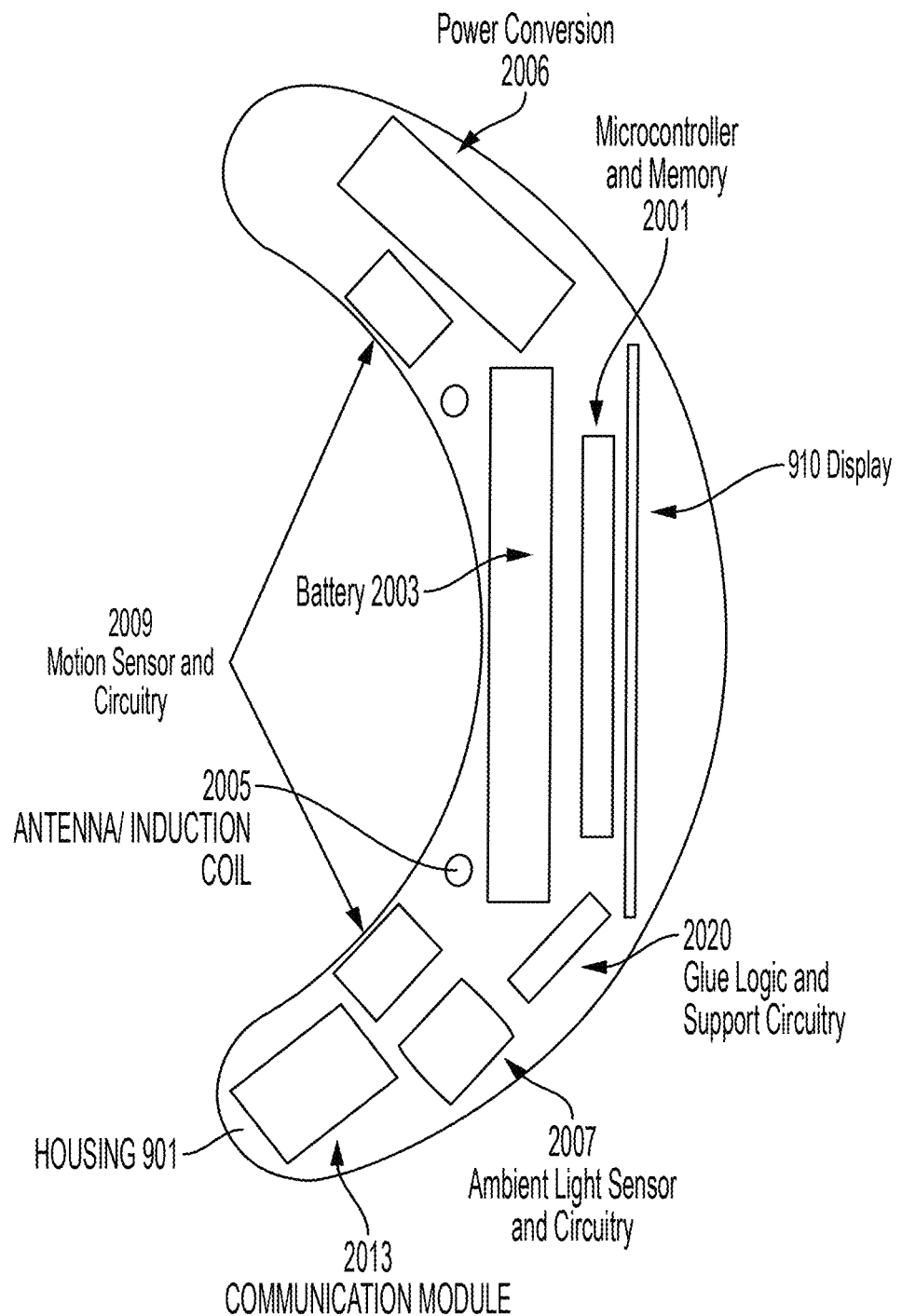
FIG. 20 is a block diagram that illustrates example disposition, in a vertical cross section, of components of an ocular prosthesis in a housing with a form factor suitable for insertion as an ocular prosthesis under an eyelid of a subject and anterior to an orbital implant, according to an embodiment.

FIG. 20 is a block diagram that illustrates example disposition, in a vertical cross section, of components of an ocular prosthesis in a housing 901 with a form factor suitable for insertion as an ocular prosthesis under an eyelid of a subject and anterior to an orbital implant, according to an embodiment. In a vertical cross section of the housing 901 are shown the display 910 serving as display device 311; a microcontroller and memory chip 2001 serving as processor 301; a battery 2003 serving as power storage/supply 303 and induction coil 2005 serving as charge receiving device 305 and a power conversion module 2006 all serving as power source 302, an ambient light sensor and circuitry 2007 serving as light sensor 307, a communications module 2013 and antenna/induction coil 2005 serving as communications module 313; and motion sensor circuitry 2009, such as an array of 16 photodiodes and circuitry, including part of microcontroller and memory 2001 serving as implant detector 309. Also shown is glue logic and support circuitry 2020 that helps connect the various components and control access to various functions, such as microcontroller 2001 and power from battery 2003 and use of antenna/induction coil 2005.

In some embodiments, the microcontroller and other larger semiconductor devices are die level assembled to minimize the volume penalty of the electronics packaging. While this is the most space efficient implementation of the electronics, it presents other costs and complexities in handling, assembly methods and testing. The microcontroller investigation revealed newer types of "wafer scale" packaging as small as 1.7 mm×2.9 mm×0.6 mm for an 8-bit ST Semiconductor microcontroller in a WLCS28 package. Since this is a standard packaged configuration, it has significant logistics and manufacturing benefits over a bare die, and still with a small volume penalty. Thus, such wafer scale packaging is used in some embodiments. Some embodiments use bare die components and assembly methods for some components but not others.

FIG. 20 illustrates a concept rendition for the ocular prosthesis depicting representative functional block volume models encapsulated in a housing 901 made of a castable medium, such as acrylic resin. Table 1 shows the volume demand by functional unit.

TABLE 1

Volume estimates by functional block.

| Component/ Functional block | Length (mm) | Width (mm) | Thickness (mm) | Volume (mm³) | Notes |
|---|---|---|---|---|---|
| Battery | 19.0 | 10.8 | 2.4 | 492.5 | |
| Power conversion | 6.0 | 6.0 | 2.5 | 90.0 | |
| Display | 28.0 | 13.0 | 0.1 | 31.8 | |
| Microcontroller | 4.0 | 4.0 | 0.6 | 4.6 | |
| Ambient light sensor | 2.2 | 2.2 | 2.0 | 9.7 | |
| Motion sensor circuit | 2.0 | 3.0 | 0.8 | 4.8 | x 16 |
| Support circuitry | 3.0 | 3.0 | 0.5 | 4.5 | |
| Total Volume | | | | 709.9 | |
| Estimated available volume | | | | 2800.0 | Large prosthesis |
| | | | | 1800.0 | Small prosthesis |

As evident in Table 1, the battery volume dominates the space available. Since the electrolyte in lithium polymer battery chemistry is entrained in a flexible solid material (polymer), it has the unique property that it can be curved or easily shaped into irregular forms. This characteristic of these batteries is highly beneficial in gaining space in some embodiments.

In some embodiments, the bill of materials (BOM) is dominated by the cost of the display device. Estimates for the other electronic components (CPU, battery, power conversion circuits, position sensor, light sensor, etc.) total approximately $100 at the time of this writing. However, purchasing a custom display in very small quantities (compared to consumer displays such as cell phones) is relatively expensive. The initial cost for the display is on the order of $1,000 for some embodiments at the time of this writing. It is expected that this cost will drop as flexible reflective display technology becomes more commonplace.

Some embodiments are expected to involve somewhat exotic assembly methods. The fabrication costs are highly dependent on manufacturing volume. At an anticipated volume of 10,000 units annually, a fabrication cost at the time of this writing is expected to be in the range of $100 to $200 per unit.

None of the characteristics of the components of the ocular prosthesis present an obstacle to generating various embodiments, Thus, a variety of embodiments are currently feasible, and individual components, such as a display and implant detector have been thoroughly demonstrated.

2.9. Spatial Packaging Model

Packaging of the electronic circuitry, battery and display to fit within the allowed space in the prosthesis was addressed with a more detailed spatial packaging model, described here. Elements of the circuit design and component selection were described in previous sections. An advancement in circuit design has been to place a tiny amplifier directly adjacent to each optical sensor of an implant detector. This amplifier produces a more robust signal that should be able to reach an analog to digital converter (ADC) in the microprocessor without further signal conditioning. A 25 element (5×5) signal multiplexer was implemented using a sleep mode of the amplifier (5 selection signals) and five ADC input channels on the central processing unit (CPU) chip. In order to test this concept under realistic conditions, a flexible printed circuit was built that is faithful to the dimensions of the optical prosthetic. The sensor signals are somewhat fragile and can't be transmitted noise-free over long distances.

A solution to the optical sensor/multiplexor problem is predicated on making a very compact circuit to not suffer from the electrical noise that would result from long circuit traces. One solution is to construct the bulk of the circuit using flexible circuitry that is very close to the eventual production implementation. A flexible circuit "spider" commits an arm to each optical sensor. The endpoint of the arm carries a photodiode and its supporting amplifier. Outgoing signals from the circuit down each arm include power and enable; the returned signal includes a voltage representing the light input to the photodiode. By placing each optical sensor on its own arm of the spider, it is possible to locate the sensor in the correct position within the cup that represents the back surface of the prosthetic cover. Keeping everything miniaturized improves signal quality. This approach has been implemented at first as a bench circuit to provide a realistic example of how the production circuit will behave.

Figure 23A:
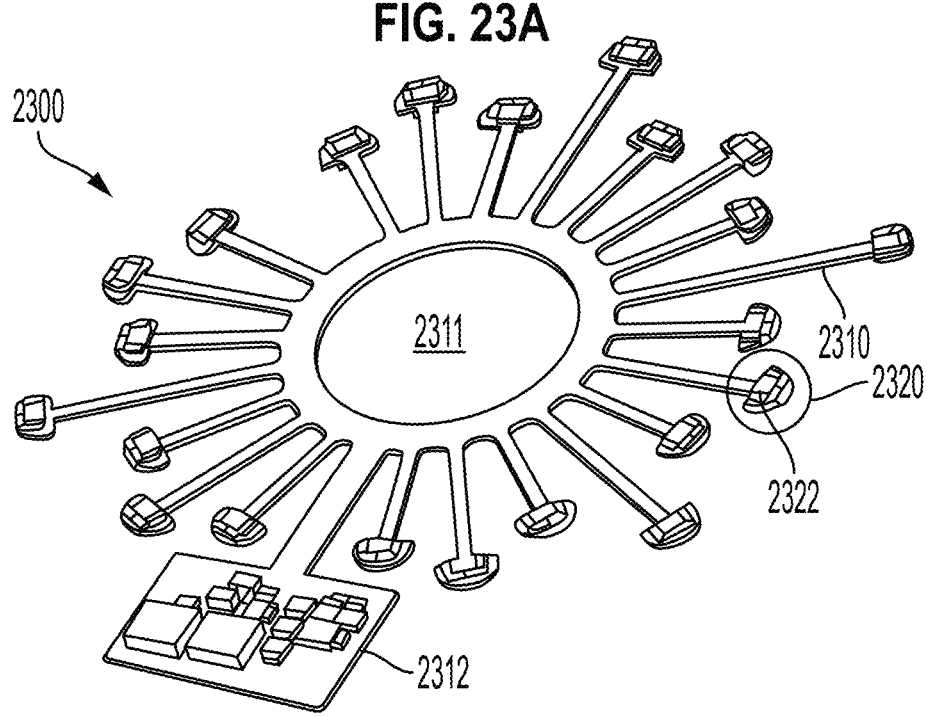
FIG. 23A and FIG. 23B are block diagrams that illustrate assembly of an example array of photodetectors for implant marker detection for a spatial model of the ocular prosthesis, according to an embodiment.
Figure 23B:
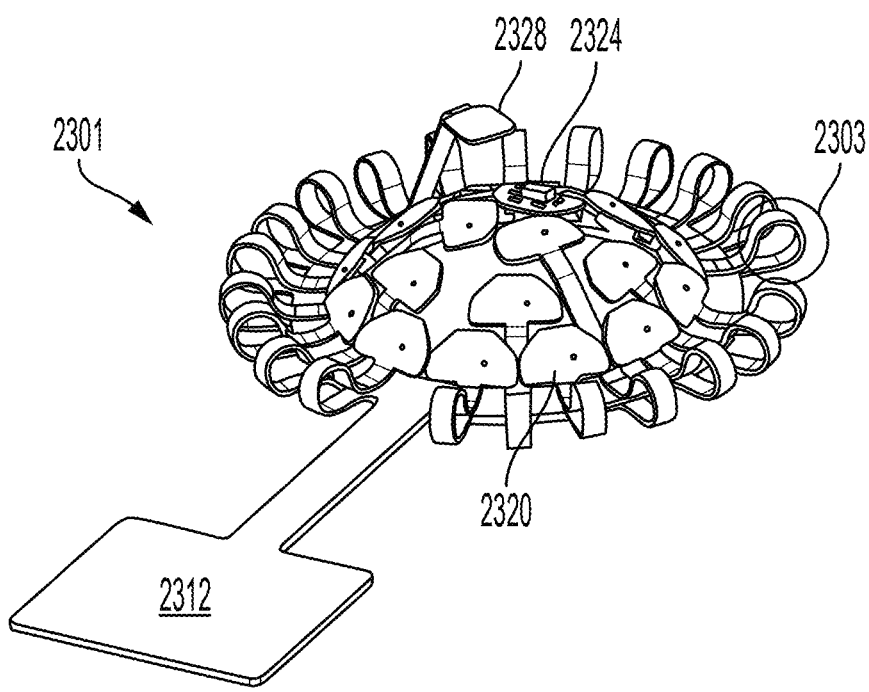
Figure 23C:
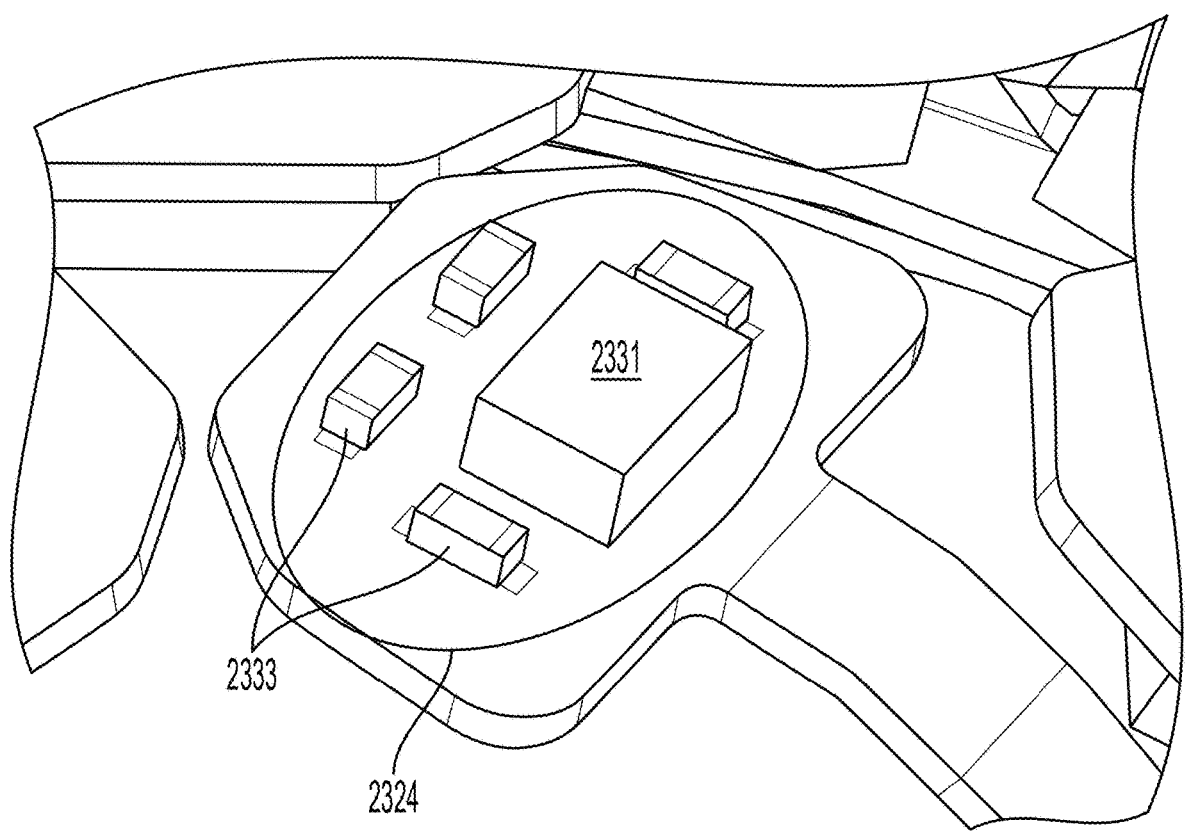
FIG. 23C is a block diagram that illustrates a detail of an example anterior face of one photodetector array element, according to an embodiment.

A look at a planned flex circuit card is provided in FIG. 23A through FIG. 23C. FIG. 23A and FIG. 23B are block diagrams that illustrate assembly of an example array of photodetectors for implant marker detection for a spatial model of the ocular prosthesis, according to an embodiment. The array of photodetectors are assembled on a flex circuit card 2310, depicted in a pre-folded state 2300 in FIG. 23A and folded state 2301 in FIG. 23B. The ring around a center opening 2311 fits the base dimension of a prosthetic cover, described below. There are 21 arms extending from the ring which carry the elements 2320 that include the optical sensors 2322 on a posterior face (in the folded state 2301) and support electronics 2324 on an anterior face (in the folded state 2301). Another arm carries the ambient light sensor 2328. When this flex circuit gets folded up, as depicted in FIG. 23B all of these elements fit into the space available in the prosthesis on a posterior side facing the orbital implant. Each "leaf" carries an optical sensor 2322 that lies on the back (posterior) side of the prosthesis. The sensors 2322 sit on a spherical surface with about 24 mm diameter, so that the sensors 2322 can view an optical beacon implanted in the conjunctiva of the patient in front of the orbital implant. The folded arms bring the sensors quite close together for good coverage of the optical beacon. Excess loops 2303 evident in the test flex card are not included in the deployed folded state by reducing appropriately the lengths of the arms of the flex card. The rectangle portion 2312 carries circuitry such as the microprocessor, battery management circuit, communications and beacon power source. These circuits are small enough to fit within the prosthesis, but they are packaged externally in a bench model in order to facilitate testing and debugs.

FIG. 23C is a block diagram that illustrates a detail of an example anterior face of one photodetector array element 2320, according to an embodiment. This face is directed to the anterior of the ocular prosthesis when in the folded state 2310 and includes support electronics 2324, such as amplifier 2331 and other circuit components 2333, such as resisters and capacitors. The amplifier 2324 sits directly behind the optical sensor. These are "0201" surface mount components, just 0.020" long by 0.010" square. Power, ground, input and output signals travel down the arms to the "ring" and then around to the microprocessor. In some embodiments, the signals are buried between power and ground planes for good noise performance.

Figure 24A:
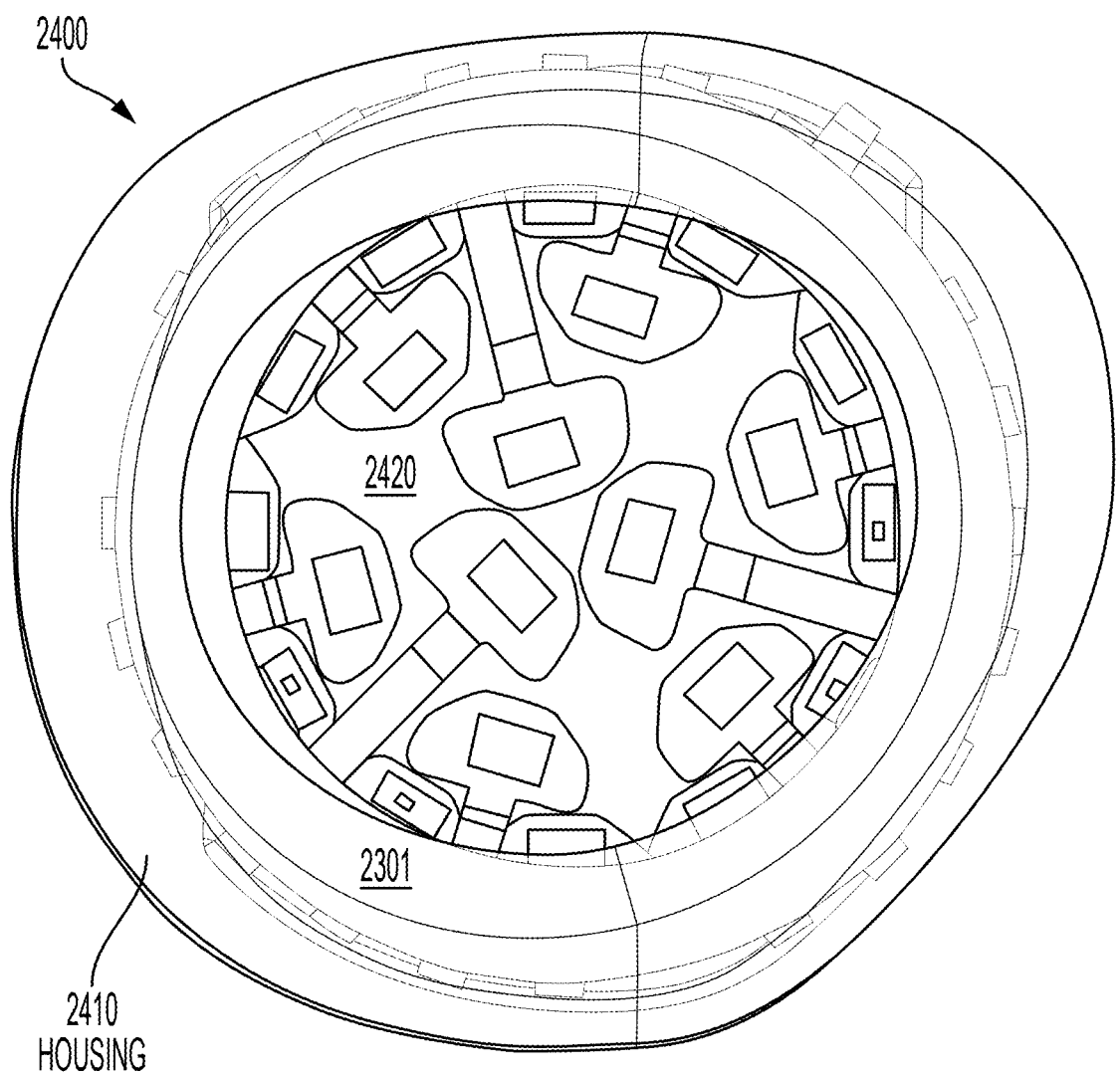
FIG. 24A through FIG. 24D are block diagrams that illustrate an example spatial model of an ocular prosthesis, according to an embodiment.
Figure 24B:
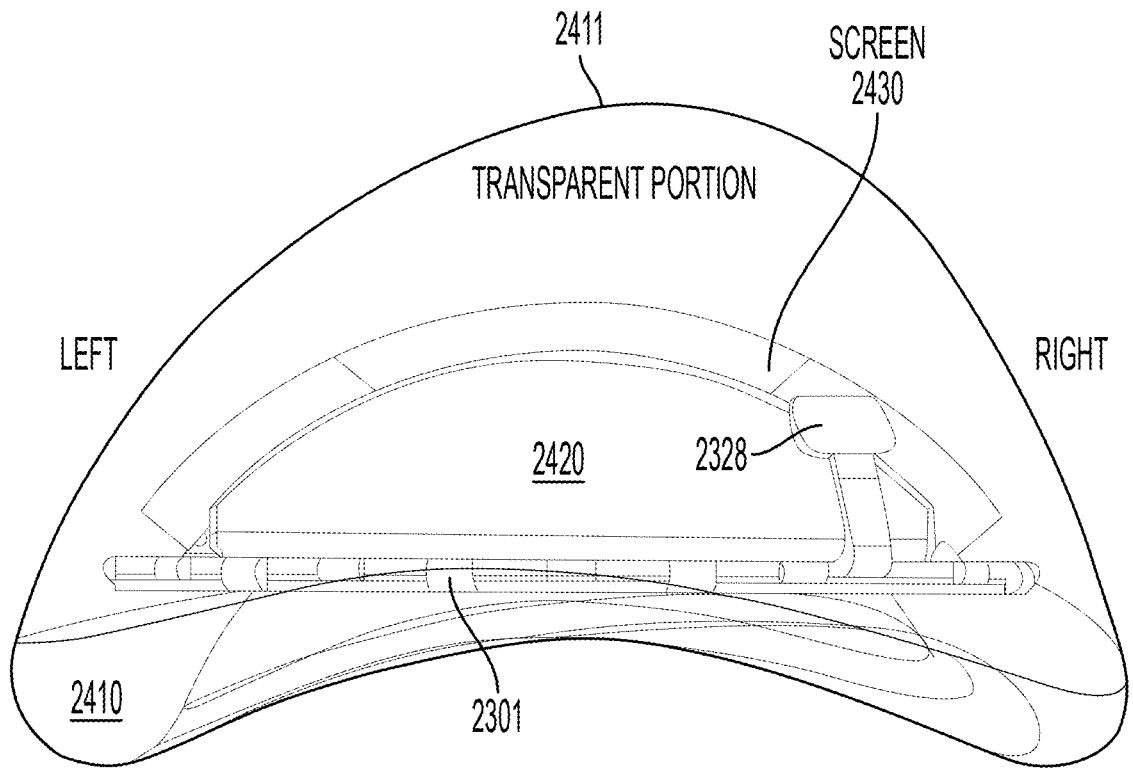
Figure 24C:
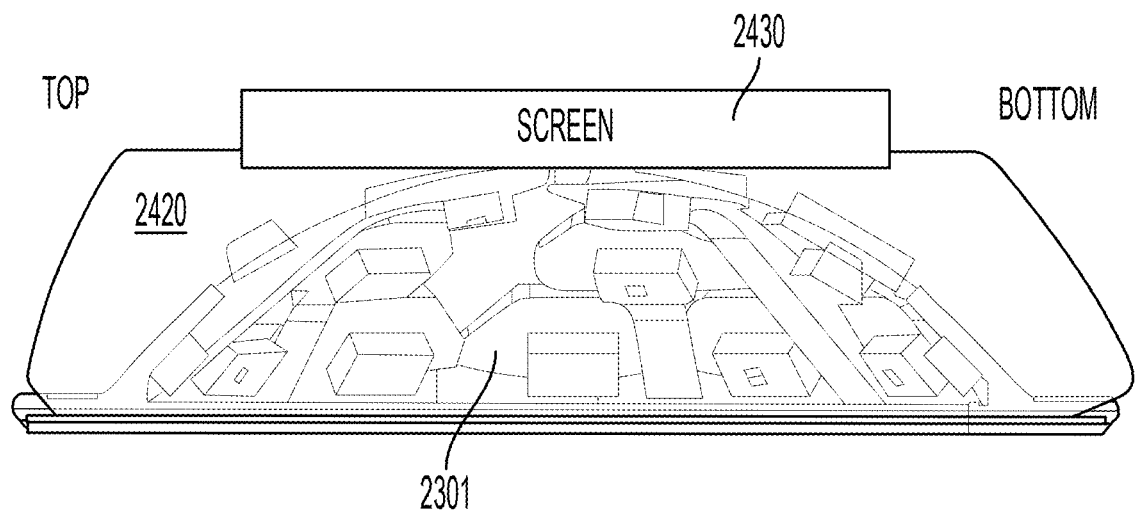

FIG. 24A through FIG. 24C are block diagrams that illustrate an example spatial model of an ocular prosthesis, according to an embodiment. When everything is assembled into the prosthesis 2400, the view from the back looks like that depicted in FIG. 24A. This gives a better picture of how the sensors are located over the orbital implant in folded state 2301. Note that the latest sensor configuration has no "north pole" sensor. The old configuration was 1-5-10 sensors in three rings. The new configuration is 3-6-12 sensors to provide good coverage while keeping the sensors as close as possible to the beacon (for better space utilization). The flex circuit board in folded state 2301 sits inside a cover or housing 2410, that is transparent in at least a portion anterior to the a display device. Apparent in FIG. 24A, beyond the flex circuit in folded state 2301 is a shaped battery 2420.

FIG. 24B is a cross-sectional view of the prosthesis 2400 from left to right. The flex circuit, in folded state 2301, shows as a thin object near the bottom of the figure, with the ambient light sensor 2328 extending outside the sphere of the other sensors. The 21 optical position sensors and their flexible arms are hidden in this view. In the production version of the circuitry, the "saddlebag" areas (lower left and right) of housing 2410 house the remaining circuits such as CPU, battery management, and communications. This region of the prosthesis is mostly inaccessible to other design elements, so the space is essentially "free." There is actually more space in the saddlebags than required by the planned circuitry. The central object in FIG. 24B is the battery 2420 and the dark object is the curved display screen 2430. These two elements have proven to be the most difficult to package inside the prosthesis. The goal in this design iteration was to utilize a "single curved" display. This is conceived as being a flat display that is built on a flexible substrate. The substrate can be bent in either axis (chosen here to be the long horizontal direction) but not in both axes at once. In FIG. 24B it looks like the display fits easily inside the envelope of the prosthesis, but in truth it's a very tight fit in the other dimensions. The housing 2410 includes a transparent portion 2411 so that the screen 2430 is visible at the anterior of the prosthesis 2400. In some embodiments, the entire housing 2410 is made of transparent material.

FIG. 24C is a cutaway view of the prosthesis from top to bottom without the housing. The flex circuit, in folded state 2301, shows as the lower sphere portion. The cutaway is taken through the center of the prosthesis. The display screen 2430 looks flat here because the slice axis is in the non-curved vertical direction. Note how the display screen 2430 sits directly on top of the central optical sensors and the battery 2420.

Figure 24D:
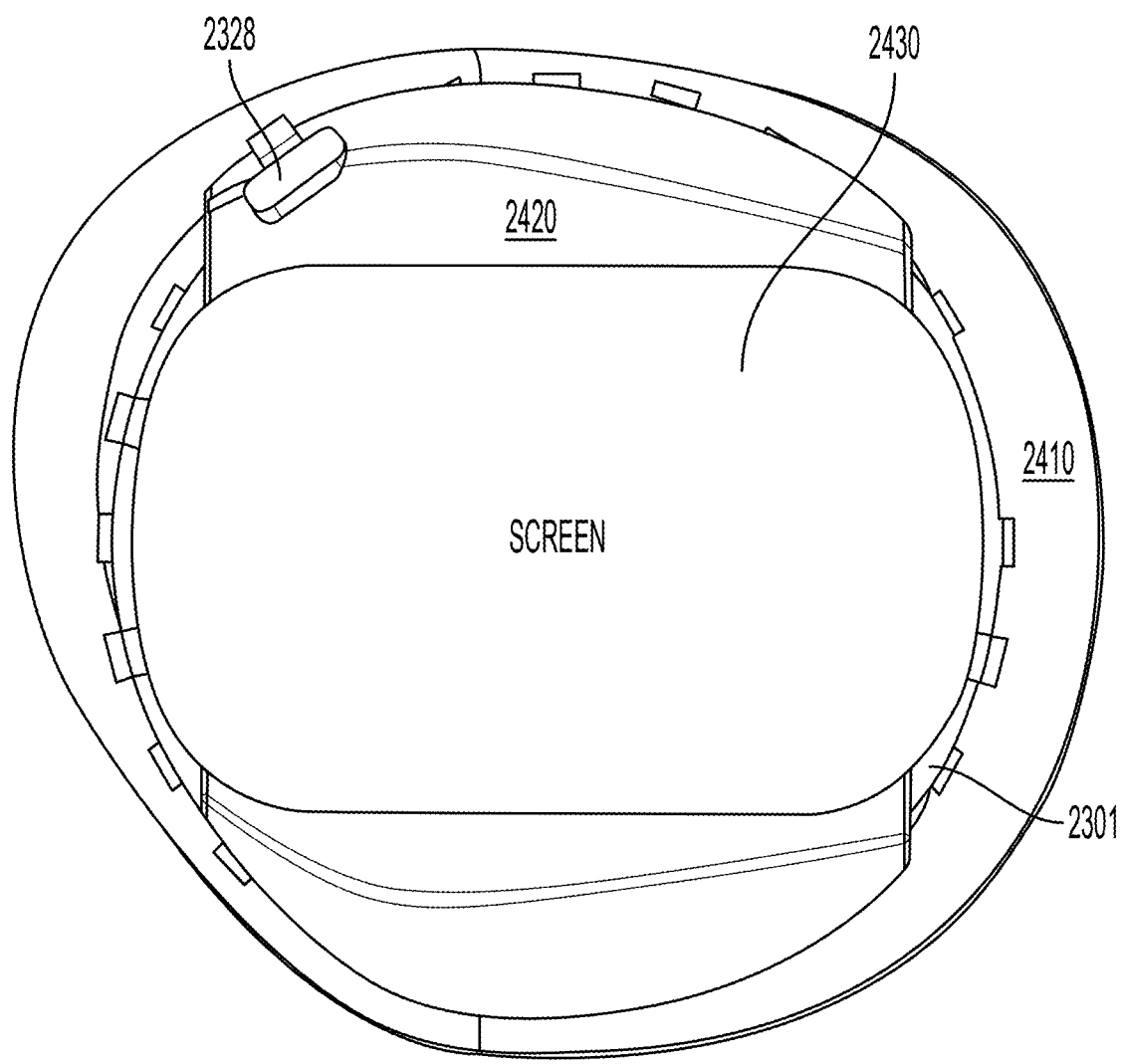

FIG. 24D is a front (anterior) view of prosthesis 2400. The housing 2410 is transparent enough to reveal the screen 2430, the battery 2430 behind the screen, the ambient light sensor 2328 and some other portions of the flex circuit card in folded state 2301. The battery is depicted in several shades of gray because the battery changes surface angles to fit within the housing 2410. Note that the corners of the display screen 2430 are rounded to keep the screen 2430 from penetrating the housing 2410 of the prosthesis 2400. This model of the display screen 2430 is 25 mm×14.5 mm×1.5 mm. It is anticipated that this shape provides adequate coverage for all sensible pointing angles of the eye. It appears that the clipped corners do not harm the appearance, because these areas will normally be covered by the patient's eyelids.

Figure 25A:
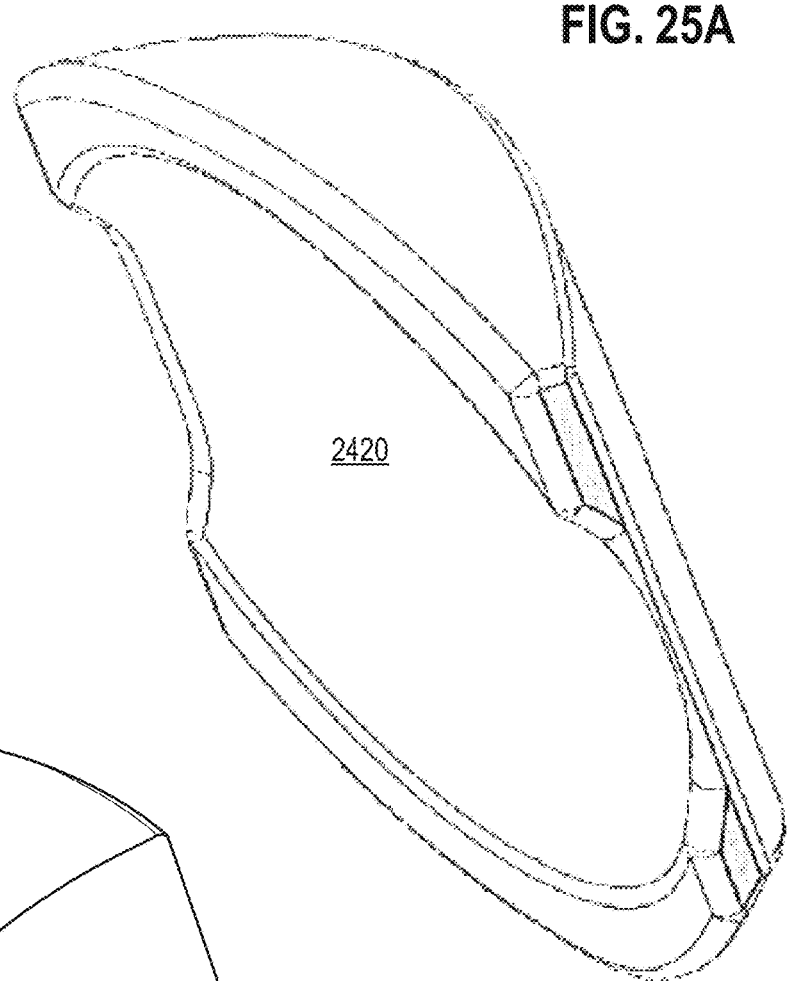
FIG. 25A and FIG. 25B are block diagrams that illustrate an example shaped battery component of the spatial model of an ocular prosthesis, according to an embodiment.
Figure 25B:
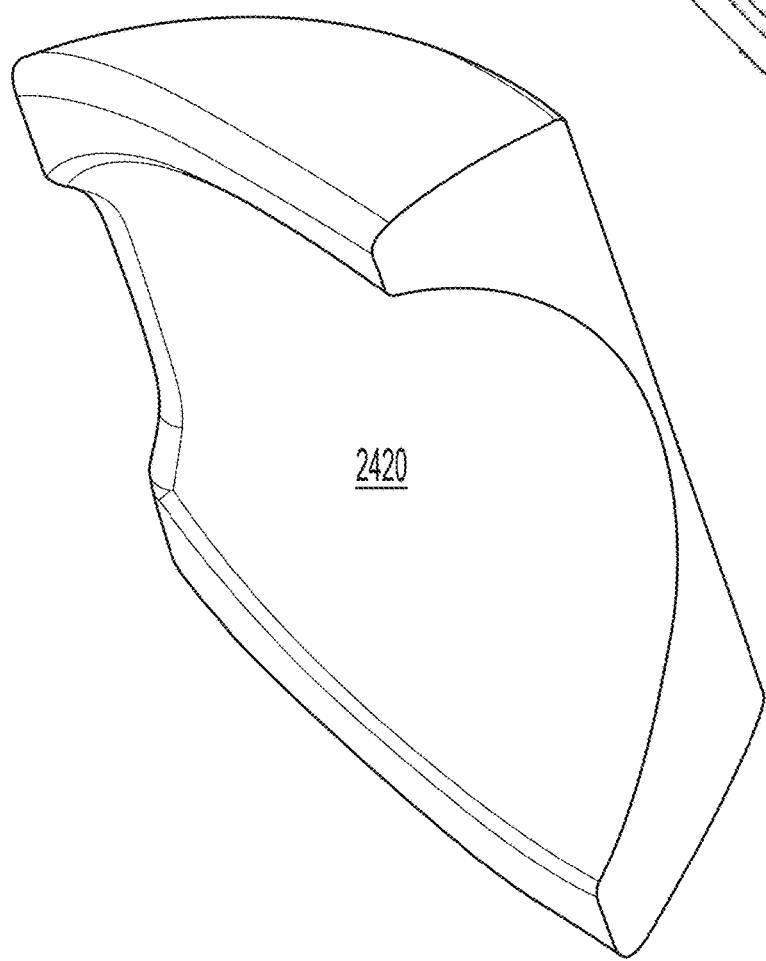

FIG. 25A and FIG. 25B are block diagrams that illustrate an example shaped battery component 2420 of the spatial model of an ocular prosthesis 2400, according to an embodiment. With the display screen 2410 taking up all of the "good" volume of the prosthesis, the battery needs to fit in the space between the screen and the flex circuit board with photosensors in folded state 2301, depicted din FIG. 25A in perspective view. The bottom of the battery 2420 is shaped to wrap around the optical sensors; and, the central area is thinned to make room for the display. The thinned central portion is shown in the cutaway perspective view in FIG. 25B. This intricate shape suggests using a printable battery technology. A solution was not found to position one or more standard batteries in the prosthesis, always with the goal of yielding at least 80 mW-hrs of capacity (25 mA-hrs at 3.3V). The good news is that a rechargeable lithium ion battery of 80 mW-hrs capacity requires a volume of just 470 mm³. By comparison, the printable battery shown has a volume of 1800 mm³. This fact provides a choice in battery solutions. A fully printable battery could utilize the full 1800 mm³ volume. This is about 4× the volume required by lithium ion, so the printable battery could have a much less space efficient chemistry, such as one of the zinc formulations. Another choice is a lithium polymer battery with a nonprintable, but custom shape. Using the lithium chemistry, one could simplify the shape by giving up a lot of volume, especially in the interior of the battery space.

3. Processor Hardware Overview

Figure 21:
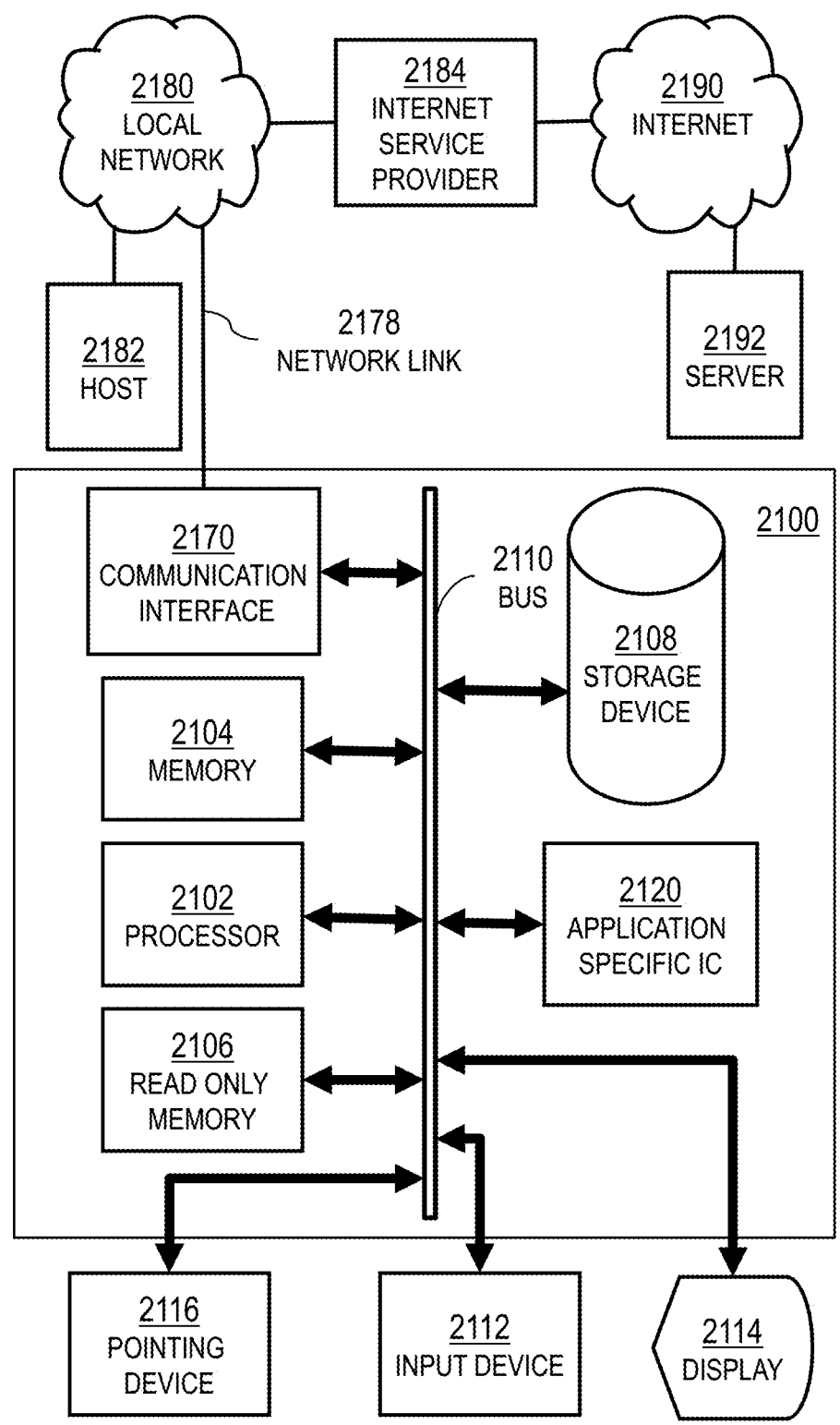
FIG. 21 is a block diagram that illustrates a computer system upon which an embodiment of the invention may be implemented.

FIG. 21 is a block diagram that illustrates a computer system 2100 upon which an embodiment of the invention may be implemented. Computer system 2100 includes a communication mechanism such as a bus 2110 for passing information between other internal and external components of the computer system 2100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 2100, or a portion thereof, constitutes a means for performing one or more steps of one or more methods described herein.

A sequence of binary digits constitutes digital data that is used to represent a number or code for a character. A bus 2110 includes many parallel conductors of information so that information is transferred quickly among devices coupled to the bus 2110. One or more processors 2102 for processing information are coupled with the bus 2110. A processor 2102 performs a set of operations on information. The set of operations include bringing information in from the bus 2110 and placing information on the bus 2110. The set of operations also typically include comparing two or more units of information, shifting positions of units of information, and combining two or more units of information, such as by addition or multiplication. A sequence of operations to be executed by the processor 2102 constitutes computer instructions.

Computer system 2100 also includes a memory 2104 coupled to bus 2110. The memory 2104, such as a random access memory (RAM) or other dynamic storage device, stores information including computer instructions. Dynamic memory allows information stored therein to be changed by the computer system 2100. RAM allows a unit of information stored at a location called a memory address to be stored and retrieved independently of information at neighboring addresses. The memory 2104 is also used by the processor 2102 to store temporary values during execution of computer instructions. The computer system 2100 also includes a read only memory (ROM) 2106 or other static storage device coupled to the bus 2110 for storing static information, including instructions, that is not changed by the computer system 2100. Also coupled to bus 2110 is a non-volatile (persistent) storage device 2108, such as a magnetic disk or optical disk, for storing information, including instructions, that persists even when the computer system 2100 is turned off or otherwise loses power.

Information, including instructions, is provided to the bus 2110 for use by the processor from an external input device 2112, such as a keyboard containing alphanumeric keys operated by a human user, or a sensor. A sensor detects conditions in its vicinity and transforms those detections into signals compatible with the signals used to represent information in computer system 2100. Other external devices coupled to bus 2110, used primarily for interacting with humans, include an electronic display device 2114, such as a cathode ray tube (CRT) or a liquid crystal display (LCD), for presenting images, and a pointing device 2116, such as a mouse or a trackball or cursor direction keys, for controlling a position of a small cursor image presented on the display 2114 and issuing commands associated with graphical elements presented on the display 2114.

In the illustrated embodiment, special purpose hardware, such as an application specific integrated circuit (IC) 2120, is coupled to bus 2110. The special purpose hardware is configured to perform operations not performed by processor 2102 quickly enough for special purposes. Examples of application specific ICs include graphics accelerator cards for generating images for display 2114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 2100 also includes one or more instances of a communications interface 2170 coupled to bus 2110. Communication interface 2170 provides a two-way communication coupling to a variety of external devices that operate with their own processors, such as printers, scanners and external disks. In general the coupling is with a network link 2178 that is connected to a local network 2180 to which a variety of external devices with their own processors are connected. For example, communication interface 2170 may be a parallel port or a serial port or a universal serial bus (USB) port on a personal computer. In some embodiments, communications interface 2170 is an integrated services digital network (ISDN) card or a digital subscriber line (DSL) card or a telephone modem that provides an information communication connection to a corresponding type of telephone line. In some embodiments, a communication interface 2170 is a cable modem that converts signals on bus 2110 into signals for a communication connection over a coaxial cable or into optical signals for a communication connection over a fiber optic cable. As another example, communications interface 2170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 2170 sends and receives electrical, acoustic or electromagnetic signals, including infrared and optical signals, that carry information streams, such as digital data.

The term computer-readable medium is used herein to refer to any medium that participates in providing information to processor 2102, including instructions for execution. Such a medium may take many forms, including, but not limited to, non-volatile media, volatile media and transmission media. Non-volatile media include, for example, optical or magnetic disks, such as storage device 2108. Volatile media include, for example, dynamic memory 2104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 2102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 2102, except for carrier waves and other signals.

Logic encoded in one or more tangible media includes one or both of processor instructions on a computer-readable storage media and special purpose hardware, such as ASIC *2120.

Network link 2178 typically provides information communication through one or more networks to other devices that use or process the information. For example, network link 2178 may provide a connection through local network 2180 to a host computer 2182 or to equipment 2184 operated by an Internet Service Provider (ISP). ISP equipment 2184 in turn provides data communication services through the public, world-wide packet-switching communication network of networks now commonly referred to as the Internet 2190. A computer called a server 2192 connected to the Internet provides a service in response to information received over the Internet. For example, server 2192 provides information representing video data for presentation at display 2114.

The invention is related to the use of computer system 2100 for implementing the techniques described herein. According to one embodiment of the invention, those techniques are performed by computer system 2100 in response to processor 2102 executing one or more sequences of one or more instructions contained in memory 2104. Such instructions, also called software and program code, may be read into memory 2104 from another computer-readable medium such as storage device 2108. Execution of the sequences of instructions contained in memory 2104 causes processor 2102 to perform the method steps described herein. In alternative embodiments, hardware, such as application specific integrated circuit 2120, may be used in place of or in combination with software and a general purpose processor to implement the invention. Thus, embodiments of the invention are not limited to any specific combination of specific hardware and software with general purpose hardware.

The signals transmitted over network link 2178 and other networks through communications interface 2170, carry information to and from computer system 2100. Computer system 2100 can send and receive information, including program code, through the networks 2180, 2190 among others, through network link 2178 and communications interface 2170. In an example using the Internet 2190, a server 2192 transmits program code for a particular application, requested by a message sent from computer 2100, through Internet 2190, ISP equipment 2184, local network 2180 and communications interface 2170. The received code may be executed by processor 2102 as it is received, or may be stored in storage device 2108 or other non-volatile storage for later execution, or both. In this manner, computer system 2100 may obtain application program code in the form of a signal on a carrier wave.

Various forms of computer readable media may be involved in carrying one or more sequence of instructions or data or both to processor 2102 for execution. For example, instructions and data may initially be carried on a magnetic disk of a remote computer such as host 2182. The remote computer loads the instructions and data into its dynamic memory and sends the instructions and data over a telephone line using a modem. A modem local to the computer system 2100 receives the instructions and data on a telephone line and uses an infrared transmitter to convert the instructions and data to a signal on an infrared carrier wave serving as the network link 2178. An infrared detector serving as communications interface 2170 receives the instructions and data carried in the infrared signal and places information representing the instructions and data onto bus 2110. Bus 2110 carries the information to memory 2104 from which processor 2102 retrieves and executes the instructions using some of the data sent with the instructions. The instructions and data received in memory 2104 may optionally be stored on storage device 2108, either before or after execution by the processor 2102.

Figure 22:
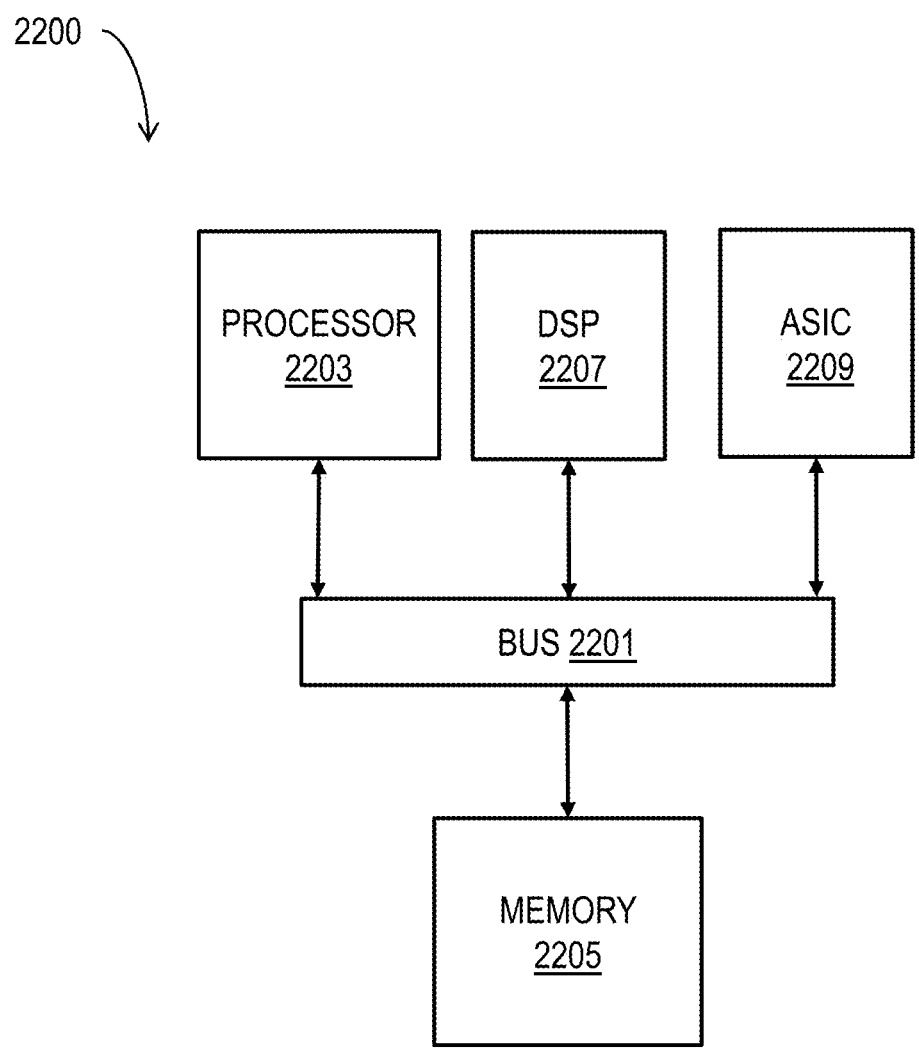
FIG. 22 illustrates a chip set upon which an embodiment of the invention may be implemented.

FIG. 22 illustrates a chip set 2200 upon which an embodiment of the invention may be implemented. Chip set 2200 is programmed to perform one or more steps of a method described herein and includes, for instance, the processor and memory components described with respect to FIG. 21 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2200, or a portion thereof, constitutes a means for performing one or more steps of a method described herein.

In one embodiment, the chip set 2200 includes a communication mechanism such as a bus 2201 for passing information among the components of the chip set 2200. A processor 2203 has connectivity to the bus 2201 to execute instructions and process information stored in, for example, a memory 2205. The processor 2203 may include one or more processing cores with each core configured to perform independently. A multi-core processor enables multiprocessing within a single physical package. Examples of a multi-core processor include two, four, eight, or greater numbers of processing cores. Alternatively or in addition, the processor 2203 may include one or more microprocessors configured in tandem via the bus 2201 to enable independent execution of instructions, pipelining, and multithreading. The processor 2203 may also be accompanied with one or more specialized components to perform certain processing functions and tasks such as one or more digital signal processors (DSP) 2207, or one or more application-specific integrated circuits (ASIC) 2209. A DSP 2207 typically is configured to process real-world signals (e.g., sound) in real time independently of the processor 2203. Similarly, an ASIC 2209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2203 and accompanying components have connectivity to the memory 2205 via the bus 2201. The memory 2205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2205 also stores the data associated with or generated by the execution of one or more steps of the methods described herein.

4. Alternatives and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. An ocular prosthetic system comprising:
    an implant marker configured to move with an orbital implant disposed in an eye socket of a subject; and
    an ocular prosthesis separate from the orbital implant, the ocular prosthesis comprising:
        a housing having a form factor shaped to fit in a stationary position under an eyelid of the subject and in front of the orbital implant, wherein an anterior portion of the form factor is curved similar to an anterior portion of a normal eyeball for the subject;
        a display device disposed within the housing and visible at an anterior portion of the housing;
        an implant detector disposed within the housing and configured to detect a position of the implant marker moving with the ocular implant, relative to the housing, when the housing is inserted under the eyelid of the subject and anterior to the orbital implant; and
        a processor disposed within the housing and configured to
            determine, at least in part, a human appearance for a visible portion of the eyeball of the subject based, at least in part, on the position of the implant marker, and
            render, at least in part, an image for presentation on the display device based on the human appearance for the visible portion of the eyeball of the subject including position and translation of an image of an iris in a display area on the display device.

2. The system as recited in claim 1, further comprising an external wearable device configured to provide power to the ocular prosthesis.

3. The system as recited in claim 1, further comprising an external wearable device configured to determine, at least in part, the human appearance for the visible portion of the eyeball of the subject.

* * * * *